US011155584B2

(12) United States Patent
Chilkoti et al.

(10) Patent No.: US 11,155,584 B2
(45) Date of Patent: Oct. 26, 2021

(54) UNSTRUCTURED NON-REPETITIVE POLYPEPTIDES HAVING LCST BEHAVIOR

(71) Applicant: Duke University, Durham, NC (US)

(72) Inventors: Ashutosh Chilkoti, Durham, NC (US); Nicholas Tang, Durham, NC (US); Garrett Kelly, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/335,734

(22) PCT Filed: Sep. 22, 2017

(86) PCT No.: PCT/US2017/052887
§ 371 (c)(1),
(2) Date: Mar. 22, 2019

(87) PCT Pub. No.: WO2018/057847
PCT Pub. Date: Mar. 29, 2018

(65) Prior Publication Data
US 2020/0017557 A1    Jan. 16, 2020

Related U.S. Application Data

(60) Provisional application No. 62/399,123, filed on Sep. 23, 2016.

(51) Int. Cl.
| | | |
|---|---|---|
| *C07K 14/31* | (2006.01) | |
| *A61K 47/65* | (2017.01) | |
| *G01N 33/68* | (2006.01) | |
| *A61K 38/00* | (2006.01) | |

(52) U.S. Cl.
CPC .............. *C07K 14/31* (2013.01); *A61K 47/65* (2017.08); *G01N 33/68* (2013.01); *A61K 38/00* (2013.01); *C07K 2319/02* (2013.01); *C07K 2319/21* (2013.01); *G01N 2800/52* (2013.01)

(58) Field of Classification Search
CPC .... C07K 14/31; C07K 14/00; C07K 2319/00; C07K 2319/02; C07K 2319/21; A61K 38/00; A61K 47/65; A61P 35/00; G01N 2800/52; G01N 33/68
See application file for complete search history.

(56) References Cited

U.S. PATENT DOCUMENTS

| | | | |
|---|---|---|---|
| 4,554,101 A | 11/1985 | Hopp | |
| 4,976,734 A | 12/1990 | Urry et al. | |
| 5,250,516 A | 10/1993 | Urry | |
| 5,336,256 A | 8/1994 | Urry | |
| 5,578,577 A | 11/1996 | Ching et al. | |
| 5,580,859 A | 12/1996 | Felgner et al. | |
| 5,676,646 A | 10/1997 | Hofmann et al. | |
| 5,679,647 A | 10/1997 | Carson et al. | |
| 5,702,359 A | 12/1997 | Hofmann et al. | |
| 5,703,055 A | 12/1997 | Felgner et al. | |
| 6,068,650 A | 5/2000 | Hofmann et al. | |
| 6,096,020 A | 8/2000 | Hofmann | |
| 6,120,493 A | 9/2000 | Hofmann | |
| 6,150,148 A | 11/2000 | Nanda et al. | |
| 6,181,964 B1 | 1/2001 | Hofmann et al. | |
| 6,192,270 B1 | 2/2001 | Hofmann et al. | |
| 6,207,749 B1 | 3/2001 | Mayes et al. | |
| 6,208,893 B1 | 3/2001 | Hofmann | |
| 6,216,034 B1 | 4/2001 | Hofmann et al. | |
| 6,233,482 B1 | 5/2001 | Hofmann et al. | |
| 6,241,701 B1 | 6/2001 | Hofmann | |
| 6,245,515 B1 | 6/2001 | Vogelstein et al. | |
| 6,296,831 B1 | 10/2001 | Weller et al. | |
| 6,302,874 B1 | 10/2001 | Zhang et al. | |
| 6,623,950 B1 | 9/2003 | Osten et al. | |
| 6,660,247 B1 | 12/2003 | Gutowska et al. | |
| 6,841,617 B2 | 1/2005 | Jeong et al. | |
| 6,852,834 B2 | 2/2005 | Chilkoti | |
| 6,869,588 B2 | 3/2005 | Weller et al. | |
| 7,033,571 B2 | 4/2006 | Gutowska et al. | |
| 7,087,244 B2 | 8/2006 | Jeong et al. | |
| 7,429,458 B2 | 9/2008 | Chilkoti | |
| 7,664,545 B2 | 2/2010 | Westersten et al. | |
| 7,674,882 B2 | 3/2010 | Kaplan et al. | |
| 8,129,330 B2 | 3/2012 | Martinez et al. | |
| 8,283,125 B2 | 10/2012 | Cebolla Ramirez et al. | |

(Continued)

FOREIGN PATENT DOCUMENTS

| | | |
|---|---|---|
| CA | 2327325 A1 | 11/1999 |
| CA | 2423488 A1 | 4/2002 |

(Continued)

OTHER PUBLICATIONS

Chang et al. Thermoprecipitation of Glutathione S-Transferase by Glutathione-Poly(N-isopropylacrylamide) Prepared by RAFT Polymerization. Macromolecular Rapid Communications. Oct. 2010, vol. 31, pp. 1691-1695. (Year: 2010).*
De Leon-Rodriguez et al. Multifunctional thermoresponsive designer peptide hydrogels. Acta Biomaterialia, 2017, vol. 47, pp. 40-49. (Year: 2017).*
UniProtKB—P15214 (GST_PROM1) acessed online at https://www.uniprot.org/uniprot/P15214 6/on Jun. 8, 2021. 7 pages. (Year: 2021).*
Alarcon et al., "Exendin 4 controls insulin production in rat islet beta cells predominantly by potentiation of glucose-stimulated proinsulin biosynthesis at the translational level," Diabetologia, 2006, 49(12):2920-2929.

(Continued)

*Primary Examiner* — Marcela M Cordero Garcia
(74) *Attorney, Agent, or Firm* — Michael Best & Friedrich LLP

(57) ABSTRACT

Described herein are unstructured polypeptides lacking any discernible repeat motif. Also described herein are fusion proteins including at least one of the unstructured polypeptides and at least one binding polypeptide. Further described are methods for treating a disease in a subject in need thereof. The methods may include administering to the subject an effective amount of the fusion protein.

29 Claims, 6 Drawing Sheets

Specification includes a Sequence Listing.

(56) References Cited

U.S. PATENT DOCUMENTS

| | | |
|---|---|---|
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,841,414 B1 | 9/2014 | Raucher et al. |
| 8,912,310 B2 | 12/2014 | Chilkoti et al. |
| 9,127,047 B2 | 9/2015 | Chilkoti |
| 9,132,178 B2 | 9/2015 | Philip |
| 9,592,303 B2 | 3/2017 | Chilkoti et al. |
| 9,771,396 B2 | 9/2017 | Chilkoti et al. |
| 10,385,115 B2 * | 8/2019 | Chilkoti ............... A61K 9/0019 |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0175290 A1 | 9/2003 | Renner et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2010/0015070 A1 | 1/2010 | Bollschweiler et al. |
| 2010/0048473 A1 | 2/2010 | Chaikof et al. |
| 2010/0241054 A1 | 9/2010 | Dacey, Jr. et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0305718 A1 | 12/2011 | Mugica et al. |
| 2012/0121709 A1 | 5/2012 | Chilkoti et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0281624 A1 | 10/2013 | Chilkoti et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0233714 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0171337 A1 | 6/2018 | O'Neill et al. |
| 2018/0200196 A1 | 7/2018 | Fahmy et al. |
| 2018/0258157 A1 * | 9/2018 | Chilkoti ................. C07K 14/78 |
| 2018/0326044 A1 | 11/2018 | Carter |
| 2018/0327752 A1 | 11/2018 | Pillay et al. |
| 2019/0016763 A1 | 1/2019 | Kitazawa et al. |
| 2019/0345228 A1 * | 11/2019 | Chilkoti ............... A61K 9/0019 |
| 2020/0148724 A1 * | 5/2020 | Chilkoti ............... A61K 9/0024 |
| 2021/0154143 A1 * | 5/2021 | Chilkoti ................. A61K 47/62 |

FOREIGN PATENT DOCUMENTS

| | | |
|---|---|---|
| EP | 2664340 B1 | 2/2020 |
| JP | 2014-156428 A | 8/2014 |
| JP | 2014-534265 A | 12/2014 |
| WO | WO 2003/040165 A2 | 10/2002 |
| WO | WO 2004/096124 A2 | 11/2004 |
| WO | WO 2006/004778 A2 | 1/2006 |
| WO | WO2006/110292 A2 | 10/2006 |
| WO | WO 2007/073486 A2 | 6/2007 |
| WO | WO 2007/108013 A2 | 9/2007 |
| WO | WO 2007/134245 A2 | 11/2007 |
| WO | 2008/012543 A1 | 1/2008 |
| WO | 2008/030968 A2 | 3/2008 |
| WO | WO 2009/067584 A1 | 5/2009 |
| WO | WO 2010/054699 A1 | 5/2010 |
| WO | WO 2010/057154 A1 | 5/2010 |
| WO | WO 2010/096422 A1 | 8/2010 |
| WO | 2011/025572 A1 | 3/2011 |
| WO | WO 2011/123813 A2 | 10/2011 |
| WO | WO2012/162426 A1 | 11/2012 |
| WO | WO 2013/065009 A1 | 5/2013 |
| WO | WO 2014/194244 A1 | 12/2014 |
| WO | WO2015/011231 A1 | 1/2015 |
| WO | WO 2015/130846 A2 | 9/2015 |
| WO | WO 2016/065273 A1 | 4/2016 |
| WO | WO 2016/090103 A1 | 6/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |
| WO | 2017/192449 A1 | 11/2017 |
| WO | WO 2018/144854 A1 | 8/2018 |
| WO | 2019/147954 A1 | 8/2019 |
| WO | WO2020/037214 A1 | 2/2020 |

OTHER PUBLICATIONS

American Diabetes Association (2018) Standards of medical care in diabetes—2018. Diabetes Care 41(Suppl 1):S1-S159.

Arner et al., "FGF21 attenuates lipolysis in human adipocytes—a possible link to improved insulin sensitivity," FEBS Lett, 2008, 582(12):1725-1730.

Badi, "Non-linear PEG-based thermoresponsive polymer systems," Progress in Polymer Science, 2017, 66, 54-79.

Baggio et al., "Biology of Incretins: GLP-1 and GIP," Gastroenterology, 2007, 132(6):2131-2157.

Beenken et al., "The FGF family: biology, pathophysiology and therapy," Nat Rev Drug Discov, 2009, 8(3):235-253.

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, 2017, 27(12):1-9.

Bobo et al., "Nanoparticle-based medicines: a review of FDA-approved materials and clinical trials to date." Pharmaceutical research 33.10 (2016): 2373-2387.

Buteau et al., "Glucagon-like peptide-1 prevents beta cell glucolipotoxicity," Diabetologia, 2004, 47(5):806-815.

Butler et al., "β-Cell Deficit and Increased β-Cell Apoptosis in Humans With Type 2 Diabetes," Diabetes, 2003, 52(1):102-110.

(56) References Cited

OTHER PUBLICATIONS

Cabrera et al., "Automated, High-Throughput Assays for Evaluation of Human Pancreatic Islet Function," Cell Transplant, 2008, 16(10):1039-1048.
Cabrera et al., "Glutamate Is a Positive Autocrine Signal for Glucagon Release," Cell Metab, 2008, 7(6):545-554.
Centers for Disease Control and Prevention (2017) National Diabetes Statistics Report, 2017. ed U.S. Dept of Health and Human Services (Atlanta).
Chatterjee et al., "Type 2 diabetes," The Lancet, 2017, 389(10085): 2239-2251.
Chilkoti et al., "Stimulus responsive elastin biopolymers: applications in medicine and biotechnology," Curr Opin Chem Biol, 2006, 10(6):652-657.
Coskun et al., "Fibroblast Growth Factor 21 Corrects Obesity in Mice," Endocrinology, 2008, 149(12):6018-6027.
Day et al., "A new glucagon and GLP-1 co-agonist eliminates obesity in rodents," Nat Chem Biol, 2009, 5:749.
DeYoung et al.,"Encapsulation of exenatide in poly-(D,L-lactide-co-glycolide) microspheres produced an investigational long-acting once-weekly formulation for type 2 diabetes," Diabetes Technol Ther, 2011, 13, 1145-1154.
Ding et al., "βKlotho Is Required for Fibroblast Growth Factor 21 Effects on Growth and Metabolism," Cell Metab, 2012, 16(3):387-393.
Drucker "Mechanisms of Action and Therapeutic Application of Glucagon-like Peptide-1," Cell Metab, 2018, 27(4):740-756.
Drucker, "Incretin action in the pancreas: potential promise, possible perils, and pathological pitfalls," Diabetes, 2013, 62, 3316-3323.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
El-Assaad et al., "Saturated Fatty Acids Synergize with Elevated Glucose to Cause Pancreatic β-Cell Death," Endocrinology, 2003, 144(9):4154-4163.
Finan et al., "A rationally designed monomeric peptide triagonist corrects obesity and diabetes in rodents," Nat Med, 2015, 21:27-36.
Finan et al., "Unimolecular Dual Incretins Maximize Metabolic Benefits in Rodents, Monkeys, and Humans," Sci Transl Med, 2013, 5(209):209ra151.
Fosgerau et al., "Peptide therapeutics: current status and future directions," Drug Discovery Today, 2015, 20, 122-128.
Gaich et al., "The Effects of LY2405319, an FGF21 Analog, in Obese Human Subjects with Type 2 Diabetes," Cell Metab, 2013, 18(3):333-340.
Ganson et al., "Pre-existing anti-polyethylene glycol antibody linked to first-exposure allergic reactions to pegnivacogin, a PEGylated RNA aptamer," J Allergy Clin Immunol, 2016, 137(5): 1610-1613, e1617.
Gao, "Site-specific andin situgrowth of stealth polymer conjugates of proteins with significally improved pharmacology," Journal of Controlled Release, 2013, 172(1):e116-e117.
Gilroy et al., "Fusion of fibroblast growth factor 21 to a thermally responsive biopolymer forms an injectable depot with sustained anti-diabetic action," J Control Release, 2018, 277:154-164.
Gu et al., "Enzymatic Synthesis of Nucleobase-Modified Single-Stranded DNA Offers Turnable Resistance to Nuclease Degradation," Biomacromolecules, 2018, 19, 3525-3535.
Gu et al., "Photocontrolled micellar aggregation of amphiphilic DNA-azobenzene conjugates," Colloids Surfaces B: Biointerfaces, 2015, 135, 126-132.
Ha et al., "Immunoglobulin Fc Heterodimer Platform Technology: From Design to Applications in Therapeutic Antibodies and Proteins," Front Immunol, 2016, 7(394) (in English).
Hampp et al., "Use of Antidiabetic Drugs in the U.S., 2003-2012," Diabetes Care, 2014, 37: 1367-1374.
Hart et al., "Attenuation of FGF signalling in mouse β-cells leads to diabetes," Nature, 2000, 408:864.

Ito et al., "Impaired negative feedback suppression of bile acid synthesis in mice lacking βKlotho," J Clin Invest, 2005, 115(8):2202-2208.
Johnson et al., "Fibroblast Growth Factor 21 Reduces the Severity of Cerulein-Induced Pancreatitis in Mice," Gastroenterology, 2009, 137(5):1795-1804.
Kaspar et al., "Future directions for peptide therapeutics development," Drug Discovery Today, 2013, 18, 807-817.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, 2015, 26(11):608-617.
Kharitonenkov et al., "Fibroblast growth factor 21 night watch: advances and uncertainties in the field," J Intern Med, 2016, 281(3):233-246.
Kharitonenkov et al., "Inventing new medicines: The FGF21 story," Mol Metab, 2014, 3(3):221-229.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, 2007, 30, 1487-93.
Kurosu et al., "Tissue-specific Expression of βKlotho and Fibroblast Growth Factor (FGF) Receptor Isoforms Determines Metabolic Activity of FGF19 and FGF21," J Biol Chem, 2007, 282(37):26687-26695.
Laybutt et al., "Endoplasmic reticulum stress contributes to beta cell apoptosis in type 2 diabetes," Diabetologia, 2007, 50(4):752-763.
Lee et al., "Nanoparticle-Delivered Chemotherapy: Old Drugs in New Packages." Oncology (Williston Park, NY) 31.3 (2017): 198-208.
Lee et al., "Structures of β-klotho reveal a 'zip code'-like mechanism for endocrine FGF signaling," Nature, 2018, 553:501-505.
Leibowitz et al., "Glucose-Regulated Proinsulin Gene Expression Is Required for Adequate Insulin Production during Chronic Glucose Exposure," Endocrinology, 2002, 143(9):3214-3220.
Li et al., "Prediction of solvent-induced morphological changes of polyelectrolyte diblock copolymer micelles," Soft Matter, 2015, 11(42): 8236-45.
Lin et al., "Adiponectin Mediates the Metabolic Effects of FGF21 on Glucose Homeostasis and Insulin Sensitivity in Mice," Cell Metab, 2013, 17(5):779-789.
Lin et al., "Functional expression of a biologically active fragment of soluble gp130 as an ELP-fusion protein in transgenic plants: purification via inverse transition cycling," Biochem J, 2006, 398(3):577-583.
Lin et al., "Statistical properties of the traditional algorithm-based designs for phase I cancer clinical trials," Biostatistics, 2001, 2(2):203-215.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, 2006, 39, 893-896.
Magnusson et al., "Ion-Sensitive "Isothermal" Responsive Polymers Prepared in Water," Journal of the American Chemical Society, 2008, 130, 10852-10853.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, 2008, 93(12):4810-4817.
Meier et al., "Determination of Optimal Sample Size for Quantification of β-Cell Area, Amyloid Area and β-Cell Apoptosis in Isolated Islets," J Histochem Cytochem, 2015, 63(8):663-673.

(56) References Cited

OTHER PUBLICATIONS

Mu et al., "FGF21 Analogs of Sustained Action Enabled by Orthogonal Biosynthesis Demonstrate Enhanced Antidiabetic Pharmacology in Rodents," Diabetes, 2012, 61(2):505-512.
Nanoprecision Medical, "Pipeline, Type II Diabetes," <http://www.nanoprecisionmedical.com/pipeline/diabetes> webpage available as early as Aug. 2018.
Nauck "Glucagon-like Peptide 1 (GLP-1) in the Treatment of Diabetes," Horm Metab Res, 2004, 36(11/12):852-858 (in English).
Nies et al., "Fibroblast Growth Factor Signaling in Metabolic Regulation," Front Endocrinol, 2016, 6(193) (in English).
Ozer et al., "Site-Specific and Stoichiometric Stealth Polymer Conjugates of Therapeutic Peptides and Proteins," Bioconjug Chem, 2017, 28(3):713-723.
Pang et al., "A Modular Method for the High-Yield Synthesis of Site-Specific Protein-Polymer Therapeutics," Angew Chem Int Ed Engl, 2016, 55, 10296-10300.
Park et al., "Exendin-4 and exercise improve hepatic glucose homeostasis by promoting insulin signaling in diabetic rats," Metabolism, 2010, 59, 123-133.
Poitout et al., "Glucolipotoxicity: Fuel Excess and β-Cell Dysfunction," Endocr Rev, 2008, 29(3):351-366.
Potthoff et al., "Endocrine fibroblast growth factors 15/19 and 21: from feast to famine," Genes Dev, 2012, 26(4):312-324.
Qi et al., "A brush-polymer conjugate of exendin-4 reduces blood glucose for up to five days and eliminates poly(ethylene glycol) antigenicity," Nat Biomed Eng, 2016, 1:0002.
Ray et al., "Aptamer-mediated delivery of chemotherapy to pancreatic cancer cells." Nucleic acid therapeutics, 2012, 22(5): 295-305.
Riedel et al., "Engineered glucagon-like peptide-1-producing hepatocytes lower plasma glucose levels in mice," Am J Physiol Endocrinol Metab, 2009, 296(4):E936-E944.
Rodriguez-Diaz et al., "Alpha cells secrete acetylcholine as a non-neuronal paracrine signal priming beta cell function in humans," Nat Med, 2011, 17:888-892.
Schwendeman et al., "Injectable controlled release depots for large molecules," J Control Release, 2014, 190, 240-253.
Shusharina et al., "Micelles of Diblock Copolymers with Charged and Neutral Blocks: Scaling and Mean-Field Lattice Approaches," Macromolecules, 2000, 33(10): 3892-3901.
Singhal et al., "Fibroblast Growth Factor 21 (FGF21) Protects against High Fat Diet Induced Inflammation and Islet Hyperplasia in Pancreas," PLoS One, 2016, 11(2):e0148252.
Smith et al., "The Role of Beta Cell Glucagon-like Peptide-1 Signaling in Glucose Regulation and Response to Diabetes Drugs," Cell Metab, 2014, 19(6):1050-1057.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, 2017, 158(5):1314-1327.
Sun et al., "Autofluorescence Imaging of Living Pancreatic Islets Reveals Fibroblast Growth Factor-21 (FGF21)-Induced Metabolism," Biophys J, 2012, 103(11):2379-2388.
Sun et al., "On the Thermally Reversible Dynamic Hydration Behavior of Oligo(ethylene glycol) Methacrylate-Based Polymers in Water," Macromolecules, 2013, 46, 236-246.
Talukdar et al., "A Long-Acting FGF21 Molecule, PF-05231023, Decreases Body Weight and Improves Lipid Profile in Non-human Primates and Type 2 Diabetic Subjects," Cell Metab, 2016, 23(3):427-440.
Tang et al., "Enzymatic Polymerization of High Molecular Weight DNA Amphiphiles That Self-Assemble into Star-Like Micelles," Advanced Materials, 2014, 26(19): 3050-3054.
Tang et al., "High-Molecular-Weight Polynucleotides by Transferase-Catalyzed Living Chain-Growth Polycondensation," Angew. Chem., 2017, 56(24): 6778-6782.
Tomiyama et al., "Relevant use of Klotho in FGF19 subfamily signaling system in vivo," Proc Natl Acad Sci USA, 2010, 107(4):1666-71.
Tschop et al., "Unimolecular Polypharmacy for Treatment of Diabetes and Obesity," Cell Metab, 2016, 24(1):51-62.
Urry, "Free energy transduction in polypeptides and proteins based on inverse temperature transitions," Prog Biophys Mol Biol, 1992, 57(1):23-57.
Vlieghe et al., "Synthetic therapeutic peptides: science and market," Drug Discovery Today, 2010, 15, 40-56.
Wali et al., "Measuring Death of Pancreatic Beta Cells in Response to Stress and Cytotoxic T Cells," Methods in Molecular Biology, 2015, 1292:165-176.
Wei et al., "Fibroblast growth factor 21 promotes bone loss by potentiating the effects of peroxisome proliferator-activated receptor γ," Proc Natl Acad Sci USA, 2012, 109(8):3143-3148.
Wente et al., "Fibroblast Growth Factor-21 Improves Pancreatic β-Cell Function and Survival by Activation of Extracellular Signal-Regulated Kinase 1/2 and Akt Signaling Pathways," Diabetes, 2006, 55(9):2470-2478.
Xiaodong et al., "FGF21 Is Not a Major Mediator for Bone Homeostasis or Metabolic Actions of PPARα and PPARγ Agonists," J Bone Miner Res, 2017, 32(4):834-845.
Xu et al., "Downregulation of GLP-1 and GIP Receptor Expression by Hyperglycemia," Diabetes, 2007, 56(6):1551-58.
Xu et al., "Fibroblast Growth Factor 21 Reverses Hepatic Steatosis, Increases Energy Expenditure, and Improves Insulin Sensitivity in Diet-Induced Obese Mice," Diabetes, 2009, 58(1):250-259.
Yamamoto et al., "ATRP Synthesis of Thermally Responsive Molecular Brushes from Oligo(ethylene oxide) Methacrylates," Macromolecules, 2007, 40, 9348-9353.
Yang et al., "Long Term Exendin-4 Treatment Reduces Food Intake and Body Weight and Alters Expression of Brain Homeostatic and Reward Markers," Endocrinology, 2014, 155, 3473-3483.
Yusta et al., "GLP-1 receptor activation improves β cell function and survival following induction of endoplasmic reticulum stress," Cell Metab, 2006, 4(5):391-406.
Zhang et al., "In Depth Analysis on the Unusual Multistep Aggregation Process of Oligo(ethylene glycol) Methacrylate-Based Polymers in Water," Macromolecules, 2014, 47, 4728-4737.
Zununi Vahed et al., "Targeted cancer drug delivery with aptamer-functionalized polymeric nanoparticles," Journal of drug targeting, 2019, 27(3):292-299.
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
Park et al., "Protein stitchery: Design of a protein for selective binding to a specific DNA sequence," PNAS, 1992, vol. 89:9094-9096.
Olafsen et al., "Covalent disulfide-linked anti-CEA diabody allows site-specific conjugation and radiolabeling for tumor targeting applications," Protein Engineering, Design & Selection, 2004, 17(1):21-27.
Hu et al., "Nanografting De Novo Proteins onto Gold Surfaces," Langmuir, 2005, vol. 21:9103-9109.
McDaniel, "Assembly of Highly Asymmetric Genetically-Encoded Amphiphiles for Thermally Targeted Delivery of Therapeutics," Dissertation, 2013, 295 pages.
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
United States Patent Office Action for U.S. Appl. No. 16/058,924 dated Nov. 26, 2019 (23 pages).
AACR, "AACR Cancer Progress Report 2016," Clin Cancer Res, 2016, 22, 143 pages.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.

(56) References Cited

OTHER PUBLICATIONS

Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overcome the pathophysiological barriers of pancreatic cancer," Nat Rev Clin Oncol, 2016, 13, 750-765.
Aladini et al., "Chemical Synthesis and Characterization of Elastin-Like Polypeptides (ELPs) With Variable Guest Residues," J Pept Sci, 2016, 22(5):334-342.
Albanese et al., "The effect of nanoparticle size, shape, and surface chemistry on biological systems," Annu. Rev. Biomed. Eng., 2012, 14, 1-16.
Alconcel et al., "FDA-approved poly(ethylene glycol)—protein conjugate drugs," Polym. Chem. 2, 2011, 1442-1448.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, 2012, 13, 2645-2654.
Amiram et al., "A depot-forming glucagon-like peptide-1 fusion protein reduces blood glucose for five days with a single injection," J. Control. Release, 2013, 172, 144-151.
Amiram et al., "Injectable protease-operated depots of glucagon-like peptide-1 provide extended and tunable glucose control," Proc. Natl. Acad. Sci. 110, 2013, 2792-2797.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Antos et al., "Lipid Modification of Proteins through Sortase-Catalyzed Transpeptidation," J. Am. Chem. Soc. 2008, 130, 16338-16343.
Antos et al., "Site-Specific N- and C-Terminal Labeling of a Single Polypeptide Using Sortases of Different Specificity," J. Am. Chem. Soc. 2009, 131, 10800-10801.
Arias et al., "Superior preclinical efficacy of gemcitabine developed as chitosan nanoparticulate system," Biomacromolecules 2011, 12, 97-104.
Armstrong et al., "Antibody against poly(ethylene glycol) adversely affects PEG-asparaginase therapy in acute lymphoblastic leukemia patients," Cancer 110, 2007, 103-111.
Armstrong et al., "The Hydrodynamic Radii of Macromolecules and Their Effect on Red Blood Cell Aggregation," Biophys. J., 2004, 87, 4259-4270.
Arnida et al., "Geometry and surface characteristics of gold nanoparticles influence their biodistribution and uptake by macrophages," Eur J Pharm Biopharm, 2011, 77, 417-423.
Asai et al., "Protein polymer hydrogels by in situ, rapid and reversible self-gelation," Biomaterials, 2012, 33, 5451-5458.
Atun et al., "Expanding global access to radiotherapy," Lancet Oncol, 2015, 16, 1153-1186.
Averick et al., "ATRP under biologically relevant conditions: grafting from a protein," ACS Macro. Lett. 1, 2012, 6-10.
Averick et al., "Protein-polymer hybrids: conducting ARGET ATRP from a genetically encoded cleavable ATRP initiator," Eur. Polym. J. 49, 2013, 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, 2013, 34, 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-thug conjugates using unnatural amino acids," Proc Natl Acad Sci USA, 2012, 109(40):16101-16106.

Azhdarinia et al., "Regional radiochemotherapy using in situ hydrogel," PharmRes., 2005, 22, 776-783.
Bache et al., "Investigating the accuracy of microstereotactic-body-radiotherapy utilizing anatomically accurate 3D printed rodent-morphic dosimeters," Medical Physics, 2015, 42, 846-855.
Baggio et al., "A recombinant human glucagon-like peptide (GLP)-1-albumin protein (Albugon) mimics. peptidergic activation of GLP-1 receptor-dependent pathways coupled with satiety, gastrointestinal motility, and glucose homeostasis," Diabetes 53, 2004, 2492-2500.
Bailey et al., "Genomic analyses identify molecular subtypes of pancreatic cancer," Nature, 2016, 531, 47-52.
Bamford et al., "The COSMIC (Catalogue of Somatic Mutations in Cancer) database and website," British Journal of Cancer, 2004, 91, 355-358.
Banga et al., "Parenteral controlled delivery and parmacokinetics of therapeutic peptides and proteins," (CRC Press, Boca Raton, FL, 2005).
Banal et al., "PEGylation improves pharmacokinetic profile, liver uptake and efficacy of Interferon gamma in liver fibrosis," J. Control. Release 2011, 154, 233-240.
Barbuti et al., "Paclitaxel through the ages of anticancer therapy: Exploring its role in chemoresistance and radiation therapy," Cancers, 2015, 7, 2360-2371.
Barnett et al., "Normal tissue reactions to radiotherapy: towards tailoring treatment dose by genotype," Nat Rev Cancer, 2009, 9, 134-142.
Barton et al., "Estimating the demand for radiotherapy form the evidence: A review of changes from 2003 to 2012," Radiother Oncol, 2014, 112, 140-144.
Baskar et al., "Cancer and Radiation Therapy: Current Advances and Future Directions," Int. J. Med. Sci., 2012, 9, 193-199.
Bedford et al., "WW domain-mediated interactions reveal a spliceosome-associated protein that binds a third class of proline-rich motif: the proline glycine and methionine-rich motif," PNAS, 1998, 95: 10602-10607.
Begg et al., "Strategies to improve radiotherapy with targeted drugs," Nat Rev Cancer, 2011, 11, 239-253.
Bellucci et al., "A noncanonical function of sortase enables site-specific conjugation of small molecules to lysine residues inproteins," Angew. Chem. Int. Ed. 54, 2015, 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.
Bender et al., "Synthesis, Crystallization, and Biological Evaluation of an Orally Active Prodrug of Gemcitabine," J. Med. Chem. 2009, 52, 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, 2011, 50, 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, 2010, 142, 312-318.
Bhattacharyya et al., "A paclitaxel-loaded recombinant polypeptide nanoparticle outperforms Abraxane in multiple murine cancer models," Nat. Commun. 2015, 6, 7939.
Bidwell et al., "Development of elastin-like polypeptide for thermally targeted delivery of doxorubicin," Biochemical Pharmacology, 2007, 73(5):620-631.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.

(56) References Cited

OTHER PUBLICATIONS

Blasko et al., "Transperineal percutaneous iodine-125 implantation for prostatic carcinoma using transrectal ultrasound and template guidance," Endocurietherapy/Hyperthermia Oncology, 1987, 3, 131-139.

Bley et al., "Microtubule stabilising agents and ionising radiation: Multiple exploitable mechanisms for combined treatment," Eur J Cancer, 2013, 49, 245-253.

Bocci et al., "The pharmacological bases of the antiangiogenic activity of paclitaxel," Angiogenesis, 2013, 16, 481-492.

Bochicchio et al., "Investigating by CD the molecular mechanism of elasticity of elastomeric proteins," Chirality, 2008, 20, 985-994.

Boekhorst et al., "Genome-wide detection and analysis of cell wall-bound proteins with LPxTG-like sorting motifs," J. Bacteriol. 187, 2005, 4928-4934.

Boldt, "Use of albumin: an update," Br J. Anaesth, 2010, 104 (3), 276-284.

Bond, "Exenatide (Byetta) as a novel treatment option for type 2 diabetes mellitus," Proc. (Bayl. Univ. Med. Cent.) 19, 2006, 281-284.

Bontempo et al., "Streptavidin as a macroinitiator for polymerization: in situ protein-polymer conjugate formation," J. Am. Chem. Soc., 2005, 6508-6509.

Boyer et al., "Well-Defined Protein-Polymer Conjugates via in Situ RAFT Polymerization," J. Am. Chem. Soc. 2007, 129, 7145-7154.

Branco et al., "Self-assembling materials for therapeutic delivery," Acta Biomaterialia, 2009, 5(3): p. 817-831.

Broyer et al., "Emerging synthetic approaches for protein-polymer conjugations," Chem. Commun. 2011, 47, 2212.

Brusa et al., "Antitumor activity and pharmacokinetics of liposomes containing lipophilic gemcitabine prodrugs," Anticancer Res. 2007, 27, 195-199.

Burchard, "Light Scattering Techniques," Physical techniques for the study of food biopolymers, 1994, 151-213.

Burnouf, "Modern plasma fractionation," Transfus. Med. Rev., 2007, 21 (2), 101-117.

Cabral et al., "Accumulation of sub-100 nm polymeric micelles in poorly permeable tumours depends on size," Nature Nanotechnology, 2011, 6, 815-823.

Cai et al., "Long-acting preparations of exenatide," Drug Des. Dev. Ther. 7, 2013, 963-970.

Caliceti et al., "Pharmacokinetic and biodistribution properties of poly(ethylene glycol)-protein conjugates," Adv. Drug Deliv. Rev, 2003, 55, 1261-1277.

Callahan et al., "Triple stimulus-responsive polypeptide nanoparticles that enhance intratumoral spatial distribution," Nano Letters, 2012, 12, 2165-2170.

Camilloni et al., "Determination of secondary structure populations in disordered states of proteins using nuclear magnetic resonance chemical shifts," Biochemistry, 2012, 51, 2224-2231.

Campbell et al., "Pegylated peptides V. Carboxy-terminal PEGlyted analogs of growth hormone-releasing factor (GRF) display enhanced duration of biological activity invivo," J. Peptide Res., 1997, 49:527-537.

Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.

Cardenes et al., "Locally advanced pancreatic cancer: Current therapeutic approach," The Oncologist, 2006, 11, 612-623.

Carrico et al., "Introducing genetically encoded aldehydes into proteins," Nat Chem Biol, 2007, 3(6):321-322.

Cataldo et al., "Radiation-induced crosslinking of collagen gelatin into a stable hydrogel," Journal of Radioanalytical and Nuclear Chemistry, 2008, 275, 125-131.

Ceska et al., "A new and rapid method for the clinical determination of α-amylase activities in human serum and urine. Optimal conditions," Clinica Chimica Acta, 1969, 26, 437-444.

Chakrabartty et al., "Stability of α-Helices," Adv Protein Chem, 1995, 46, 141-176.

Chang et al., "Tumor-stroma interaction in orthotopic primary pancreatic cancer xenografts during hedgehog pathway inhibition," Int. J. Cancer, 2013, 133, 225-235.

Chaudhury et al., "The major histocompatibility complex-related Fc receptor for IgG (FcRn) binds albumin and prolongs its lifespan," J Exp Med, 2003, 197(3): p. 315-322.

Chen et al., "Anisotropic hydrogels fabricated with directional freezing and radiation-induced polymerization and crosslinking method," Materials Letters, 2012, 89, 104-107.

Chen et al., "Anti-hypervariable region antibody induced by a defined peptide: An approach for studying the structural correlates of idiotypes," PNAS, 1984, 81:1784-1788.

Chen et al., "Bioinspired Modular Synthesis of Elastin-Mimic Polymers to Probe the Mechanism of Elastin Elasticity," J. Am. Chem. Soc., 2009, 132(13):4577-4579.

Chen et al., "Rheology of Soft Materials," Annual Review of Condensed Matter Physics, 2010, 1, 301-322.

Chen et al., "Site-specific labeling of cell surface proteins with biophysical probes using biotin ligase," Nat Methods, 2005, 2(2):99-104.

Chen et al., "The use of self-adjuvanting nanofiber vaccines to elicit high-affinity B cell responses to peptide antigens without inflammation," Biomaterials 34, 2013, 8776-8785.

Chilkoti et al., "Design of thermally responsive, recombinant polypeptide carriers for targeted drug delivery," Advance Drug Delivery Reviews, 2002, 54:1093-1111.

Chilkoti et al., "Targeted drug delivery by thermally responsive polymers," Advanced Drug Delivery Reviews, 2002, 54:613-630.

Chithrani et al., "Determining the size and shape dependence of gold nanoparticle uptake into mammalian cells," Nano Lett, 2006, 6, 662-668.

Chitkara et al., "Self-Assembling, Amphiphilic Polymer—Gemcitabine Conjugate Shows Enhanced Antitumor Efficacy Against Human Pancreatic Adenocarcinoma," Bioconjug. Chem. 2013, 24, 1161-1173.

Cho et al., "Effects of hofmeister anions on the phase transition temperature of elastin-like polypeptides," J. Phys. Chem. B., 2008, 112, 13765-13771.

Cho et al., "Hydrogen bonding of β-turn structure is stabilized in D(2)O," J Am Chem Soc, 2009, 131, 15188-15193.

Cho et al., "Therapeutic nanoparticles for drug delivery in cancer," Clin. Cancer Res., 2008, 14, 1310-1316.

Choi et al., "Renal Clearance of Nanoparticles," Nature biotechnology, 2007, 25(10): p. 1165-1170.

Chow et al., "Peptide-based biopolymers in biomedicine and biotechnology," Mater. Sci. Eng. R Reports, 2008, 62, 125-155.

Chow et al., "Ultra-High Expression of a Thermally Responsive Recombinant Fusion Protein in E. coli," Biotechnology Progress, 2006, 22(3):638-646.

Choy et al., "Investigation of taxol as a potential radiation sensitizer," Cancer, 1993, 71, 3774-3778.

Christensen et al., "Fusion order controls expression level and activity of elastin-like polypeptide fusion proteins," Protein Science, 2009, 18:1377-1387.

Christensen et al., "Predicting Transition Temperatures of Elastin-Like Polypeptide Fusion Proteins," Biomacromolecules, 2013, 14(5): p. 1514-1519.

Cid-Arregui et al., "Perspectives in the treatment of pancreatic adenocarcinoma," World Journal of Gastroenterology, 2015, 21, 9297-9316.

Ciezki et al., "Brachytherapy or surgery? A composite view," Oncology, 2009, 23, 960-964.

Cima, "AVMA Guidelines for the Euthanasia of Animal: 2013 Edition," Journal of the American Veterinary Medical Association, 2013, 242, 102 pages.

Cirulis et al., "Viscoelastic properties and gelation of an elastin-like polypeptide," Journal of Rheology, 2009, 53, 1215-1228.

Clarke et al., "Tropoelastin massively associates during coacervation to form quantized protein spheres," Biochemistry, 2006, 45, 9989-9996.

Clavé et al., "Amylase, lipase, pancreatic isoamylase, and phospholipase A in diagnosis of acute pancreatitis," Clinical Chemistry, 1995, 41, 1129-1134.

(56) References Cited

OTHER PUBLICATIONS

Coin et al., "Solid-phase peptide synthesis: from standard procedures to the synthesis of difficult sequences," Nat. Protoc., 2007, 2, 3247.
Colomb et al., "Radiation-Convertible Polymers from Norbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, 2011, 9, 22-31.
Craik et al., "The future of peptide-based drugs," Chemical biology & drug design 81, 2013, 136-147.
Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalla Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.
Darzynkiewicz et al., "DNA content measurement for DNA ploidy and cell cycle analysis," Current Protocols in Cytometry, 2001, 7.5.1-7.5.24.
Dasgupta et al., "Isopeptide Ligation Catalyzed by Quintessential Sortase a: Mechanistic Cues From Cyclic and Branched Oligomers of Indolicidin," The Journal of Biological Chemistry, 2011, vol. 286, No. 27, pp. 23996-24006, Supplemental Information.
De et al., "Temperature-Regulated Activity of Responsive Polymer-Protein Conjugates Prepared by Grafting-from via RAFT Polymerization," J. Am. Chem. Soc. 2008, 130, 11288-11289.
De Simone et al., "Accurate random coil chemical shifts from an analysis of loop regions in native states of proteins," J Am Chem Soc, 2009, 131, 16332-16333.
Deer et al., "Phenotype and genotype of pancreatic cancer cell lines," Pancreas, 2010, 39, 425-435.
Dejana et al., "The role of adherens junctions and VE-cadherin in the control of vascular permeability," J Cell Sci, 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. 2009, 5, 560-569.
Deshayes et al., "Radium 223 dichloride for prostate cancer treatment," Drug Des Devel Ther, 2017, 11, 2643-2651.
Diana et al., "Prognostic role and correlation of CA9, CD31, CD68 and CD20 with the desmoplastic stroma in pancreatic ductal adenocarcinoma," Oncotarget, 2016, 7, 72819-72832.
Diehl et al., "A Good Practice Guide to the Administration of Substances and Removal of Blood Including Routes and Volumes," J Appl Toxicol, 2001, 21, 15-23.
Ding et al., "Mechanism for the alpha-helix to beta-hairpin transition," Proteins, 2003, 53, 220-228.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.

Dreher et al., "Temperature triggered self-assembly of polypeptides into multivalent spherical micelles," J. Am. Chem. Soc. 2008, 130, 687-694.
Dreher et al., "Thermal cycling enhances the accumulation of a temperature-sensitive biopolymer in solid tumors," Cancer Res, 2007, 67, 4418-4424.
Dreher, M. R. PhD. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., 2007, 341, 207-214.
Drucker et al., "The incretin system: glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Du et al., "Endoscope-assisted brachytherapy for pancreatic cancer: From tumor killing to pain relief and drainage," Journal of interventional gastroenterology, 2011, 1, 23-27.
Du et al., "Tailor-made dual pH-sensitive polymer-doxorubicin nanoparticles for efficient anticancer drug delivery," J. Am. Chem. Soc., 2011, 133, 17560-17563.
Duan et al., "Fibronectin type III domain based monobody with high activity," Biochemistry, 2007 46(44):12656-12664.
Dubey et al., "Development and evaluation of folate functionalized albumin nanoparticles for targeted delivery of gemcitabine," Int J Pharm., 2015, 492(1-2):80-91.
Ducreux et al., "Radiation plus docetaxel and cisplatin in locally advanced pancreatic carcinoma: A non-comparative randomized phase II trial," Digestive and Liver Disease, 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised Recist guideline (version 1.1)," Eur J Cancer, 2017, 45, 228-247.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) invitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Feng et al., "Protein resistant surfaces: comparison of acrylate graft polymers bearing oligo-ethylene oxide and phosphorylcholine side chains," Biointerphases, 2006, 1 (1), 50.
Fernandez-Colino et al., "Amphiphilic Elastin-Like Block Co-Recombinamers Containing Leucine Zippers: Cooperative Interplay

(56) References Cited

OTHER PUBLICATIONS between Both Domains Results in Injectable and Stable Hydrogels," Biomacromolecules, 2015, 16, 3389-3398.
Fluegel et al., "Chain stiffness of elastin-like polypeptides," Biomacromolecules 2010, 11, 3216-3218.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.
Friedman et al., "Directed Evolution to Low Nano molar Affinity of a Tumor-Targeting Epidermal Growth Factor Receptor-Binding Affibody Molecule," J. Mol. Biol., 2008, 376, 1388-1402.
Frilling et al., "Recommendations for management of patients with neuroendocrine liver metastases," The lancet oncology, 2014, 15, e8-21.
Fu et al., Recent Patents on Anti-Cancer Drug Discovery, 2009. 4(3): p. 262-272.
Fujiwara et al., "Modulating effect of the PI3-kinase inhibitor LY294002 on cisplatin in human pancreatic cancer cells," Journal of Experimental & Clinical Cancer Research, 2008, 27, 76.
Furgeson et al., "Structural optimization of a "smart" doxorubicin-polypeptide conjugate for thermally targeted delivery to solid tumors," Journal of Controlled Release, 2006, 110:362-369.
Furumoto et al., "Effect of coupling of albumin onto surface of PEG liposome on its in vivo disposition," International Journal of Pharmaceutics, 2007, 329(1-2): p. 110-116.
Gaberc-Porekar et al., "Obstacles and pitfalls in the PEGylation of therapeutic proteins," Curr. Opin. Drug Discov. Devel. 11, 2008, 242-250.
Gabizon et al., "Prolonged circulation time and enhanced accumulation in malignant exudates of doxorubicin encapsulated in polyethylene-glycol coated liposomes," Cancer Res. 1994, 54, 987-992.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009, 15231-15236.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and inpatients treated with PEG-conjugated agents," Expert Opinion. Drug Deliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (2017).
Ghoorchian et al., "Molecular architecture influences the thermally induced aggregation behavior of elastin-like polypeptides," Biomacromolecules, 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.

Giberti et al., "Radical retropubic prostatectomy versus brachytherapy for low-risk prostatic cancer: a prospective study," World J Urol, 2009, 27, 607-612.
Gibson et al., "Enzymatic assembly of DNA molecules up to several hundred kilobases," Nat Methods, 2009, 6, 343-345.
Glassman et al., "Toughening of Thermoresponsive Arrested Networks of Elastin-Like Polypeptides to Engineer Cytocompatible Tissue Scaffolds," Biomacromolecules, 2016, 17, 415-426.
Gluck et al., "Single Vector System for Efficient N-myristoylation of Recombinant Proteins in E. coli," Plos One. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling Fundam," Clin. Pharmacol. 22, 2008, 633-648.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin, 2003, 31(3): 529-540.
Greenfield, "Using circular dichroism spectra to estimate protein secondary structure," Nat. Protoc., 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Güngör et al., "Pancreatic cancer," British Journal of Pharmacology, 2014, 171, 849-858.
Guo et al., "Nanoparticles escaping RES and endosome: challenges for siRNA delivery for cancer therapy," J. Nanomaterials, 2011, 2011: 1-12.
Gustafsson, "Nonlinear structured-illumination microscopy: wide-field fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.
Haider et al., "Genetically engineered polymers: Status and prospects for controlled release," J. Control. Release, 2004, 95, 1-26.
Halozyme Therapeutics, "PEGPH2O Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, 2013, vol. 4, Article 331, 7 pages.
Hamidi et al., "Pharmacokinetic Consequences of Pegylation," Drug Deliv. 2006, 13, 399-409.
Hamley, "Self-assembly of amphiphilic peptides," Soft Matter, 2011, 7, 4122.

(56) References Cited

OTHER PUBLICATIONS

Han et al., "Survival of patients with advanced pancreatic cancer after iodine[125] seeds implantation brachytherapy: A meta-analysis," Medicine, 2017, 96, e5719.
Harmon et al., "A Model for Hysteresis Observed in Phase Transitions of Thermally Responsive Intrinsically Disordered Protein Polymers," Biophysical Journal, 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, 2015, 48, 4183-4195.
Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.
Hassouneh et al., "Fusions of elastin-like polypeptides to pharmaceutical proteins," Methods Enzymol., 2012, 502, 215-37.
Hassouneh et al., "Unexpected Multivalent Display of Proteins by Temperature Triggered Self-assembly of Elastin-like Polypeptide Block Copolymers," Biomacromolecules, 2012, vol. 13, Issue 4, pp. 1598-1605.
Hathout et al., "Analysis of seed loss and pulmonary seed migration inpatients treated with virtual needle guidance and robotic seed delivery," American journal of clinical oncology, 2011, 34, 449-453.
He et al., "Comparative genomics of elastin: Sequence analysis of a highly repetitive protein," Matrix Biology, 2007, 26:524-540.
He et al., "Improving protein resistance of α-Al2O3 membranes by modification with POEGMA brushes," Applied Surface Science, 2011, 258 (3), 1038-1044.
Heagerty et al., Biometrics, "Time-dependent ROC curves for censored survival data and a diagnostic marker," 2000, 56(2):337-44.
Heal et al., "N-Myristoyl transferase-mediated protein labelling in vivo," Org. Biomol. Chain, 2008, 6(13):2308-2315.
Heal et al., "Site-specific N-terminal labelling of proteins in vitro and in vivo using N-myristoyl transferase and bioorthogonal ligation chemistry," Chem. Commun., 2008, 3, 480-482.
Heredia et al., "In Situ Preparation of Protein-"Smart" Polymer Conjugates with Retention of Bioactivity," J. Am. Chem. Soc. 2005, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, 2014, R63.
Hidalgo, "Pancreatic Cancer," N Engl J Med, 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, 2016, 22, 2848-2854.
Ho et al., "Chemoenzymatic Labeling of Proteins for Imaging in Bacterial Cells," J. Am. Chem. Soc., 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, 2007, pp. 40-47.
Hochkoeppler, "Expanding the landscape of recombinant protein production in *Escherichia coli*," Biotechnol. Lett., 2013, 35, 1971-1981.
Holehouse et al., "CIDER: Classification of Intrinsically Disordered Ensemble Regions," Biophysical Journal, 2015, vol. 108, Issue 2, Supplement 1, p. 228a.

Holm et al., "Transperineal [125]iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011, 42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.
Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Ito et al., "In vivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-1uc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.
Jia et al., "Preparation, physicochemical characterization and cytotoxicity in vitro of gemcitabine-loaded PEG-PDLLA nanovesicles," World J. Gastroenterol. 2010, 16(8):1008-1013.

(56) References Cited

OTHER PUBLICATIONS

Jiang et al., "The internal structure of self-assembled peptide amphiphiles nanofibers," Soft Matter, 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Jonsson et al., "Engineering of a femtomolar affinity binding protein to human serum albumin," Protein Engineering Design and Selection, 2008, 21(8): 515-527.
Junutula et al., "Site-specific conjugation of a cytotoxic drug to an antibody improves the therapeutic index," Nat Biotechnol, 2008, 26(8):925-932.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanoski et al., "The role of nausea in food intake and body weight suppression by peripheral GLP-1 receptor agonists, exendin-4 and liraglutide," Neuropharmacology 62, 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version 2.5 <http://rsb.info.nih.gov/ij/plugins/fraclac/FLHelp/Introduction.htm> 1999-2012.
Katakura, "Nuclear Data Sheets for A = 125," Nuclear Data Sheets, 2011, 112, 495-705.
Kato et al., "Acidic extracellular microenvironment and cancer," Cancer Cell Int, 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, 2012, 4(1):59-63.
Keller et al., "Empirical Statistical Model to Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Keten et al., "Nanoconfinement controls stiffness, strength and mechanical toughness of β-sheet crystals in silk," Nat Mater, 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., 2006, 24, 1065-1066.
Khazov et al., "Nuclear Data Sheets for A=131," Nuclear Data Sheets, 2006, 107, 2715-2930.
Kim et al., "Recombinant elastin-mimetic biomaterials: Emerging applications in medicine," Adv Drug Deliv Rev, 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem. 2012, 23, 2214-2220.
Kim et al., "Ultrasensitive Carbon nanotube-based biosensors using antibody-binding fragments," Analytical Biochemistry, 2008, 381, 193-198.
Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using a Sortase-Mediated Protein Ligation Method," J Biomol NMR. Mar. 2009, vol. 43, No. 3; pp. 145-150.
Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, 2012, 41(7):2686-2695.
Koong et al., "Phase II study to assess the efficacy of conventionally fractionated radiotherapy followed by a stereotactic radiosurgery boost inpatients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., 2015, 26(10):2153-2160.
Kulkarni et al., "Selective functionalization of the protein N terminus with N-myristoyl transferase for biocmijugation in cell lysate," ChemBioChem, 2013, 14, 1958-1962.
Kumar et al., "N-Terminal Region of the Catalytic Domain of Human N-Myristoyltransferase 1 Acts as an Inhibitory Module," PLoS One, 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Le Droumaguet et al., "Recent advances in the design of biocoiljugates from controlled/living radical polymerization," Polym. Chem. 2010, 1, 563-598.
Le Meins et al., "Hybrid polymer/lipid vesicles: State of the art and future perspectives," Mater. Today, 2013, 16, 397-402.
Leader et al., "Protein therapeutics: a summary and pharmacological classification," Nat. Rev. Drug Discov. 7, 2008, 21-39.

(56) References Cited

OTHER PUBLICATIONS

Lee et al., "Atomistic molecular dynamics simulations of peptide amphiphile self-assembly into cylindrical nanofibers," J. Am. Chem. Soc., 2011, 133, 3677-3683.

Lee et al., "Immunohistochemical analysis of claudin expression in pancreatic cystic tumors," Oncology Reports, 2011, 25(4): 971-978.

Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.

Lee et al., "Mechanical properties of cross-linked syntheti elastomeric polypentapeptides," Macromolecules, 2001, 34, 5968-5974.

Lee et al., "Phase transition and elasticity of protein-based hydrogels," J. Biomater. Sci. Polymer Edn, 2001, 12, 229-242.

Lee et al., "Theranostic nanoparticles with controlled release of gemcitabine for targeted therapy and MRI of pancreatic cancer," ACS Nano 2013, 7(3):2078-2089.

Lele et al., "Synthesis of uniform protein-polymer conjugates," Biomacromolecules 6, 2005, 3380-3387.

Lennen et al., "Membrane Stresses Induced by Overproduction of Free Fatty Acids in *Escherichia coli*," Appl Environ Microb., 2011, 77(22):8114-28.

Leung et al., "Bio-Click Chemistry: Enzymatic Functionalization of PEGylated Capsules for Targeting Applications**," Angew. Chem. Int. Ed. 2012, 51, 7132-7136.

Le Vine et al., "Thioflavine T interaction with synthetic Alzheimer's disease beta-amyloid peptides: detection of amyloid aggregation in solution," Protein Sci., 1993, 2, 404-10.

Levy et al., "Novel Exenatide Analogs with Peptidic Albumin Binding Domains: Potent Anti-Diabetic Agents with Extended Duration of Action," PLoS ONE, 2014, 9(2): e87704, 9 pages.

Li et al., "Elastin is an essential determinant of arterial morphogenesis," Nature, 1998, 393, 276-280.

Li et al., "Molecular description of the LCST behavior of an elastin-like polypeptide," Biomacromolecules, 2014, 15, 3522-3530.

Li et al., "Nanoparticles Evading the Reticuloendothelial System: Role of the Supported Bilayer," Biochim. Biophys. Acta, 2009, 1788 (10), 2259-2266.

Li et al., "Pancreatic cancer," Lancet, 2004, 363, 1049-1057.

Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.

Li et al., "Temperature-Triggered Phase Separation of a Hydrophilic Resilin-Like Polypeptide," Macramol. Rapid Commun, 2015, 36(1):90-95.

Liao et al., "Removal of N-terminal methionine from recombinant proteins by engineered *E. coli* methionine aminopeptidase," Prot. Sci. 13, 2004, 1802-1810.

Liechty et al., "Polymers for Drug Delivery Systems," Annual review of chemical and biomolecular engineering 2010, 1:149-173.

Lillie et al., "The viscoelastic basis for the tensile strength of elastin," Int J Biol Macromol, 2002, 30, 119-127.

Lim et al., "Improved Non-Chromatographic Purification of a Recombinant Protein by Cationic Elastin-like Polypeptides" Biomacromolecules, 2007, 8(5): 1417-1424.

Lim et al., "In situ cross-linking of elastin-like polypeptide block copolymers for tissue repair," Biomacromolecules, 2008, 9, 222-230.

Lim et al., "In vivo post-translational modifications of recombinant mussel adhesive protein in insect cells," Biotechnol. Prog., 2011, 27, 1390-1396.

Lin et al., "Utility of immunohistochemistry in the pancreatobiliary tract," Arch Pathol Lab Med, 2015, 139, 24-38.

Linder et al., "Lipid Modifications of G Protein Subunits," J. Biol. Chem., 1991, 266(7):4654-4659.

Ling et al., "Protein thioester synthesis enabled by sortase," J. Am Chem Soc, 2012, 134(26):10749-10752.

Litiere et al., "RECIST—learning from the past to build the future," Nat Rev Clin Oncol, 2017, 14, 187-192.

Liu et al., "Brachytherapy using injectable seeds that are self-assembled from genetically encoded polypeptides in situ," Cancer Res, 2012, 72, 5956-5965.

Liu et al., "Hydrophobic modifications of cationic polymers for gene delivery," Prog. In Polym. Sci., 2010, 35, 1144-1162.

Liu et al., "In Situ Formation of Protein-Polymer Conjugates through Reversible Addition Fragmentation Chain Transfer Polymerization**," Angew. Chem. Int. Ed. 2007, 46, 3099-3103.

Liu et al., "Injectable intratumoral depot of thermally responsive polypeptide-radionuclide conjugates delays tumor progression in a mouse model," J. Control Release, 2010, 144(1):2-9.

Liu et al., "Tracking the in vivo fate of recombinant polypeptides by isotopic labeling" Journal of Controlled Release, 2006, 114, 184-192.

Liu et al., "Tumor accumulation, degradation and pharmacokinetics of elastin-like polypeptides in nude mice," Journal of Controlled Release, 2006, 116, 170-178.

Livingstone, "Theoretical property predictions. Curr Top Med Chem FIELD Full Journal Title: Current topics in medicinal chemistry," Curr. Top. Med. Chem. 2003, 3, 1171-1192.

Lovshin et al., "Incretin-based therapies for type 2 diabetes mellitus," Nat. Rev. Endocrinol. 5, 2009, 262-269.

Ludden, "Nonlinear pharmacokinetics: clinical Implications," Clin. Pharmacokinet., 1991, 20 (6), 429-446.

Luginbuhl et al., "One-week glucose control via zero-order release kinetics from an injectable depot of glucagon-like peptide-1 fused to a thermosensitive biopolymer," Nat. Biomed. Eng., 2017, 1, 0078.

Luginbuhl et al., "Recombinant Synthesis of Hybrid Lipid-Peptide Polymer Fusions that Self-Assemble and Encapsulate Hydrophobic Drugs," Angew Chem Int Ed Engl., 2017, 56: 13979-13984.

Lukyanov et al., "Micelles From Lipid Derivatives of Water-Soluble Polymers as Delivery Systems for Poorly Soluble Drugs," Adv. Drug Deliver. Rev., 2004, 56(9):1273-1289.

Lund et al., "Phase II study of gemcitabine (2',2'-difluorodeoxycytidine) in previously treated ovarian cancer patients," J. Natl. Cancer. Inst 1994, 86(20):1530-1533.

Luo et al., "Noncovalent Modulation of the Inverse Temperature Transition and Self-Assembly of Elastin-b-Collagen-like Peptide Biocoiljugates," J Am Chem Soc, 2015, 137, 15362-15365.

Ma et al., "Non-fouling oligo(ethylene glycol)-functionalized polymer brushes synthesized by surface-initiated atom transfer radical polymerization," Advanced Materials 2004, 16 (4), 338.

Ma et al., "Protein-resistant polymer coatings on silicon oxide by surface-initiated atom transfer radical polymerization," Langmuir: the ACS journal of surfaces and colloids, 2006, 22 (8), 3751-6.

Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.

MacEwan et al., "Applications of elastin-like polypeptides in drug delivery," Journal of Controlled Release, 2014, 190: p. 314-330.

MacEwan et al., "Controlled apoptosis by a thermally toggled nanoscale amplifier of cellular uptake," Nano Letters, 2014, 14, 2058-2064.

MacEwan et al., "Digital switching of local arginine density in a genetically encoded self-assembled polypeptide nanoparticle controls cellular uptake," Nano Lett., 2012, 12, 3322-3328.

MacEwan et al., "Elastin-like polypeptides: Biomedical applications of tunable biopolymers," Biopolymers, 2010, 94, 60-77.

MacEwan et al., "Non-chromatographic Purification of Recombinant Elastin-like Polypeptides and their Fusions with Peptides and Proteins from *Escherichia coli*," 2014, 88, p. e51583.

MacEwan et al., "Phase Behavior and Self-Assembly of Perfectly Sequence-Defined and Monodisperse Multiblock Copolypeptides," Biomacromolecules, 2017, 18(2):599-609.

Mack et al., "Antiobesity action of peripheral exenatide (exendin-4) in rodents: effects on food intake, body weight, metabolic status and side-effect measures," Int. J. Obes. 30, 2006, 1332-1340.

(56) References Cited

OTHER PUBLICATIONS

MacKay et al., "Self-assembling chimeric polypeptide-doxorubicin conjugate nanoparticles the abolish tumors after single injection," Nat Mater, 2009, 8(12):993-999.

Maeda et al., "Tumor vascular permeability and the EPR effect in macro molecular therapeutics: a review," J. Control. Release, 2000, 65(1-2)271-284.

Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, 2010, 671-678.

Maitra et al., "Pancreatic Cancer," Annu Rev Pathol Mech Dis, 2008, 3, 157-188.

Malik et al., "Recent advances in protein and peptide drug delivery systems," Curr. Drug Deliv. 2, 2007, 141-151.

Mann et al., "Proteomic analysis of post-translational modifications," Nat. Biotechnol., 2003, 21, 255-61.

Manzoor et al., "Overcoming limitations in nanoparticle drug delivery: triggered, intravascular release to improve drug penetration into tumors," Cancer Res, 2012, 72, 5566-5575.

Mao et al., "DNA repair by nonhomologous end joining and homologous recombination during cell cycle in human cells," Cell cycle, 2008, 7, 2902-2906.

Mao et al., "Sortase-mediated protein ligation: a new method for protein engineering," J. Am. Chem. Soc., 2004, 126(9):2670-2671.

Maraffini et al., "Sortases and the art of anchoring proteins to the envelopes of Gram-positive bacteria," Microbiol Mol Biol Rev, 2006, 70(1):192-221.

Mariam et al., "Albumin corona on nanoparticles—a strategic approach in drug delivery," Drug Deliv., 2016, 23 (8), 2668-2676.

Marr et al., "Effect of Temperature on the Composition of Fatty Acids in *Escherichia coli*," J Bacteriol., 1962, 84(6):1260-7.

Marten et al., "A randomized multicentre phase II trial comparing adjuvant therapy inpatients with interferon alpha-2b and 5-FU alone or in combination with either external radiation treatment and cisplatin (CapRI) or radiation alone regarding event-free survival—CapRI-2," BMC Cancer, 2009, 9, 1-8.

Maskarinec et al., "Protein engineering approaches to biomaterials design," Curr. Opin. Biotechnol., 2005, 16, 422-426.

Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.

Mastria et al., "Doxorubicin-conjugated polypeptide nanoparticles inhibit metastasis in two murine models of carcinoma," J Control Release, 2015, 208:52-8.

Matsumura et al., "A new concept for macromolecular therapeutics in cancer chemotherapy: mechanism of tumoritropic accumulation of proteins and the antitumor agent smancs," Cancer Res. 1986, 46, 6387-6392.

Matsumura, "Cancer stromal targeting (CAST) therapy," Advanced Drug Delivery Reviews, 2012, 64, 710-719.

Matyjaszewski et al., "Atom transfer radical polymerization," Chem. Rev. 101, 2001, 2921-2990.

Matyjaszewski et al., "Macromolecular engineering by atom transfer radical polymerization," J. Am. Chem. Soc. 136, 2014, 6513-6533.

Maurer-Stroh et al., "N-terminal N-myristoylation of proteins: prediction of substrate proteins from amino acid sequence" J Mol Biol., 2002, 317(4):541-557.

Maurer-Stroh et al., "N-terminal N-myristoylation of proteins: Refinement of the sequence motif and its taxon-specific differences," J Mol Biol., 2002, 317(4):523-540.

Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.

McConkey et al., "Molecular Characterization of Pancreatic Cancer Cell Lines," Pancreatic Cancer, 2010, 457-469.

McDaniel et al., "A unified model for de novo design of elastin-like polypeptides with tunable inverse transition temperatures," Biomacromolecules, 2013, 14(8):2866-2872.

McDaniel et al., "Actively targeting solid tumours with thermoresponsive drug delivery systems that respond to mild hyperthermia," Int J Hyperthermia, 2013, 29, 501-510.

McDaniel et al., "Doxorubicin-conjugated chimeric polypeptide nanoparticles that respond to mild hyperthermia," Control. Release, 2012, 159 (3), 362-367.

McDaniel et al., "Drug delivery to solid tumors by elastin-like polypeptides," Adc. Drug Deliver. Rev., 2010, 62(15):1456-1467.

McDaniel et al., "Noncanonical Self-Assembly of Highly Asymmetric Genetically Encoded Polypeptide Amphiphiles into Cylindrical Micelles," Nano Lett, 2014, 14(11):6590-6598.

McDaniel et al., "Rational design of "heat seeking" drug loaded polypeptide nanoparticles that thermally target solid tumors," Nano Letters, 2014, 14, 2890-2895.

McDaniel et al., "Self-assembly of thermally responsive nanoparticles of a genetically encoded peptide polymer by drug conjugation," Chem. Int. Ed. 2013, 52, 1683-1687.

McDaniel et al., "Recursive Directional Ligation by Plasmid Reconstruction Allows Rapid and Seamless Cloning of Oligomeric Genes," Biomacromolecules, 2010, 11(4):944-952.

McHale et al., "Synthesis and in vitro evaluation of enzymatically cross-linked elastin-like polypeptide gels for cartilaginous tissue repair," Tissue Eng, 2005, 11, 1768-1779.

McIlhinney et al., "Characterization of a polyhistidine-tagged form of human myristoyl-CoA: protein N-myristoyltransferase produced in *Escherichia coli*," European Journal of Biochemistry, 1994, 222(1):137-146.

Mejuch et al., "Synthesis of lipidated proteins," Bioconjug. Chem. 27, 2016, 1771-1783.

Mero et al., "Transglutaminase-mediated PEGylation of proteins: direct identification of the sites protein medification by mass spectrometry using a novel monodisperse PEG," Bioconjug Chem, 2009, 20(2):384-389.

Merrick et al., "Seed fixity in the prostate/periprostatic region following brachytherapy," International journal of radiation oncology, biology, physics, 2000, 46, 215-220.

Methods and Welfare Considerations in Behavioral Research with Animal. (2002).

Meyer et al., "Drug targeting using thermally responsive polymers and local hyperthermia," Journal of Controlled Release, 2001, 74, 213-224.

Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.

Meyer et al., "Purification of recombinant proteins by fusion with thermally-responsive polypeptide," Nat. Biotechnol., 1999, 17(11):1112-1115.

Meyer et al., "Quantification of the effects of chain length and concentration on the thermal behavior of elastin-like polypeptides," Biomacromolecules, 2004, 5(3):846-51.

Meyer et al., "Targeting a Genetically Engineered Elastin-Like Polypeptide to Solid Tumors by Local Hyperthermia," Cancer Res., 2001, 61(4):1548-1554.

Miao et al., "Sequence and domain arrangements influence mechanical properties of elastin-like polymeric elastomers," Biopolymers, 2013, 99, 392-407.

Miao et al., "Structural determinants of cross-linking and hydrophobic domains for self-assembly of elastin-like polypeptides," Biochemistry, 2005, 44, 14367-14375.

Michl et al., "Current concepts and novel targets in advanced pancreatic cancer," Gut, 2013, 62, 317-326.

Micsonai et al. "Accurate secondary structure prediction and fold recognition for circular dichroism spectroscopy," Proc Natl Acad Sci U S A, 2015, 112, E3095-3103.

Milenic et al., "Antibody-targeted radiation cancer therapy," Nature Reviews Drug Discovery, 2004, 3, 488-498.

(56) References Cited

OTHER PUBLICATIONS

Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Mosbach et al., "Formation of proinsulinby immobilized Bacillus subtilis," Nature, 1983, 302, 543-545.
Muiznieks et al., "Structural changes and facilitated association of tropoelastin," Archives of Biochemistry and Biophysics, 2003, 410, 317-323.
Muiznies et al., "Modulated growth, stability and interactions of liquid-like coacervate assemblies of elastin," Matrix Biology 36, 2014, pp. 39-50.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, 2006, vol. 3, No. 6, pp. 429-438.
Murphy et al., "A dosimetric model of duodenal toxicity after stereotactic body radiotherapy for pancreatic cancer," Int J Radiation Oncology Biol Phys, 2010, 78, 1420-1426.
Na et al., "Thermoresponsive pore structure of biopolymer microspheres for a smart drug carrier," Langmuir, 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials 2014, 35(24):6482-6497.
Nairn et al., "A Synthetic Resilin Is Largely Unstructured," Biophysical Journal, 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, 2010, 62, 1479-1485.
Nettles et al., "In situ crosslinking elastin-like polypeptide gels for application to articular cartilage repair in a goat osteochondral defect model," Tissue Eng Part A, 2008, 14, 1133-1140.
Newcomb et al., "Advances in cryogenic transmission electron microscopy for the characterization of dynamic self-assembling nanostructures," Current Opinion in Colloid and Interface Science, 2012, 17, 350-359.
Newton et al., "Commissioning a small-field biological irradiator using point, 2D, and 3D dosimetry techniques," Medical Physics, 2011, 38, 6754-6762.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. 2006, 45, 4697-4699.
Nie, "Understanding and overcoming major barriers in cancer nanomedicine," Nanomedicine (Lond) 2010, 5 (4), 523-528.
Nielsen, "Incretin mimetics and DPP-IV inhibitors for the treatment of type 2 diabetes," Drug Discov. Today 10, 2005, 703-710.
Nilvebrant et al., "The albumin-binding domain as a scaffold for protein engineering," Computational and Structural Biotechnology Journal, 2013, 6: e201303009, 8 pages.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, 2008, 9, 2755-2763.
O'Day et al., "Therapeutic Protein-polymer Conjugates: Advancing beyond PEGylation," J. Am. Chem. Soc., 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Ortony et al., "Internal dynamics of a supramolecular nanofibre," Nat. Mater., 2014, 13, 1-5.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, 2010, 102, 456-463.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, 2016, 96, S204-S205.
Palva et al., "Secretion of interferon by Bacillus subtilis," Gene, 1983, 22, 229-235.
Paolino et al., "Folate-targeted supramolecular vesicular aggregates as a new frontier for effective anticancer treatment in invivo model," Eur. J. Pharm. Biopharm. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release 2010, 144(2):144-150.
Paoloni et al., "Translation of new cancer treatments from pet dogs to humans," Nat. Rev. Cancer 2008, 8 (2), 147-156.
Papa et al., "PEGylated Liposomal Gemcitabine: Insights Into a Potential Breast Cancer Therapeutic," Cell Oncol. (Dordr) 2013, 36(6):449-457.
Paramonov et al., "Self-assembly of peptide-amphiphile nanofibers: the roles of hydrogen bonding and amphiphilic packing," J. Am. Chem. Soc., 2006, 128, 7291-7298.
Park et al., "Formulation optimization and in vivo proof-of-concept study of thermosensitive liposomes balanced by phospholipid, elastin-like polypeptide, and cholesterol," PLoS One, 2014, 9: e103116, 13 pages.
Parkes et al. "Discovery and development of exenatide: the first antidiabetic agent to leverage the multiple benefits of the incretin hormone, GLP-1," Expert Opinion. Drug Deliv. 8, 2012, 219-244.
Parveen et al., "Nanomedicine," Clinical Pharmacokinetics, 2006, 45(10):965-988.
Patil et al., "Cellular delivery of doxorubicin via pH-controlled hydrazone linkage using multifunctional nano vehicle based on poly(beta-1-malic acid)," Int J Mol Sci, 2012, 13, 11681-11693.
Peeler et al., "Genetically encoded initiator for polymer growth from proteins," J. Am. Chem. Soc. 132, 2010, 13575-13577.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., 2017, 28(5):1403-1412.
Phan et al., "Temperature-responsive self-assembly of charged and uncharged hydroxyethylcellulose-graft-poly(N-isopropylacrylamide) copolymer in aqueous solution," Colloid Polym. Sci., 2011, 289 (9), 993-1003.
Pinkas et al., "Tunable, post-translational hydroxylation of collagen domains in *Escherichia coli*," ACS Chem. Biol., 2011, 6, 320-324.
Pliarchopoulou et al., "Pancreatic cancer: Current and future treatment strategies," Cancer Treatment Reviews, 2009, 35, 431-436.

(56) References Cited

OTHER PUBLICATIONS

Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve the Properties of Cytokines," PNAS, 2011, vol. 108, No. 8, pp. 3169-3174.
Potters et al., "12-year outcomes following permanent prostate brachytherapy inpatients with clinically localized prostate cancer," the Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21, 418-429.
Provenzano et al., "Hyaluronan, fluid pressure, and stromal resistance in pancreas cancer," Br J Cancer, 2013, 108, 1-8.
Pulaski et al., "Mouse 4T1 breast tumor model," Curr. Protoc. Immunol., 2001, Chapter 20, Unit 20.2.
Qi et al., Dataset for a brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: a biomedical perspective," Polym. Chem. 5, 2014, 266-276.
Qi et al., "Protein-polymer conjugation—moving beyond PEGylation," Curr. Opin. Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Development of Orthotopic Pancreatic Tumor Mouse Models," Methods Mol Biol, 2013, 980: 215-223.
Qiu et al., "Polymer Architecture and Drug Delivery," Pharmaceutical Research, 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Sequence heuristics to encode phase behaviour in intrinsically disordered protein polymers," Nat. Mater., 2015, 14, 1164-1171.
Rabotyagova et al., "Protein-based block copolymers," Biomacromolecules, 2011, 12, 269-289.
Radivojac et al., "Intrinsic Disorder and Functional Proteomics," Biophysical Journal, 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a B xPC3 human pancreatic cancer xenograft model," Cancer Research, 2016, 76.
Rankine et al., "Investigating end-to-end accuracy of image guided radiation treatment delivery using a micro-irradiator," Physics in Medicine and Biology, 2013, 58, 7791-7801.

Rao et al., "Synthetic nanoparticles camouflaged with biometric erythrocyte membranes for reduced reticuloendothelial system uptake," Nanotechnology, 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Rauscher et al. "Proline and Glycine Control Protein Self-Organization into Elastomeric or Amyloid Fibrils," Structure, 2006, 14:1667-1676.
Regier et al., American Heart Association 2014 Scientific Sessions, 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Engineered fibronectin type III domain with a RGDWE sequence binds with enhanced affinity and specificity to human av$\beta$3 integrin," J Mol Biol, 2003, 326(5):1475-1488.
Richards et al., "Man's best friend: what can pet dogs teach us about non-Hodgkin lymphoma?" Inmunol Rev., 2016, 263 (1), 173-191.
Riddles et al., "Ellman's reagent: 5,5'-dithiobis(2-nitrobenzoic acid)—a reexamination," Anal Biochem. 1979, 94(1):75-81.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, 2015, 17, 661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.
Robinet et al. "Elastin-derived peptides enhance angiogenesis by promoting endothelial cell migration and tubulogenesis through upregulation of MTI-MMP," J. Cell Science, 2005, 118:343-356.
Römer et al., "The elaborate structure of spider silk: structure and function of a natural high performance fiber," Prion 2, 2008, 154-161.
Roopenian et al., "FcRn: the neonatal Fc receptor comes of age," Nat. Rev. Immunol., 2007, vol. 7, No. 9, 715-725.
Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, 2016, 12, 669-685.

(56) References Cited

OTHER PUBLICATIONS

Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Saifer et al., "Selectivity of binding of PEGs and PEG-like oligomers to anti-PEG antibodies induced by methoxyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schellenberger et al., "A recombinant polypeptide extends the in vivo half-life of peptides and proteins in a tunable manner," Nat. Biotechnol. 27, 2009, 1186-1188.
Schlaff et al., "Bringing the heavy: carbon ion therapy in the radiobiological clinical context," Radiation Oncology, 2014, 9, 1-18.
Schneider et al., "NIH Image to ImageJ: 25 years of image analysis," Nature Methods, 2012, 9, 671-675.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Shen et al., "Conjugation site modulates the in vivo stability and thearpeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.
Sherman et al., "Next-Generation PEGylation Enables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.

Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Siegel et al., "Absorbed fractions for electrons and beta particles in spheres of various sizes," J Nucl Med, 1994, 35, 152-156.
Siegwart et al., "ATRP in the Design of Functional Materials for Biomedical Applications," Prog Polymer Science, 2012, vol. 37, No. 1, pp. 18-37.
Silberstein et al., "The SNM Practice Guideline for Therapy of Thyroid Disease with $^{131}$I, 3.0," J Nucl Med, 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Sisson et al., "Radiation safety in the treatment of patients with thyroid diseases by radioiodine $^{131}$I: practice recommendations of the American Thyroid Association," Thyroid, 2011, 21, 335-346.
Sonawane et al., "Hydrazo linkages in pH responsive drug delivery systems," European Journal Pharmaceutical Sciences, 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, 2016, 234:83-89.
Sriraman et al., "Barriers to drug delivery in solid tumors," Tissue Barriers, 2014, 2, 2-10.
Stefl et al., "RNA sequence-and shape-dependent recognition by proteins in the ribonucleoprotein particle" EMBO reports (2005) 6(1):33-38.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.
Strohmaier et al., "Comparison of $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, 2015, 10, 1-17.
Sumerlin, "Proteins as Initiators of Controlled Radical Polymerization: Grafting-from via ATRP and RAFT," ACS Macro Lett. 2012, 1, 141-145.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "EUS-guided interstitial brachytherapy of the pancreas: a feasibility study," Gastrointestinal Endoscopy, 2005, 62, 775-779.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.

(56) References Cited

OTHER PUBLICATIONS

Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng 2014, 42, 1508-1516.
Swee et al., "Sortase-mediated modification of αDEC205 affords optimization of antigen presentation and immunization against a set of viral epitopes," Proc Natl Acad Sci USA, 2013, 110(4):1428-1433.
Swers et al., Multivalent Scaffold Proteins as Superagonists of TRAIL Receptor 2-Induced Apoptosis, Mol Cancer Ther, 2013, 12, 1235-1244.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., 2016, 15, 419-424.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., 2016, 15, 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Teicher, "In vivo/ex vivo and in situ assays used in cancer research: a brief review," Toxicol. Pathol., 2009, 37 (1), 114-122.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tompa et al., "Fuzzy complexes: polymorphism and structural disorder in protein-protein interactions," Trends Biochem Sci, 2008, 33, 2-8.
Tong et al., "Protein Modification with Amphiphilic Block Copoly(2-oxazoline)s as a New Platform for Enhanced Cellular Delivery," Mol. Pharm., 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of Staphylococcus aureus and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.

Trabbic-Carlson et al., "Expression and purification of recombinant proteins from Escherichia coli: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, 2014, 24, 140-147.
Trieu et al., "P0157 Preclinical evaluation of NBN-paclitaxel in pancreatic cancer xenograft models," Eur J Cancer, 2014, 50, e53.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tsume et al., "The development of orally administrable gemcitabine prodrugs with D-enantiomer amino acids: Enhanced membrane permeability and enzymatic stability," Eur. J. Pharm. Biopharm. 2014, 86(3):514-523.
Tu et al., "Stages in tropoelastin coalescence during synthetic elastin hydrogel formation," Micron, 2010, 41, 268-272.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Tward et al., "Survival of men with clinically localized prostate cancer treated with prostatectomy, brachytherapy, or no definitive treatment: impact of age at diagnosis," Cancer, 2006, 107, 2392-2400, doi:10.1002/cncr.22261.
Uchida et al., "Potential of adenovirus-mediated REIC/Dkk-3 gene therapy for use in the treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.
Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vasey et al., "Phase I clinical and Pharmacokinetic study of PK1 (N-(2-Hydroxypropyl)methacrylamide Copolymer Doxorubicin): First

(56) References Cited

OTHER PUBLICATIONS member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., 2011, vol. 22, pp. 976-986.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry of tropoelastin," Eur J Biochem, 1998, 258, 1-18.
Vrignaud et al., "Strategies for the nanoencapsulation of hydrophilic molecules in polymer-based nanoparticles," Biomaterials 2011, 32(33):8593-8604.
Walczak, "Death Receptor—Ligand Systems in Cancer, Cell Death, and Inflammation," Cold Spring Harb. Perspect. Biol., 2013, 5, a008698.
Walsh et al., "Post-translational modifications in the context of therapeutic proteins," Nat. Biotechnol., 2006, 24, 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm. 2014, 11, 1140-1150.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparticles in Endo-Lysosomes by Local pH," Nano Lett, 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Wendt et al., "DNA-mediated Folding and Assembly of MyoD-E47 Heterodimers," Journal of Biol. Chem., 1998, 273(10):5735-5743.
Werle et al., "Strategies to improve plasma half life time of peptide and protein drugs," Amino Acids 30, 2006, 351-367.
Wienkers et al., "Predicting in vivo drug interactions from in vitro drug discovery data," Nat. Rev. Drug. Discov. 2005, 4(10):825-833.
Williams et al., "Targeted radionuclide therapy," Medical Physics, 2008, 35, 3062-3068.
Williamson et al., "Efficient N-terminal labeling of proteins by use of sortase," Angew Chem Int ed Engl, 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.

Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, 2016, 79, 405-412.
Xia et al., "Tunable self-assembly of genetically engineered silk-elastin-like protein polymers," Biomacromolecules, 2011, 12, 3844-3850.
Xu et al., "A quality by design (QbD) case study on liposomes containing hydrophilic API: II. Screening of critical variables, and establishment of design space at laboratory scale," Int. J. Pharm. 2012, 423(2):543-553.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Genetically engineered block copolymers: influence of the length and structure of the coiled-coil blocks on hydrogel self-assembly," Pharm Res, 2008, 25, 674-682.
Xu et al., "Role of pancreatic stellate cells in pancreatic cancer metastasis," Am J of Pathology, 2010, 177, 2585-2596.
Xu et al., "Self-assembly behavior of peptide amphiphiles (PAs) with different length of hydrophobic alkyl tails," Colloids Surfaces B Biointerfaces, 2010, 81, 329-335.
Yang et al., "Poly(carboxybetaine) nano materials enable long circulation and prevent polymer-specific antibody production," Nano Today, 2014, 9(1):10-16.
Yates et al., "Contemporary management of patients with high-risk non-muscle-invasive bladder cancer who fail intravesical BCG therapy," World journal of urology, 2011, 29, 415-422.
Yeo et al., "Coacervation of tropoelastin," Adv Colloid Interface Sci, 2011, 167, 94-103.
Yokoe et al., "Albumin-conjugated PEG liposome enhances tumor distribution of liposomal doxorubicin in rats," International Journal of Pharmaceutics, 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability," Biochem. Pharmacol, 2007, 73: 84-93.
Youn et al., "High-yield production of biologically active mono-PEGylated salmon calcitonin by site-specific PEGylation," J. Control. Release 117, 2007, 371-379.
Yousefpour et al., "Co-opting biology to deliver drugs," Biotechnol Bioeng, 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett 2018, 18(12): 7784-7793.

(56) References Cited

OTHER PUBLICATIONS

Yu et al., "Effectiveness and security of CT-guided percutaneous implantation of (125)I seeds in pancreatic carcinoma," The British journal of radiology, 2014, 87, 20130642, 7 pages.
Zhang et al., "A self-assembly pathway to aligned monodomain gels," Nat. Mater., 2010, 9, 594-601.
Zhang et al., "Nanoparticles in medicine: therapeutic applications and developments," Clin. Pharmacol. Ther. 2008, 83(5):761-769.
Zhang et al., "Novel agents for pancreatic ductal adenocarcinoma: emerging therapeutics and future directions," Jounral of Hematology & Oncology, 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "A new Bliss Independence model to analyze drug combination data," J Biomol Screen, 2014, 19, 817-821.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, 2011, 60, 1055-1065.
Zong et al., "Crystal structures of *Staphylococcus aureus* sortase A and its substrate complex," J. Biol. Chem. 279, 2004, 31383-31389.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
United States Patent Office Action for U.S. Appl. No. 15/749,797 dated Oct. 20, 2020 (16 pages).
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US2019/061144 dated May 21, 2020 (15 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
Aaron et al., "Elastin as a Random-Network Elastomer—a Mechanical and Optical Analysis of Single Elastin Fibers," Biopolymers, 1981, 20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic, " Bioeng Transl Med, Jun. 2016, 1(1):10-29.
Arami et al., "In vivo delivery, pharmacokinetics, biodistribution and toxicity of iron oxide nanoparticles," Chem Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3):198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.
Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.

(56) References Cited

OTHER PUBLICATIONS

Borst et al., "The Therapeutic Antibody LM609 Selectively Inhibits Ligand Binding to Human aVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci USA, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6):1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell—material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci U S A, 2013, 110(33):13392-13397.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Ehlerding et al., "Biodegradable and Renal Clearable Inorganic Nanoparticles," Adv Sci (Weinh), Feb. 2016, 3(2):1500223.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.

Elsabahy et al., "Design of polymeric nanoparticles for biomedical delivery applications," Chem Soc Rev, 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.
Farokhzad et al., "Targeted nanoparticle-aptamer bioconjugates for cancer chemotherapy in vivo," Proc Natl Acad Sci U S A, 2006, 103(16):6315-20.
Franzmann et al., "Phase separation of a yeast prion protein promotes cellular fitness," Science, Jan. 2018, 359(6371):eaao5654.
Garcia Quiroz et al., "Syntax of Phase Transition Peptide Polymers with LCST and UCST Behavior," Jan. 1, 2013, Retrieved from the Internet: URL: https://dukespace.lib.duke.edu/dspace/bitstream/handle/10161/7256/GarciaQuirozduke0066D 11972.pdf?sequence=1&isAllowed=y.
Geng et al., Shape effects of filaments versus spherical particles in flow and drug delivery, Nat Nanotechnol, 2007, 2(4):249-55.
Gilbreth et al., "Structural insights for engineering binding proteins based on non-antibody scaffolds," Curr Opin Struct Biol, 2012, 22(4):413-20.
Gillies et al., "Dendrimers and dendritic polymers in drug delivery," Drug Discovery Today, 2005, 10(1):35-43.
Goldsmith et al., "Enzyme engineering: reaching the maximal catalytic efficiency peak," Curr Opin Struct Biol, Dec. 2017, 47:140-150.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, 2008, 105(33):11613-8.
Gu et al., "Precise engineering of targeted nanoparticles by using self-assembled biointegrated block copolymers," Proc Natl Acad Sci U S A, 2008, 105(7):2586-91.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al.,"Functional Implications of Intracellular Phase Transitions," Biochemistry, May 2018, 57(17):2415-2423.
Huber et al., "Designer amphiphilic proteins as building blocks for the intracellular formation of organelle-like compartments," Nat Mater, Jan. 2015, 14(1):125-132.
Jiang et al., "Nanoparticle-mediated cellular response is size-dependent," Nat Nanotechnol, 2008, 3(3):145-50.
Jokerst et al., "Nanoparticle PEGylation for imaging and therapy," Nanomedicine (Lond), 2011, 6(4):715-28.
Jurney et al., "Unique size and shape-dependent uptake behaviors of non-spherical nanoparticles by endothelial cells due to a shearing flow," J Control Release, Jan. 2017, 245:170-176.
Kamaly et al., "Targeted polymeric therapeutic nanoparticles: design, development and clinical translation," Chem Soc Rev, 2012, 41(7):2971-3010.
Karagoz et al., "Polymerization-Induced Self-Assembly (PISA)—control over the morphology of nanoparticles for drug delivery applications," Polym. Chem., Jan. 2014, 5(2):350-355.
Kataoka et al., "Block copolymer micelles for drug delivery: Design, characterization and biological significance," Advanced Drug Delivery Reviews, 2001, 47:113-131.
Kelly et al., "Shape-specific, monodisperse nano-molding of protein particles," J Am Chem Soc, 2008, 130(16):5438-9.
Kesharwani et al., "Dendrimer as nanocarrier for drug delivery," Progress in Polymer Science, Feb. 2014, 39(2):268-307.
Kulkarni et al., "Design of lipid nanoparticles for in vitro and in vivo delivery of plasmid DNA," Nanomedicine, May 2017, 13(4):1377-1387.
Lee et al., "Polymersomes for drug delivery: design, formation and characterization," J Control Release, 2012, 161(2):473-83.
Lewis et al., "Use of digitized video microscopy with a fluorogenic enzyme substrate to demonstrate cell-and compartment-specific gene expression in *Salmonella enteritidis* and Bacillus subtilis," Molecular microbiology, 1994, 13:655-662.

(56) References Cited

OTHER PUBLICATIONS

Li et al., "Phase transitions in the assembly of multivalent signalling proteins," Nature, 2012, 483(7389):336-340.

Li et al., "Tunable Assembly of Protein-Microdomains in Living Vertebrate Embryos," Advanced Biosystems, Oct. 2018, 2(10):1800112.

Lin et al., "Formation and Maturation of Phase-Separated Liquid Droplets by RNA-Binding Proteins," Mol Cell, Oct. 2015, 60(2):208-219.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Liong et al., "Multifunctional inorganic nanoparticles for imaging, targeting, and drug delivery," ACS Nano, 2008, 2(5):889-96.

Liu et al., "Integrin $\alpha_v\beta_3$-Targeted Cancer Therapy," Drug Dev Res, 2008, 69(6):329-339.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry 2009, 19(22):3576-3590.

Lukyanov et al., "Tumor-targeted liposomes: doxorubicin-loaded long-circulating liposomes modified with anti-cancer antibody," J Control Release, 2004, 100(1):135-44.

Lyons et al., "Comparisons of Recombinant Resilin-like Proteins: Repetitive Domains Are Sufficient to Confer Resilin-like Properties," Biomacromolecules, 2009, 10(11):3009-3014.

Lyons et al., "Design and facile production of recombinant resilin-like polypeptides: Gene construction and a rapid protein purification method," Protein Engineering Design & Selection, 2007, 20(1):25-32.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Malam et al., "Liposomes and nanoparticles: nanosized vehicles for drug delivery in cancer," Trends Pharmacol Sci 2009, 30(11):592-9.

Manders et al., "Dynamics of three-dimensional replication patterns during the S-phase, analysed by double labelling of DNA and confocal microscopy," Journal of cell science, 1992, 103(Pt 3):857-862.

Mao et al., "Net charge per residue modulates conformational ensembles of intrinsically disordered proteins," Proc Natl Acad Sci U S A, 2010, 107(18):8183-8188.

Masood, "Polymeric nanoparticles for targeted drug delivery system for cancer therapy," Mater Sci Eng C Mater Biol Appl, Mar. 2016, 60:569-578.

Mastria et al., "Nanoparticle formulation improves doxorubicin efficacy by enhancing host antitumor immunity," J Control Release, Jan. 2018, 269:364-373.

McKenzie et al., "Multivalent Binding of a Ligand-Coated Particle: Role of Shape, Size, and Ligand Heterogeneity," Biophys J, Apr. 2018, 114(8):1830-1846.

Meng et al., "Stimuli-responsive polymersomes for programmed drug delivery," Biomacromolecules, 2009, 10(2):197-209.

Merkel et al., "Using mechanobiological mimicry of red blood cells to extend circulation times of hydrogel microparticles," Proc Natl Acad Sci U S A, 2011, 108(2):586-91.

Mitragotri et al., "Physical approaches to biomaterial design," J. Nat Mater, 2009, 8(1):15-23.

Modery et al., "Heteromultivalent liposomal nanoconstructs for enhanced targeting and shear-stable binding to active platelets for site-selective vascular drug delivery," Biomaterials, 2011, 32(35):9504-9514.

Molliex et al., "Phase separation by low complexity domains promotes stress granule assembly and drives pathological fibrillization," Cell, Sep. 2015, 163(1):123-133.

Moosmann et al., "Alpha complementation of LacZ in mammalian cells," Nucleic Acids Res, 1996, 24(6):1171-1172.

Mozhdehi et al., "Genetically Encoded Cholesterol-Modified Polypeptides," Journal of the American Chemical Society, Jan. 2019, 141(2):945-951.

Mozhdehi et al., "Genetically encoded lipid—polypeptide hybrid biomaterials that exhibit temperature-triggered hierarchical self-assembly," Nature chemistry, May 2018, 10(5):496-505.

Muiznieks et al., "Proline periodicity modulates the self-assembly properties of elastin-like polypeptides," J Biol Chem, 2010, 285(51):39779-39789.

Muro, "Challenges in design and characterization of ligand-targeted drug delivery systems," J Control Release, 2012, 164(2):125-37.

Napier et al., "Nanoparticle drug delivery platform," Journal of Macromolecular Science, Part C: Polymer Reviews, 2007, 47(3):321-327.

Nayeem et al., "Engineering enzymes for improved catalytic efficiency: a computational study of site mutagenesis in epothilone-B hydroxylase," Protein Eng Des Sel, 2009, 22(4):257-266.

Ni et al., "Engineering of inorganic nanoparticles as magnetic resonance imaging contrast agents," Chem Soc Rev, Nov. 2017, 46(23):7438-7468.

Niu et al., "The role of adhesion molecules, $\alpha v\beta 3$, $\alpha v\beta 5$ and their ligands in the tumor cell and endothelial cell adhesion," Eur J Cancer Prey, 2007, 16(6):517-27.

Nott et al., "Phase transition of a disordered nuage protein generates environmentally responsive membraneless organelles," Mol Cell, Mar. 2015, 57(5):936-947.

Ortega et al., "Hydrodynamic properties of rodlike and dislike particles in dilute solution," The Journal of Chemical Physics, 2003, 119(18):9914-9919.

Pak et al., "Sequence Determinants of Intracellular Phase Separation by Complex Coacervation of a Disordered Protein," Mol Cell, Jul. 2016, 63(1):72-85.

Palmerston Mendes et al., "Dendrimers as Nanocarriers for Nucleic Acid and Drug Delivery in Cancer Therapy," Molecules, Aug. 2017, 22(9):1401.

Pardridge, "The blood-brain barrier: bottleneck in brain drug development," NeuroRx, 2005, 2(1):3-14.

Parker et al., "Antibody mimics based on human fibronectin type three domain engineered for thermostability and high-affinity binding to vascular endothelial growth factor receptor two," Protein Eng Des Sel, 2005, 18(9):435-44.

Pastuszka et al., "A tunable and reversible platform for the intracellular formation of genetically engineered protein microdomains," Biomacromolecules, 2012, 13(11):3439-3444.

Peng et al., "Length-dependent prediction of protein intrinsic disorder," BMC Bioinformatics, 2006, 7:208.

Petros et al., "Strategies in the design of nanoparticles for therapeutic applications," Nat Rev Drug Discov, 2010, 9(8):615-27.

Qamar et al., "FUS Phase Separation Is Modulated by a Molecular Chaperone and Methylation of Arginine Cation-pi Interactions," Cell, Apr. 2018, 173(3):720-734.e15.

Quiroz et al., "Intrinsically disordered proteins access a range of hysteretic phase separation behaviors," Scientific advances, Oct. 2019, 5(10):eaax5177.

Ravikumar et al., "Mimicking adhesive functionalities of blood platelets using ligand-decorated liposomes," Bioconjugate chemistry, 2012, 23(6):1266-1275.

Rolland et al., "Direct fabrication and harvesting of monodisperse, shape-specific nanobiomaterials," J Am Chem Soc, 2005, 127(28):10096-100.

Rosenholm et al., "Towards multifunctional, targeted drug delivery systems using mesoporous silica nanoparticles—opportunities & challenges," Nanoscale, 2010, 2(10):1870-83.

(56) References Cited

OTHER PUBLICATIONS

Rösier et al., "Advanced drug delivery devices via self-assembly of amphiphilic block copolymers," Advanced Drug Delivery Reviews, 2001, 53:95-108.
Ryu et al., "Elastin-like polypeptide for improved drug delivery for anticancer therapy: preclinical studies and future applications," Expert Opinion on Drug Delivery, 2014, 12(4):653-667.
Sanna et al., "Targeted therapy using nanotechnology: focus on cancer," Int J Nanomedicine, Jan. 2014, 9:467-83.
Schnell et al., "Expression of integrin αvβ3 in gliomas correlates with tumor grade and is not restricted to tumor vasculature," Brain Pathol, 2008, 18(3):378-86.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, 2010, 147(3):408-412.
Shi et al., "Triggered sorting and co-assembly of genetically engineered protein microdomains in the cytoplasm," Adv Mater, 2014, 26(3):449-454.
Shin et al., "Liquid phase condensation in cell physiology and disease," Science, Sep. 2017, 357(6357):eaaf4382.
Sickmeier et al., "DisProt: the Database of Disordered Proteins," Nucleic Acids Res, 2007, 35:D786-793.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Skerra, "Alternative non-antibody scaffolds for molecular recognition," Curr Opin Biotechnol, 2007, 18(4):295-304.
Smits et al., "Elastin-Like Polypeptide Based Nanoparticled: Design Rationale Toward Nanomedicine," Macromolecular Bioscience, 2014, 15(1):36-51.
Steichen et al., "A Review of Current Nanoparticle and Targeting Moieties for the Delivery of Cancer Therapeutics," Eur J Pharm Sci, 2013, 48(3):416-27.
Strulson et al., "RNA catalysis through compartmentalization," Nat Chem, 2012, 4(11):941-946.
Suk et al., "PEGylation as a Strategy for Improving Nanoparticle-Based Drug and Gene Delivery," Adv Drug Deliv Rev, Apr. 2016, 99(Pt A):28-51.
Swider et al., "Customizing Poly(lactic-Co-Glycolic Acid) Particles for Biomedical Applications," Acta Biomater, Jun. 2018, 73:38-51.
Talelli et al., "Core-Crosslinked Polymeric Micelles: Principles, Preparation, Biomedical Applications and Clinical Translation," Nano Today, Feb. 2015, 10(1):93-117.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, 2013, 1(1):e24360.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, 2011, 32(33):8462-73.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, 2010, 1804(6):1231-1264.

Vazquez-Lombardi et al., "Challenges and Opportunities for Non-Antibody Scaffold Drugs," Drug Discov Today, Oct. 2015, 20(10):1271-83.
Venkataraman et al., "The Effects of Polymeric Nanostructure Shape on Drug Delivery," Adv Drug Deliv, Rev, 2011, 63(14-15):1228-46.
Verma et al., "Effect of surface properties on nanoparticle-cell interactions," Small, 2010, 6(1):12-21.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, 2006, 78(3):620-8.
Vrhovski et al., "Coacervation Characteristics of Recombinant Human Tropoelastin," European Journal of Biochemistry, 1997, 250(1):92-98.
Wang et al., "A Molecular Grammar Governing the Driving Forces for Phase Separation of Prion-like RNA Binding Proteins," Cell, Jul. 2018, 174(3):688-699.e616.
Wang et al., "More effective nanomedicines through particle design," Small, 2011, 7(14):1919-31.
Wang et al., "Nanoparticle delivery of cancer drugs," Annu Rev Med, 2012, 63:185-98.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface to Enhance Cancer Cell Targeting by Polymer Micelles," Nano Lett Oct. 2017, 17(10):5995-6005.
Wechsel et al., "Renal Cell Carcinoma: Immunohistological Investigation of Expression of the Integrin αvβ3," Anticancer research, 1999, 19(2C):1529-1532.
Weis et al., "αV Integrins in Angiogenesis and Cancer," Cold Spring Harb Perspect Med, 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wilkins et al., "Hydrodynamic Radii of Native and Denatured Proteins Measured by Pulse Field Gradient NMR Techniques," Biochemistry, 1999, 38(50):16424-16431.
Wimley et al., "Experimentally determined hydrophobicity scale for proteins at membrane interfaces," Nature Structural & Molecular Biology, 1996, 3(10):842-848.
Wright et al., "Intrinsically disordered proteins in cellular signalling and regulation," Nat Rev Mol Cell Biol, Jan. 2015, 16(1):18-29.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, 2011, 155(2):248-61.
Xu et al., "Inorganic nanoparticles as carriers for efficient cellular delivery," Chemical Engineering Science, 2006, 61(3):1027-1040.
Zhao et al., "Cellular uptake, intracellular trafficking, and cytotoxicity of nanomaterials," Small, 2011, 7(10):1322-37.
Zhao et al., "Tumor αvβ3 Integrin Is a Therapeutic Target for Breast Cancer Bone Metastases," Cancer Res, 2007, 67(12):5821-30.
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
European Patent Office Extended Search Report for Application No. 17853962.3 dated Mar. 3, 2020 (8 pages).
Chockalingam et al., "Design and application of stimulus-responsive peptide systems," Protein Engineering, Design & Selection, 2007, 20(4):155-161.
United States Patent Office Action for U.S. Appl. No. 16/525,374 dated Dec. 7, 2020 (9 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.

(56) References Cited

OTHER PUBLICATIONS

Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Chu et al., "Controllable monodisperse multiple emulsions," Angew Chem Int Ed Engl, 2007, 46: 8970-8974.
Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64: 1868-1873.
Hwang et al., "Differentially degradable janus particles for controlled release applications," Macromol Rapid Commun, 2012, 33: 1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013, 2: 667-672.
Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.

Panda et al., "Stop-flow lithography to generate cell-laden microgel particles," Lab Chip, 2008, 8: 1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membraneless organelles," Adv Colloid Interface Sci, 2017, 239: 97-114.
Volodkin et al., "One-Step Formulation of Protein Microparticles with Tailored Properties: Hard Templating at Soft conditions," Advanced Functional Materials, 2012, 22: 1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
Resh, "Covalent Lipid Modifications of Proteins," Curr Biol., May 2013, 23(10): R431-R435.
United States Patent Office Action for U.S. Appl. No. 16/477,229 dated Apr. 12, 2021 (14 pages).
European Patent Office Action for Application No. 17853962.3 dated May 3, 2021 (4 pages).
Frandsen et al., "Recombinant protein-based polymers for advanced drug delivery," Chem Soc Rev, 2012,41:2696-2706.
Hess et al., "Graphene Transistors for Multifunctional Polymer Brushes for Biosensing Applications," Applied Materials & Interfaces, 2014, 6: 9705-9710.
Hwang et al., "Synthesis and Characterization of Polystyrene Brushes for Organic Thin Film Transistors," Journal of Nanoscience and Nanotechnology, 2012, 12: 4137-4141.
Park et al., "Polymer Brush As a Facile Dielectric Surface Treatment for High-Performance, Stable, Soluble Acene-Based Transistors," Chemistry of Materials, 2010, 22: 5377-5382.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Action for U.S. Appl. No. 16/305,696 dated Jun. 22, 2021 (20 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
Japanese Patent Office Action for Application No. 2019-515805 dated Aug. 2, 2021 (10 pages, English translation included).

\* cited by examiner

UNSTRUCTURED NON-REPETITIVE POLYPEPTIDES HAVING LCST BEHAVIOR

CROSS-REFERENCE TO RELATED APPLICATIONS

This application claims priority to U.S. Provisional Patent Application No. 62/399,123, filed Sep. 23, 2016, which is incorporated herein by reference in its entirety.

STATEMENT REGARDING FEDERALLY SPONSORED RESEARCH

This invention was made with government support under grant GM061232, awarded by the National Institutes of Health. The government has certain rights in the invention.

BACKGROUND

Proteins can be useful therapeutic agents when engineered for specificity, and selectivity for a clinical target. Their complexity, versatility, tolerability, and diversity often make them superior alternatives to small molecule drugs, and the long half-life, specificity, and selectivity can make them attractive for therapies. Although protein engineering allows for the development of potent therapeutics targeted toward a protein or receptor of interest, the body has many mechanisms with which to clear such protein therapies. Accordingly, there exists a need for reliable and broadly applicable protein delivery solutions.

SUMMARY

In one aspect, disclosed are unstructured polypeptides having no discernible repeat motif, wherein the polypeptide is soluble below the lower critical solution temperature (LCST), soluble above the upper critical solution temperature (UCST), or a combination thereof, wherein the LCST and UCST are each independently from about 0° C. to about 100° C.

In another aspect, disclosed are fusion proteins comprising at least one binding polypeptide and at least one of the disclosed unstructured polypeptides.

In another aspect, disclosed are methods for treating a disease in a subject in need thereof, the methods comprising administering to the subject an effective amount of a disclosed fusion protein.

In another aspect, disclosed are methods of diagnosing a disease in a subject, the methods comprising contacting a sample from the subject with a disclosed fusion protein; and detecting binding of the fusion protein to a target to determine presence of the target in the sample, wherein the presence of the target in the sample indicates the disease in the subject.

In another aspect, disclosed are methods of determining the presence of a target in a sample, the methods comprising contacting the sample with a disclosed fusion protein under conditions to allow a complex to form between the fusion protein and the target in the sample; and detecting the presence of the complex, wherein presence of the complex is indicative of the target in the sample.

In another aspect, disclosed are methods of determining the effectiveness of a treatment for a disease in a subject in need thereof, the methods comprising contacting a sample from the subject with a disclosed fusion protein under conditions to allow a complex to form between the fusion protein and a target in the sample; determining the level of the complex in the sample, wherein the level of the complex is indicative of the level of the target in the sample; and comparing the level of the target in the sample to a control level of the target, wherein if the level of the target is different from the control level, then the treatment is determined to be effective or ineffective in treating the disease.

In another aspect, disclosed are methods of diagnosing a disease in a subject, the methods comprising contacting a sample from the subject with a disclosed fusion protein; determining the level of a target in the sample; and comparing the level of the target in the sample to a control level of the target, wherein a level of the target different from the control level indicates disease in the subject.

BRIEF DESCRIPTION OF THE DRAWINGS

FIG. 3(A) is a graph showing repetitive and exemplary non-repetitive polypeptides comprising 200 amino acids. FIG. 3(B) is a graph showing repetitive and exemplary non-repetitive polypeptides comprising 400 amino acids.

FIG. 4(A) is a graph showing transition temperature characterization of exemplary non-repetitive unstructured polypeptides at 25 µM in PBS. FIG. 4(B) is a graph showing transition temperature characterization of exemplary non-repetitive unstructured polypeptides in PBS at various concentrations of urea.

DETAILED DESCRIPTION

Figure 1:
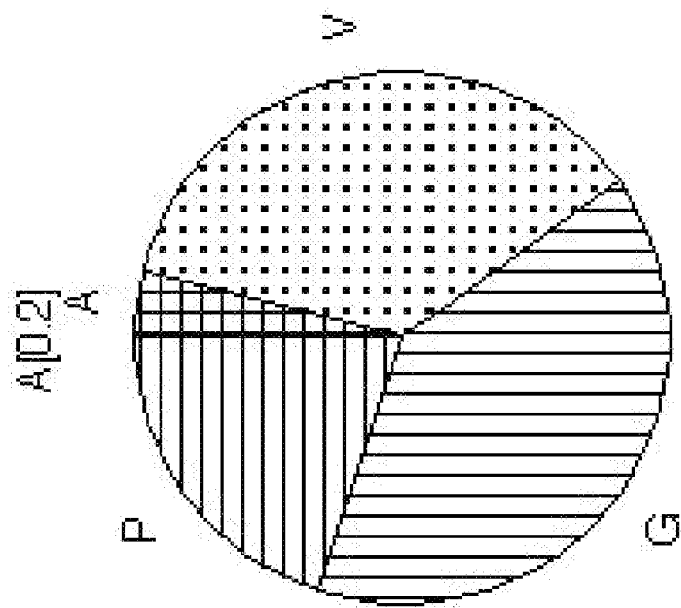
FIG. 1 is a diagram showing the amino acid compositions of the A[0.5] and A[0.2] sequences (SEQ ID NO: 1 and SEQ ID NO: 2). Correspondingly, the diagram also shows the amino acid compositions of polypeptides of SEQ ID NOs: 4, 6, 8, and 10 and SEQ ID NOs: 3, 5, 7, and 9, respectively.
Figure 1:
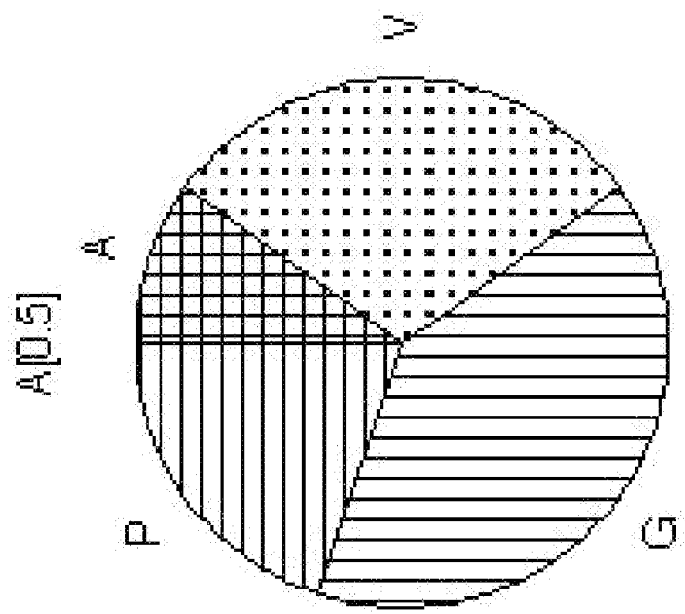

Elastin-like polypeptides (ELPs) are repetitive polypeptides. "ELP" refers to a polypeptide comprising the pentapeptide repeat sequence $(VPGXG)_n$, wherein X is any amino acid except proline and n is an integer greater than or equal to 1 (SEQ ID NO: 23). ELPs have been examined and characterized as having lower critical solution temperature (LCST) behavior. ELPs may include, for example, repeating subsequences of GAGVPGVGVP (SEQ ID NO: 1) or GVGVPGVGVPGAGVPGVGVPGVGVP (SEQ ID NO: 2), herein referred to as A[0.5] and A[0.2] respectively (see McDaniel, J. R. et al. (2013) *Biomacromolecules*, which is incorporated by reference herein in its entirety). For example, A[0.2] rep-200 (SEQ ID NO: 3, $(GVGVPGVGVPGAGVPGVGVPGVGVP)_8$) includes the A[0.2] subsequence repeated 8 times for a total of 200 amino acids. A[0.5] rep-200 (SEQ ID NO: 4, (GAGVPGVGVP)$_{20}$) includes the A[0.5] subsequence repeated 20 times for a total of 200 amino acids. A[0.2] rep-400 (SEQ ID NO: 5, (GVGVPGVGVPGAGVPGVGVPGVGVP)$_{16}$) includes the A[0.2] subsequence repeated 16 times for a total of 400 amino acids. A[0.5] rep-400 (SEQ ID NO: 6, (GAGVPGVGVP)$_{40}$) includes the A[0.5] subsequence repeated 40 times for a total of 400 amino acids. The amino acid compositions of these sequences are depicted in FIG. 1.

Disclosed herein are unstructured, non-repetitive polypeptides that lack the requisite pentapeptide sequence of ELPs, yet unexpectedly still have LCST behavior. Accordingly, the disclosed unstructured polypeptides lack secondary structure (according to CD) and are thermally responsive, all without having a discernable repetitive sequence within the polypeptide.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, the term "affinity" refers to the binding strength of a binding polypeptide to its target (i.e., binding partner).

As used herein, the term "agonist" refers to an entity that binds to a receptor and activates the receptor to produce a biological response. An "antagonist" blocks or inhibits the action or signaling of the agonist. An "inverse agonist" causes an action opposite to that of the agonist. The activities of agonists, antagonists, and inverse agonists may be determined in vitro, in situ, in vivo, or a combination thereof.

As used herein, the term "biomarker" refers to a naturally occurring biological molecule present in a subject at varying concentrations that is useful in identifying and/or classifying a disease or a condition. The biomarker can include genes, proteins, polynucleotides, nucleic acids, ribonucleic acids, polypeptides, or other biological molecules used as an indicator or marker for disease. In some embodiments, the biomarker comprises a disease marker. For example, the biomarker can be a gene that is upregulated or downregulated in a subject that has a disease. As another example, the biomarker can be a polypeptide whose level is increased or decreased in a subject that has a disease or risk of developing a disease. In some embodiments, the biomarker comprises a small molecule. In some embodiments, the biomarker comprises a polypeptide.

As used herein, the terms "control," "reference level," and "reference" are used interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice.

As used herein, the term "expression vector" indicates a plasmid, a virus or another medium, known in the art, into which a nucleic acid sequence for encoding a desired protein can be inserted or introduced.

As used herein, the term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

As used herein, the term "reporter," "reporter group," "label," and "detectable label" are used interchangeably herein. The reporter is capable of generating a detectable signal. The label can produce a signal that is detectable by visual or instrumental means. A variety of reporter groups can be used, differing in the physical nature of signal transduction (e.g., fluorescence, electrochemical, nuclear magnetic resonance (NMR), and electron paramagnetic resonance (EPR)) and in the chemical nature of the reporter group. Various reporters include signal-producing substances, such as chromagens, fluorescent compounds, chemiluminescent compounds, radioactive compounds, and the like. In some embodiments, the reporter comprises a radiolabel. Reporters may include moieties that produce light, e.g., acridinium compounds, and moieties that produce fluorescence, e.g., fluorescein. In some embodiments, the signal from the reporter is a fluorescent signal. The reporter may comprise a fluorophore. Examples of fluorophores include, but are not limited to, acrylodan (6-acryloy 1-2-dimethylaminonaphthalene), badan (6-bromo-acetyl-2-dimethylamino-naphthalene), rhodamine, naphthalene, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), fluorescein, dipyrromethaneboron difluoride (BODIPY), 4-nitrobenzo[c][1,2,5]oxadiazole (NBD), Alexa fluorescent dyes, and derivatives thereof. Fluorescein derivatives may include, for example, 5-fluorescein, 6-carboxyfluorescein, 3'6-carboxyfluorescein, 5(6)-carboxyfluorescein, 6-hexachlorofluorescein, 6-tetrachlorofluorescein, fluorescein, and isothiocyanate.

As used herein, the term "sample" or "test sample" can mean any sample in which the presence and/or level of a target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the term "subject" as used herein can mean a mammal that wants or is in need of the herein described fusion proteins. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, the term "transition" or "phase transition" refers to the aggregation of thermally responsive polypeptides. Phase transition occurs sharply and reversibly at a specific temperature called the LCST or the inverse transition temperature $T_t$. Below the transition temperature (LCST or $T_t$), a thermally responsive polypeptide is highly soluble. Upon heating above the transition temperature, a thermally responsive polypeptide may hydrophobically collapse and aggregate, forming a separate, gel-like phase. Phase transition behavior may be used to form drug depots within a tissue of a subject for controlled and/or slow release of the polypeptide. "Inverse transition cycling" refers to a protein purification method for thermally responsive polypeptides. The protein purification method may involve the use of thermally responsive polypeptide's reversible phase transition behavior to cycle the solution through soluble and insoluble phases, thereby removing contaminants and eliminating the need for chromatography.

As used herein, the term "subsequence" refers to a sequence of contiguous amino acids that occurs within another sequence of contiguous amino acids. A subsequence includes at least two amino acids. In some embodiments, a subsequence is 2 to 50, 2 to 20, 2 to 15, or 2 to 10 sequential amino acids in length. In some embodiments, a subsequence includes 3, 4, 5, 6, 7, 8, 9, or 10 sequential amino acids.

As used herein, the term "substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, or 1100 amino acids.

As used herein, the term "treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present disclosure to a subject after induction of the disease but before its clinical appearance. Repressing or ameliorating the disease involves administering a composition of the present disclosure to a subject after clinical appearance of the disease.

As used herein, the term "valency" refers to the potential binding units or binding sites. The term "multivalent" refers to multiple potential binding units. The terms "multimeric" and "multivalent" are used interchangeably herein.

As used herein, the term "variant" with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof.

Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Unstructured Polypeptides

Disclosed herein are unstructured polypeptides. The unstructured polypeptide may comprise any suitable polypeptide lacking secondary structure as observed by CD, and which lacks any discernable repetitive sequences. In addition, the unstructured polypeptide may be soluble below its LCST and/or above its UCST at a given concentration, thereby conferring a phase transition characteristic to the polypeptide such that it may be referred to as a "thermally responsive polypeptide." LCST is the temperature below which the polypeptide is miscible. UCST is the temperature above which the polypeptide is miscible. The LCST is a separate and distinct temperature relative to the UCST. In some embodiments, the unstructured polypeptide may have only UCST behavior. In some embodiments, the unstructured polypeptide may have only LCST behavior. In some embodiments, the unstructured polypeptide may have both UCST and LCST behavior. In such embodiments, the UCST is higher than the LCST. The unstructured polypeptide may have a LCST of about 0° C. to about 100° C., such as about 10° C. to about 50° C., or about 20° C. to about 42° C. The unstructured polypeptide may have a UCST of about 0° C. to about 100° C., such as about 10° C. to about 50° C., or about 20° C. to about 42° C. In some embodiments, the unstructured polypeptide may have a transition temperature(s) (LCST and/or UCST) between room temperature (about 25° C.) and body temperature (about 37° C.). The unstructured polypeptide may have its LCST and/or UCST below body temperature or above body temperature at the concentration at which the unstructured polypeptide is administered to a subject. Thermally responsive unstructured polypeptides can phase transition at varying temperatures and concentrations. Thermally responsive unstructured polypeptides may not affect the binding or potency of a second polypeptide to which it is conjugated. In addition, thermally responsive unstructured polypeptides may be tuned to any number of desired transition temperatures, molecular weights, and formats.

The unstructured polypeptide may include varying amounts and types of amino acids. For example, the unstructured polypeptide may include a sequence of at least 50 amino acids, wherein at least 10% of the amino acids are proline (P), and at least 20% of the amino acids are glycine (G). In some embodiments, the unstructured polypeptide may include a sequence wherein at least 40% of the amino acids are selected from the group consisting of valine (V), alanine (A), leucine (L), lysine (K), threonine (T), isoleucine (I), tyrosine (Y), serine (S), and phenylalanine (F). In some embodiments, the unstructured polypeptide may include a sequence that does not contain three contiguous identical amino acids, wherein any 5-10 amino acid subsequence does not occur more than once in the unstructured polypeptide, and wherein when the unstructured polypeptide comprises a subsequence starting and ending with proline (P), the subsequence further includes at least one glycine (G).

In some embodiments, the unstructured polypeptide may include a sequence of at least 50 amino acids, wherein at least 10% of the amino acids are proline (P); wherein at least 20% of the amino acids are glycine (G); wherein at least 40% of the amino acids are selected from the group consisting of valine (V), alanine (A), leucine (L), lysine (K), threonine (T), isoleucine (I), tyrosine (Y), serine (S), and phenylalanine (F); wherein the sequence does not contain three contiguous identical amino acids; wherein any 5-10 amino acid subsequence does not occur more than once in the unstructured polypeptide; and wherein when the unstructured polypeptide comprises a subsequence starting and ending with proline (P), the subsequence further comprising at least one glycine (G).

Shorter subsequences of any of the non-repetitive sequences identified by the computer algorithm (as discussed below in the Examples) can maintain thermo-responsive behavior. Unstructured polypeptides comprising subsequences as short as 50 amino acids can satisfy the requirements of the algorithm, with similar composition as the full length sequence being sufficiently non-repetitive, because they are constrained by the same aforementioned sequence rules. Previous work has shown that intrinsic disorder can be encoded by unstructured peptides of less than 50 amino acids in length (see Radivojac et al. (2007) Biophys J., which is incorporated by reference herein in its entirety). Furthermore, ELPs as short as 50 amino acids can exhibit thermo-responsive LCST behavior, with measured transition temperatures within the range of 0 to 100° C. (see Aladini et al. (2016) J Pept Sci., which is incorporated by reference herein in its entirety). Accordingly in some embodiments, the unstructured polypeptide may comprise a 50 amino acid subsequence of any of SEQ ID NO: 7-18.

As mentioned above, the unstructured polypeptide may lack any discernable repeat motif of amino acids. The repetitiveness of the unstructured polypeptides may be characterized by its linguistic complexity score. Linguistic complexity score is defined by the total number of unique subsequences in a given sequence divided by the total number of unique subsequences possible for the same alphabet and window length (see Troyanskaya et al. (2002) Bioinformatics, which is incorporated by reference herein in its entirety). Further detail of linguistic complexity score can be found in Example 1 below. The unstructured polypeptide may have a linguistic complexity score, and the product of the linguistic complexity score and the amino acid sequence length of the unstructured polypeptide can be greater than 15, greater than 16, greater than 17, greater than 18, greater than 19, or greater than 20.

In some embodiments, the unstructured polypeptide may comprise an amino acid sequence selected from the group consisting of SEQ ID Nos: 7-18.

3. Fusion Proteins

Also disclosed herein are fusion proteins that can include at least one of the unstructured polypeptides, as described above. The fusion protein may further include at least one binding polypeptide and at least one linker.

In some embodiments, the fusion protein may include more than one binding polypeptide. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 binding polypeptides. The fusion protein may include less than 30, less than 25, or less than 20 binding polypeptides. The fusion protein may include 1 to 30, such as 1 to 20, or 1 to 10 binding polypeptides. In such embodiments, the binding polypeptides may be the same or different from one another. In some embodiments, the fusion protein may include more than one binding polypeptide positioned in tandem to one another. In some embodiments, the fusion protein may include 2 to 6 binding polypeptides. For example, the fusion protein may include two binding polypeptides, three binding polypeptides, four binding polypeptides, five binding polypeptides, or six binding polypeptides.

In some embodiments, the fusion protein may include more than one unstructured polypeptide. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 unstructured polypeptides. The fusion protein may include less than 30, less than 25, or less than 20 unstructured polypeptides. The fusion protein may include 1 to 30, such as 1 to 20, or 1 to 10 unstructured polypeptides. In such embodiments, the unstructured polypeptides may be the same or different from one another. In some embodiments, the fusion protein may include more than one unstructured polypeptide positioned in tandem to one another.

In some embodiments, the fusion protein may be arranged as a modular linear polypeptide. For example, the modular linear polypeptide may be arranged in one of the following structures: [binding polypeptide]$_m$—[linker]$_k$—[unstructured polypeptide]; [unstructured polypeptide]—[linker]$_k$—[binding polypeptide]$_m$; [binding polypeptide]$_m$—[linker]$_k$—[unstructured polypeptide]—[binding polypeptide]$_m$—[linker]$_k$—[unstructured polypeptide]; or [unstructured polypeptide]—[binding polypeptide]$_m$—[linker]$_k$—[unstructured polypeptide]—[binding polypeptide]$_m$, in which k and m are each independently an integer greater than or equal to 1. In some embodiments, m may be an integer less than or equal to 20. In some embodiments, m may be an integer equal to 1, 2, 3, 4, 5, 6, 7, 8, 9, 10, 11, 12, 13, 14, 15, 16, 17, 18, 19, or 20. In some embodiments, k may be an integer less than or equal to 10. In some embodiments, k may be an integer equal to 1, 2, 3, 4, 5, 6, 7, 8, 9, or 10. In some embodiments, the at least one binding polypeptide may be positioned N-terminal to the at least one unstructured polypeptide. In some embodiments, the at least one binding polypeptide may be positioned C-terminal to the at least one unstructured polypeptide.

In some embodiments, a fusion protein comprising one or more thermally responsive polypeptides may have a transition temperature between room temperature (about 25° C.) and body temperature (about 37° C.). The thermally responsive, unstructured polypeptide may have its LCST or UCST below body temperature or above body temperature at the concentration at which the fusion protein is administered to a subject.

The fusion protein may be expressed recombinantly in a host cell according to methods known within the art. The fusion protein may be purified by any suitable means known within the art. For example, the fusion protein may be purified using chromatography, such as liquid chromatography, size exclusion chromatography, or affinity chromatography, or through ultracentrifugation techniques. In some embodiments, the fusion protein may be purified without chromatography. In some embodiments, the fusion protein may be purified using inverse transition cycling.

a. Binding Polypeptide

The binding polypeptide may comprise any polypeptide that is capable of binding at least one target. The binding polypeptide may bind at least one target. "Target" may be an entity capable of being bound by the binding polypeptide. Targets may include, for example, another polypeptide, a cell surface receptor, a carbohydrate, an antibody, a small molecule, or a combination thereof. The target may be a biomarker. The target may be activated through agonism or blocked through antagonism. The binding polypeptide may specifically bind the target. By binding a target, the binding polypeptide may act as a targeting moiety, an agonist, an antagonist, or a combination thereof.

The binding polypeptide may be a monomer that binds to a target. The monomer may bind one or more targets. The binding polypeptide may form an oligomer. The binding polypeptide may form an oligomer with the same or different binding polypeptides. The oligomer may bind to a target. The oligomer may bind one or more targets. One or more monomers within an oligomer may bind one or more targets. In some embodiments, the fusion protein may be multivalent. In some embodiments, the fusion protein may bind multiple targets. In some embodiments, the activity of the binding polypeptide alone may be the same as the activity of the binding protein when part of a fusion protein.

In some embodiments, the binding polypeptide may comprise one or more scaffold proteins. As used herein, "scaffold protein" refers to one or more polypeptide domains with relatively stable and defined three-dimensional structures. Scaffold proteins may further have the capacity for affinity engineering. In some embodiments, the scaffold protein may be engineered to bind a particular target. In embodiments where the binding polypeptide comprises more than 1 scaffold protein, the scaffold proteins may be the same or different.

In some embodiments, the binding polypeptide may comprise Protein A. Protein A is a 42 kD protein originally derived from Staphylococcus aureus. It can exhibit high binding affinity to the constant region (Fc) of immunoglobulin G antibodies. Protein A includes 5 linked domains that are all able to bind antibody Fc. Immobilized protein A can be used for the purification of a variety of antibodies (see, e.g., Hober et al. (2006) J. Chromatogr. B, which is incorporated by reference herein in its entirety).

b. Linker

As mentioned above, the fusion protein may further include at least one linker. In some embodiments, the fusion protein may include more than one linker. In such embodiments, the linkers may be the same or different from one another. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, or at least 100 linkers. The fusion protein may include less than 500, less than 400, less than 300, or less than 200 linkers. The fusion protein may include 1 to 1000 linkers, such as 10 to 900, 10 to 800, or 5 to 500 linkers.

The linker may be positioned in between a binding polypeptide and an unstructured polypeptide, in between binding polypeptides, in between unstructured polypeptides, or a combination thereof. Multiple linkers may be positioned adjacent to one another. Multiple linkers may be positioned adjacent to one another and in between the binding polypeptide and the unstructured polypeptide.

The linker may be a polypeptide of any suitable amino acid sequence and length. The linker may act as a spacer peptide. The linker may occur between polypeptide domains. The linker may sufficiently separate the binding domains of the binding polypeptide while preserving the activity of the binding domains. In some embodiments, the linker may comprise charged amino acids. In some embodiments, the linker may be flexible. In some embodiments, the linker may comprise at least one glycine and at least one serine. In some embodiments, the linker may comprise an amino acid sequence consisting of (Gly$_4$Ser)$_3$ (SEQ ID NO: 21). In some embodiments, the linker may comprise at least one proline. In some embodiments, the linker may comprise an amino acid sequence consisting of SEQ ID NO:22.

c. Polynucleotides

Further disclosed are polynucleotides encoding the fusion proteins detailed herein. A vector may include the polynucleotide encoding the fusion proteins detailed herein. To obtain expression of a polypeptide, one typically subclones the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further disclosed is a host cell transformed or transfected with an expression vector comprising a polynucleotide encoding a fusion protein as detailed herein. Bacterial expression systems for expressing the protein are available in, e.g., *E. coli*, *Bacillus* sp., and *Salmonella* (Paiva et al., Gene 1983, 22, 229-235; Mosbach et al., Nature 1983, 302, 543-545, which are both incorporated by reference herein in their entirety). Kits for such expression systems are commercially available. Eukaryotic expression systems for mammalian cells, yeast, and insect cells are well known in the art and are also commercially available. Retroviral expression systems may also be used.

4. Administration

The fusion proteins as detailed above can be formulated in accordance with standard techniques known to those skilled in the pharmaceutical art. Such compositions comprising a fusion protein can be administered in dosages and by techniques known to those skilled in the medical arts taking into consideration such factors as the age, sex, weight, and condition of the particular subject, and the route of administration.

The fusion protein can be administered prophylactically or therapeutically. In prophylactic administration, the fusion protein can be administered in an amount sufficient to induce a response. In therapeutic applications, the fusion proteins can be administered to a subject in need thereof in an amount sufficient to elicit a therapeutic effect. An amount adequate to accomplish this is defined as "therapeutically effective dose." Amounts effective for this use will depend on, e.g., the particular composition of the fusion protein regimen administered, the manner of administration, the stage and severity of the disease, the general state of health of the patient, and the judgment of the prescribing physician.

The fusion protein can be administered by methods known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The fusion protein can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The fusion proteins can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the fusion protein can be administered intravenously, intraarterially, or intraperitoneally to the subject.

The fusion protein can be a liquid preparation such as a suspension, syrup, or elixir. The fusion protein can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The fusion protein may be used as a vaccine. The vaccine can be administered via electroporation, such as by a method described in U.S. Pat. No. 7,664,545, the contents of which are incorporated herein by reference in its entirety. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the fusion protein can be administered in a controlled release formulation. In some embodiments, the fusion protein may comprise one or more thermally responsive polypeptides, the thermally responsive polypeptide having a transition temperature such that the fusion protein remains soluble prior to administration and such that the fusion protein transitions upon administration to a gel-like depot in the subject. In some embodiments, the fusion protein may comprise one or more thermally responsive polypeptides, the thermally responsive polypeptide having a transition temperature such that the fusion protein remains soluble at room temperature and such that the fusion protein transitions upon administration to a gel-like depot in the subject. For example, in some embodiments, the fusion protein may comprise one or more thermally responsive polypeptides, the thermally responsive polypeptide having a transition temperature between room temperature (about 25° C.) and body temperature (about 37° C.), whereby the fusion protein can be administered to form a depot. As used herein, "depot" refers to a gel-like composition comprising a fusion protein that releases the fusion protein over time. In some embodiments, the fusion protein can be injected subcutaneously or intratumorally to form a depot (coacervate). The depot may provide controlled and/or slow release of the fusion protein. The depot may provide slow release of the fusion protein into the circulation or the tumor, for example. In some embodiments, the fusion protein may be released from the depot over a period of at least 1 day, at least 2 days, at least 3 days, at least 4 days, at least 5 days, at least 6 days, at least 7 days, at least 1 week, at least 1.5 weeks, at least 2 weeks, at least 2.5 weeks, at least 3.5 weeks, at least 4 weeks, or at least 1 month.

5. Detection

As used herein, the term "detect" or "determine the presence of" refers to the qualitative measurement of undetectable, low, normal, or high concentrations of one or more fusion proteins, targets, or fusion proteins bound to target. Detection may include in vitro, ex vivo, or in vivo detection. Detection may include detecting the presence of one or more fusion proteins or targets versus the absence of the one or more fusion proteins or targets. Detection may also include quantification of the level of one or more fusion proteins or targets. The term "quantify" or "quantification" may be used interchangeably, and may refer to a process of determining the quantity or abundance of a substance (e.g., fusion protein or target), whether relative or absolute. Any suitable method of detection falls within the general scope of the present disclosure. In some embodiments, the fusion protein may comprise a reporter attached thereto for detection. In some embodiments, the fusion protein may be labeled with a reporter. In some embodiments, detection of fusion protein bound to target may be determined by methods including but not limited to, band intensity on a Western blot, flow cytometry, radiolabel imaging, cell binding assays, activity assays, surface plasmon resonance (SPR), immunoassay, or by various other methods known in the art.

In some embodiments, including those wherein the fusion protein is an antibody mimic for binding and/or detecting a target, any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the fusion protein to the target can be detected via direct labels, attached to the fusion protein or via indirect labels, such as alkaline phosphatase or horseradish peroxidase. The use of immobilized fusion proteins may be incorporated into the immunoassay. The fusion proteins may be immobilized onto a variety of supports, such as magnetic or chromatographic matrix particles, the surface of an assay plate (such as microtiter wells), pieces of a solid substrate material, and the like. An assay strip can be prepared by coating the fusion protein or plurality of fusion proteins in an array on a solid support. This strip can then be dipped into the test biological sample and then processed quickly through washes and detection steps to generate a measurable signal, such as a colored spot.

6. Methods a. Methods of Treating a Disease

In another aspect, disclosed are methods of treating a disease in a subject in need thereof. The method may comprise administering to the subject an effective amount of the fusion protein as described herein. The disease may be selected from cancer, metabolic disease, autoimmune disease, cardiovascular disease, and orthopedic disorders. In some embodiments, the disease may be a disease associated with a target of the at least one binding polypeptide.

Metabolic disease may occur when abnormal chemical reactions in the body alter the normal metabolic process. Metabolic diseases may include, for example, insulin resistance, non-alcoholic fatty liver diseases, type 2 diabetes, insulin resistance diseases, cardiovascular diseases, arteriosclerosis, lipid-related metabolic disorders, hyperglycemia, hyperinsulinemia, hyperlipidemia, and glucose metabolic disorders.

Autoimmune diseases may arise from an abnormal immune response of the body against substances and tissues normally present in the body. Autoimmune diseases may include, but are not limited to, lupus, rheumatoid arthritis, multiple sclerosis, insulin dependent diabetes mellitis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, polyarteritis nodosa, myocarditis, psoriasis, Celiac disease, Crohn's disease, ulcerative colitis, and fibromyalgia.

Cardiovascular disease is a class of diseases that involve the heart or blood vessels. Cardiovascular diseases may include, for example, coronary artery diseases (CAD) such as angina and myocardial infarction (heart attack), stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

Orthopedic disorders or musculoskeletal disorders are injuries or pain in the body's joints, ligaments, muscles, nerves, tendons, and structures that support limbs, neck, and back. Orthopedic disorders may include degenerative diseases and inflammatory conditions that cause pain and impair normal activities. Orthopedic disorders may include, for example, carpal tunnel syndrome, epicondylitis, and tendinitis.

Cancers may include, but are not limited to, breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. In some embodiments, the cancer may be colorectal cancer. In some embodiments, the cancer may be colorectal adenocarcinoma.

In some embodiments, the present disclosure provides a method for using scaffold proteins in developing antibody mimetics for oncological targets of interest. With the emergence of scaffold protein engineering come the possibilities for designing potent protein drugs that are unhindered by steric and architectural limitations. Although potent protein drugs can be useful for diagnostics or treatments, successful delivery to the target region can pose a great challenge.

b. Methods of Diagnosing a Disease

In another aspect, disclosed are methods of diagnosing a disease. The methods may include administering to the subject a fusion protein as described herein, and detecting binding of the fusion protein to a target to determine presence of the target in the subject. The presence of the target may indicate the disease in the subject. In some embodiments, the methods may include contacting a sample from the subject with a fusion protein as described herein, determining the level of a target in the sample, and comparing the level of the target in the sample to a control level of the target, wherein a level of the target different from the control level indicates disease in the subject. In some embodiments, the disease may be selected from cancer, metabolic disease, autoimmune disease, cardiovascular disease, and orthopedic disorders, as detailed above. In some embodiments, the target may comprise a disease marker or biomarker. In some embodiments, the fusion protein may act as an antibody mimic for binding and/or detecting a target.

c. Methods of Determining the Presence of a Target

In another aspect, disclosed are methods of determining the presence of a target in a sample. The methods may include contacting the sample with a fusion protein as described herein under conditions to allow a complex to form between the fusion protein and the target in the sample, and detecting the presence of the complex. Presence of the complex may be indicative of the target in the sample. In some embodiments, the fusion protein may be labeled with a reporter for detection.

In some embodiments, the sample may be obtained from a subject and the method may further include diagnosing, prognosticating, or assessing the efficacy of a treatment of the subject. When the method includes assessing the efficacy of a treatment of the subject, then the method may further include modifying the treatment of the subject as needed to improve efficacy.

d. Methods of Determining the Effectiveness of a Treatment

In another aspect, disclosed are methods of determining the effectiveness of a treatment for a disease in a subject in need thereof. The methods may include contacting a sample from the subject with a fusion protein as detailed herein under conditions to allow a complex to form between the fusion protein and a target in the sample, determining the level of the complex in the sample, wherein the level of the complex is indicative of the level of the target in the sample, and comparing the level of the target in the sample to a control level of the target, wherein if the level of the target is different from the control level, then the treatment is determined to be effective or ineffective in treating the disease.

Time points may include prior to onset of disease, prior to administration of a therapy, various time points during administration of a therapy, after a therapy has concluded, or a combination thereof. Upon administration of the fusion protein to the subject, the fusion protein may bind a target, wherein the presence of the target indicates the presence of the disease in the subject at the various time points. In some embodiments, the target may comprise a disease marker or biomarker. In some embodiments, the fusion protein may act as an antibody mimic for binding and/or detecting a target. Comparison of the binding of the fusion protein to the target at various time points may indicate whether the disease has progressed, whether the diseased has advanced, whether a therapy is working to treat or prevent the disease, or a combination thereof.

In some embodiments, the control level may correspond to the level in the subject at a time point before or during the period when the subject has begun treatment, and the sample is taken from the subject at a later time point. In some embodiments, the sample may be taken from the subject at a time point during the period when the subject is undergoing treatment, and the control level corresponds to a disease-free level or to the level at a time point before the period when the subject has begun treatment. In some embodiments, the method may further include modifying the treatment or administering a different treatment to the subject when the treatment is determined to be ineffective in treating the disease.

7. Examples

Example 1

Identification of Non-Repetitive Unstructured Polypeptides

Non-repetitive permutated versions of ELPs were produced and examined. A computer algorithm was used to identify sequences comprising 200 or 400 amino acids, each with the same amino acid composition as the ELP counterpart, but with permutated or re-arranged ordering of the amino acids. The generated sequences were sufficiently non-repetitive, as they were rejected if they contained at least one subsequence comprising 5 to 10 amino acids that (a) contained three contiguous identical amino acids, (b) occurred more than once within the sequence, or (c) contained at least 2 prolines (P) separated by zero or more amino acids that are not glycine (G). These constraints promoted well-distributed prolines (P) and glycines (G) which have together been identified as structure-breaking residues.

Figure 2:
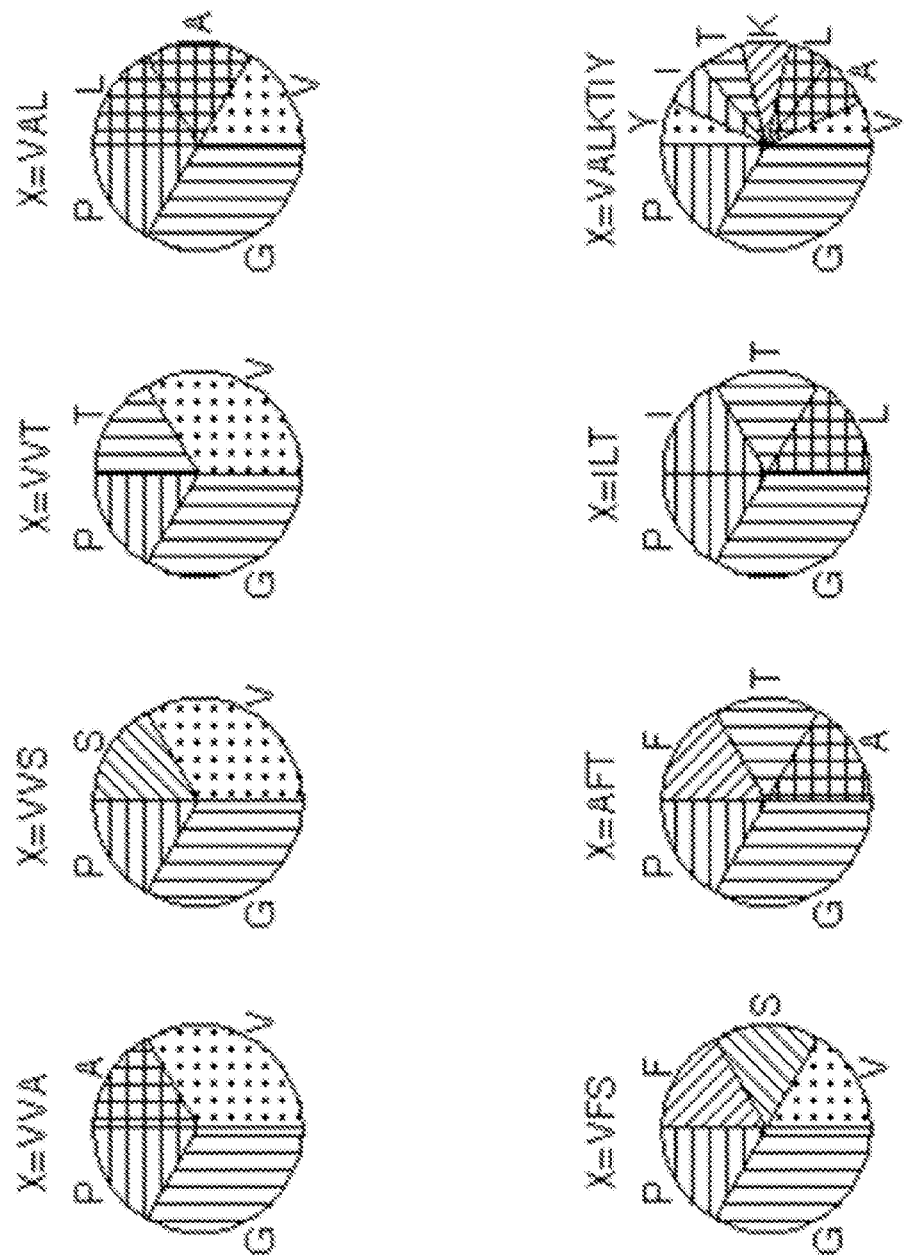
FIG. 2 is a diagram showing the amino acid compositions of exemplary non-repetitive unstructured polypeptides (SEQ ID NOs: 11-18). Each non-repetitive unstructured polypeptide comprises 240 amino acids. Each amino acid sequence comprises approximately ⅙ proline (P) residues, approximately ⅓ glycine (G) residues, and approximately ½ X residues, where X is one or more amino acids selected from the group consisting of valine (V), alanine (A), leucine (L), lysine (K), threonine (T), isoleucine (I), tyrosine (Y), serine (S), and phenylalanine (F). Each of the selected amino acids for X can occur at equal frequencies to each other (SEQ ID NOs: 11-18).
Figure 3A:
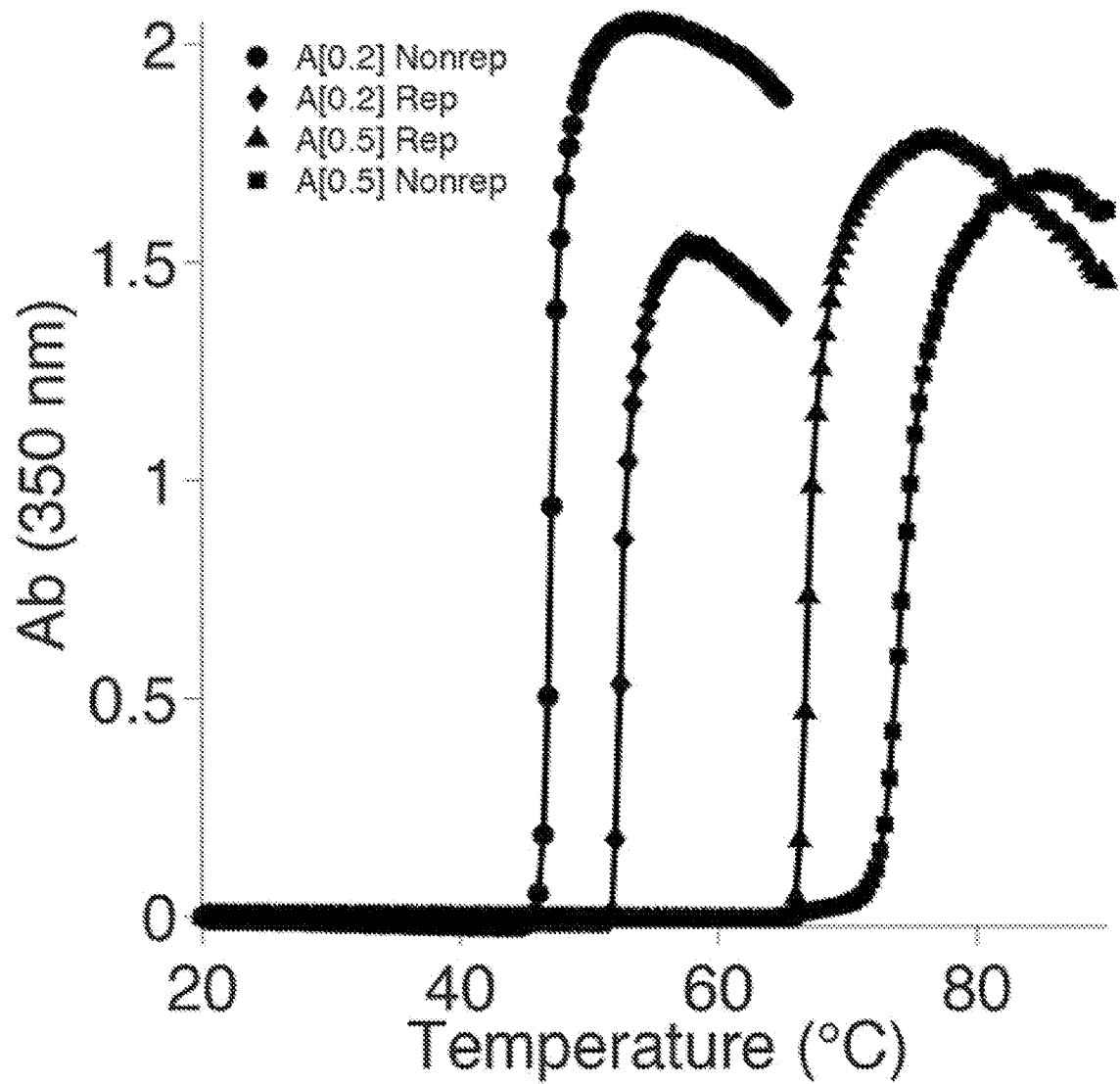
FIG. 3(A)-(B) are graphs showing the characterization of the transition temperatures of the repetitive (SEQ ID NOs: 3-6) and exemplary non-repetitive polypeptides (SEQ ID NOs: 7-10).
Figure 3B:
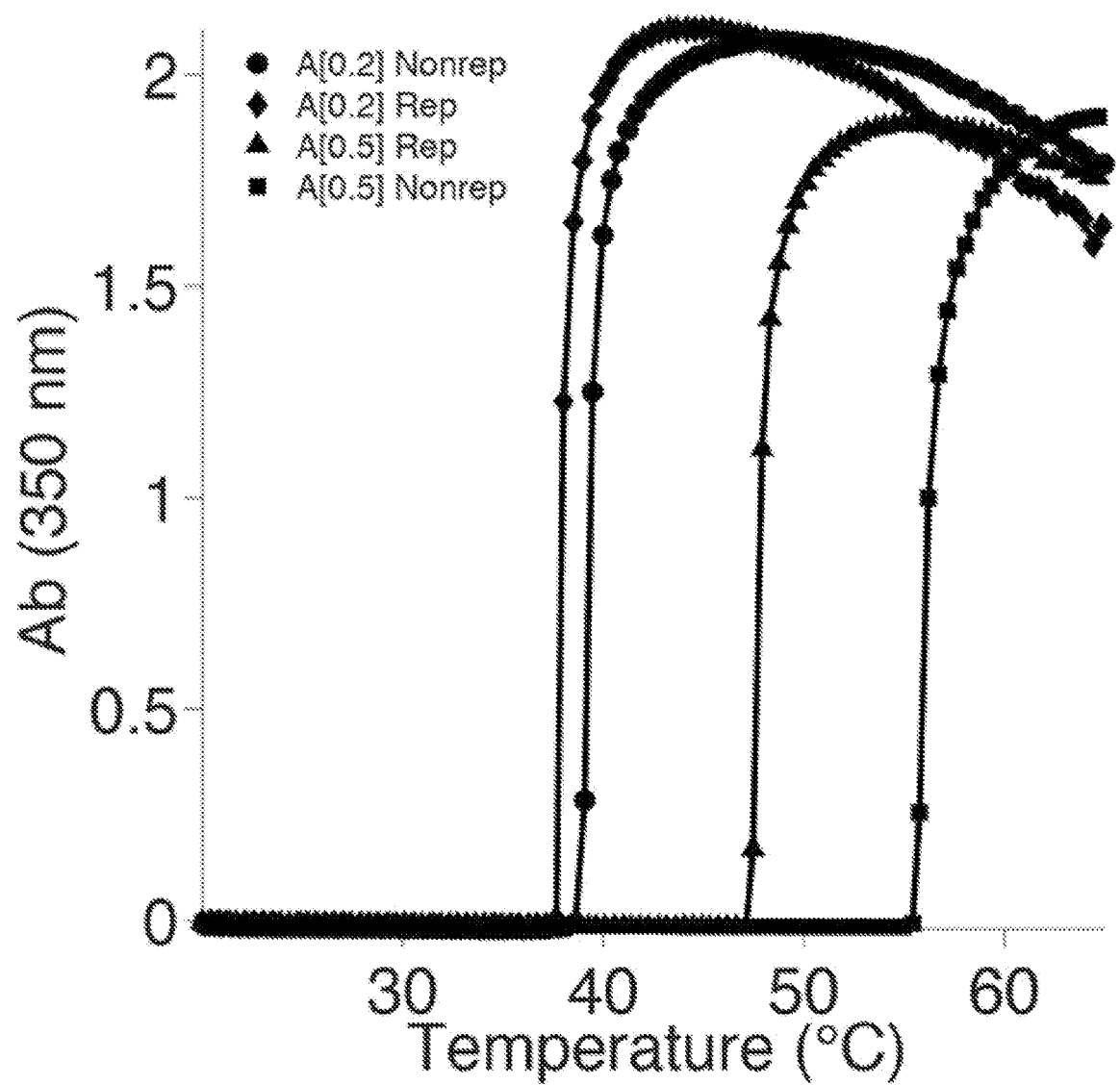
Figure 4A:
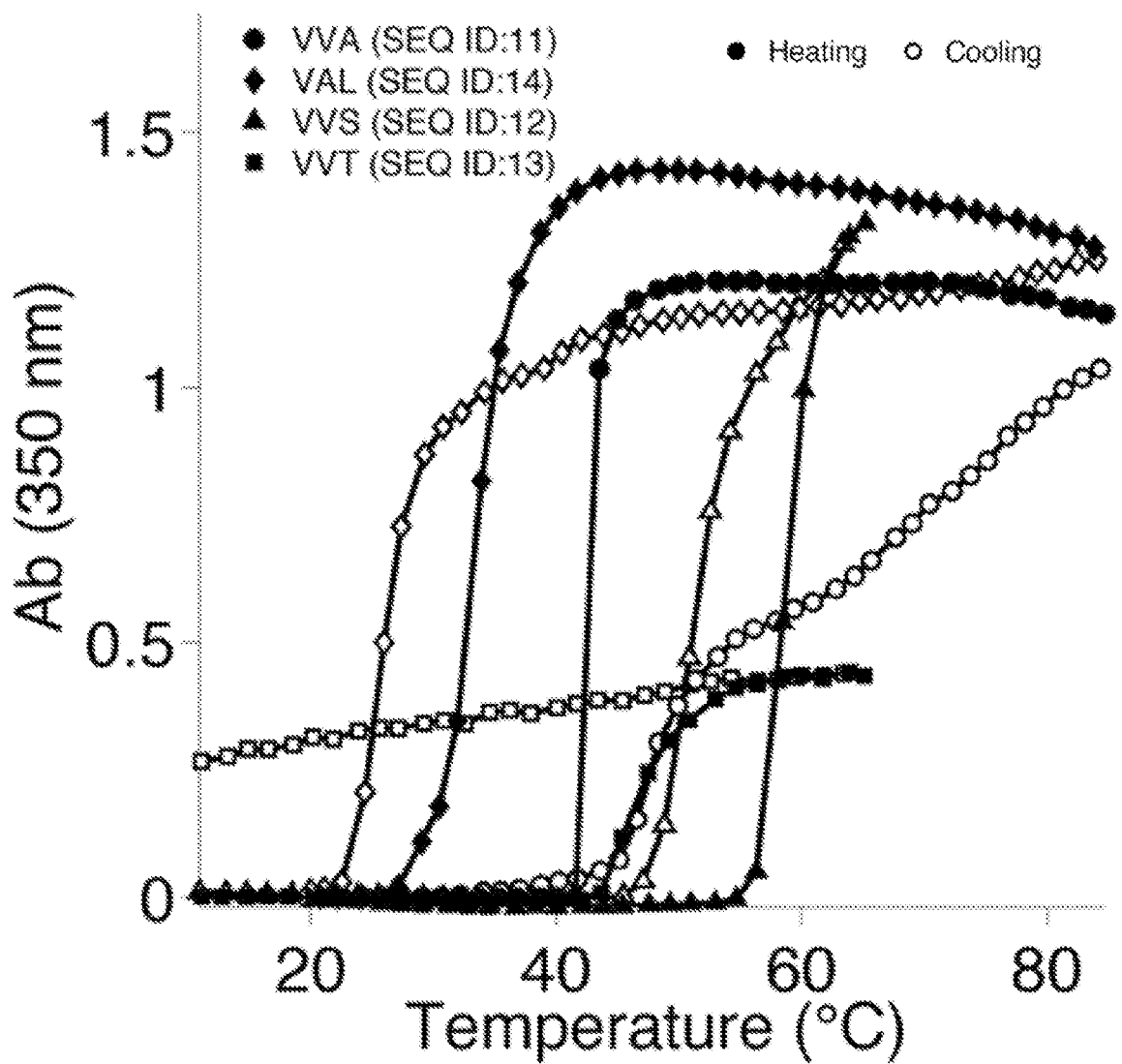
FIG. 4(A)-(B) are graphs showing transition temperature characterization of exemplary non-repetitive unstructured polypeptides (SEQ ID NOs: 11-18).
Figure 4B:
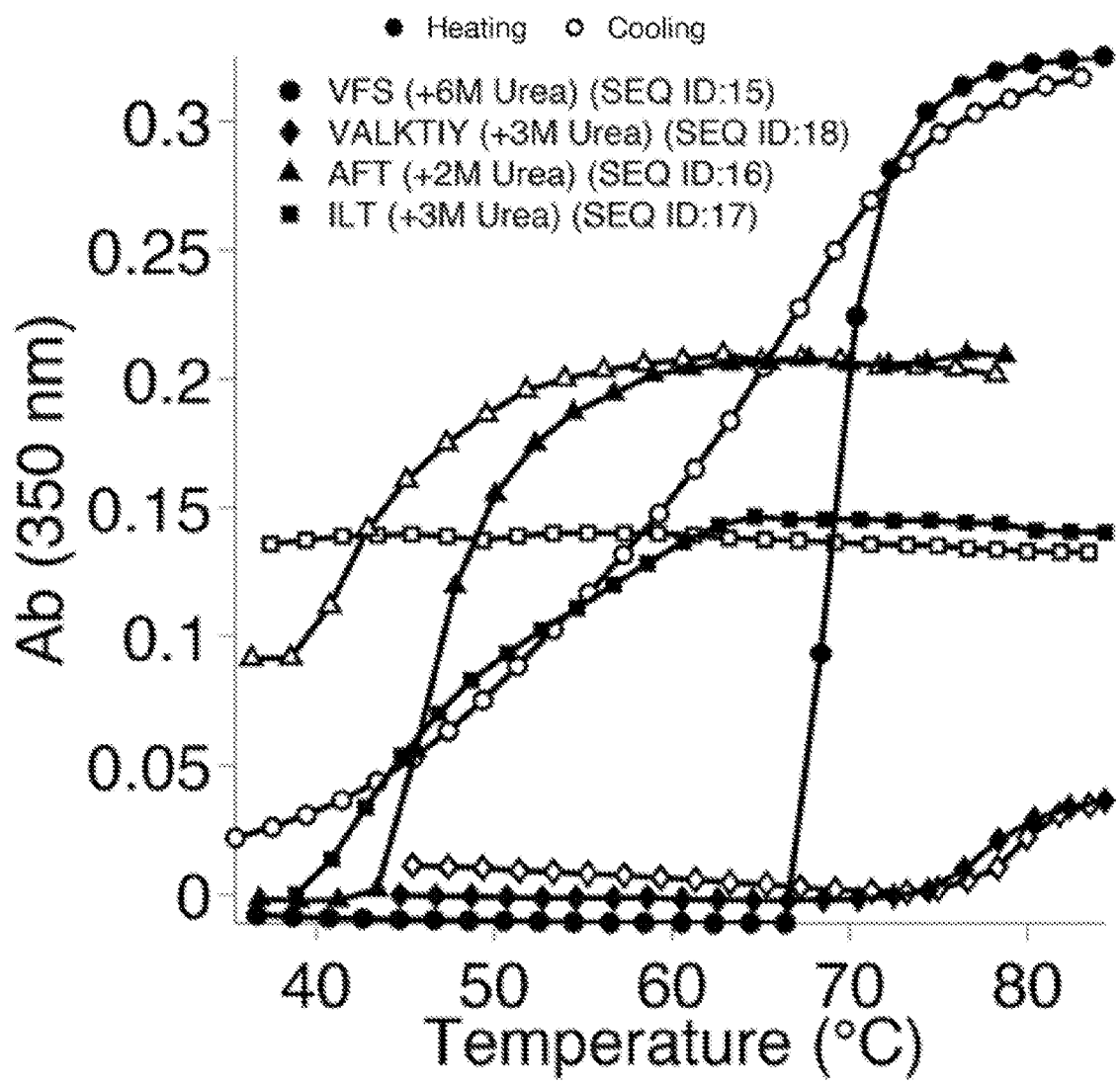

The algorithm was used to additionally identify a panel of 8 non-repetitive sequences, each comprising 240 amino acids with ⅙ being proline (P) and ⅓ being glycine (G). The remaining amino acids were various combinations of 9 different amino acids found in elastin. The amino acid compositions of these sequences are depicted in FIG. 2.

The repetitiveness of each of the unstructured polypeptide sequences was quantified by calculating linguistic complexity scores. Linguistic complexity is defined by the total number of unique subsequences in a given sequence divided by the total number of unique subsequences possible for the same alphabet and window. Scores were calculated using the protein analysis tool, CIDER (see Holehouse et al. (2015) Biophys J., which is incorporated by reference herein in its entirety). The window length was set equal to the total sequence length for each sequence. The final score is given as the product of the linguistic complexity score and total sequence length to account for sequence length. The resulting final scores for the repetitive polypeptide sequences in SEQ ID NOs: 3-6 and non-repetitive polypeptide sequences in SEQ ID NOs: 7-18 are reported in Table 1. All final scores for the non-repetitive polypeptide sequences were greater than 15.0.

TABLE 1

Characterization of the repetitiveness of repetitive (SEQ ID NOs: 3-6) and non-repetitive (SEQ ID NOs: 7-18) polypeptide sequences

| SEQ ID NO | Product of length and linguistic complexity score |
| --- | --- |
| 3 | 7.9 |
| 4 | 7.9 |
| 5 | 8.0 |
| 6 | 8.0 |
| 7 | 28.7 |
| 8 | 35.6 |
| 9 | 32.8 |
| 10 | 42.8 |
| 11 | 50.6 |
| 12 | 51.6 |
| 13 | 50.6 |
| 14 | 83.3 |
| 15 | 85.3 |
| 16 | 88.3 |
| 17 | 86.3 |
| 18 | 147.8 |

Example 2

Expression of Non-Repetitive Unstructured Polypeptides

All nucleotide sequences, unless indicated, were back-translated from amino acid sequences using codon scrambling (see Tang, N. C. et al. (2016) Nature Mater., which is incorporated by reference herein in its entirety). A N-terminal leader sequence encoding for Met-Ser-Lys-Gly-Pro-Gly (SEQ ID NO: 19) and a C-terminal His-tag tail encoding for Gly-Trp-Pro (SEQ ID NO: 20) were incorporated into the genes, unless indicated. All genes were synthesized by commercial synthesis and cloned into modified pET-24a(+) plasmids (Gen9 Inc., MA, USA and Genscript Inc., NJ, USA). The resulting plasmids were transformed into BL21 competent E. coli cells.

Colonies were inoculated in 2-5 mL of Terrific Broth (TB) plus 50 µg/mL kanamycin and grown overnight at 37° C. and 250 r.p.m. One milliliter of the starter cultures was inoculated in 1 L of TB plus 50 µg/mL kanamycin and grown for 6-7 h at 37° C. and 250 r.p.m. Expression was induced by the addition of IPTG at a final concentration of 1 mM, and the cells were grown for an addition 24 h. The unstructured polypeptides were purified by inverse transition cycling (ITC) as previously described (see Christensen et al. (2009) Curr Protoc Protein Sci., which is incorporated by reference herein in its entirety).

Example 3

Characterization of Non-Repetitive Unstructured Polypeptides

To characterize the inverse transition temperature of unstructured polypeptides, the 350 nm optical densities of 25 µM peptide solutions were monitored with a Cary 300 ultraviolet—visible spectrophotometer (Agilent Technologies) as a function of solution temperature. The inverse transition temperature was also monitored with the SYPRO Orange dye, whose fluorescence increases with the increasing hydrophobicity of the environment. Temperature responsive polymers exhibit phase transition due to the hydrophobic effect in aqueous solutions. Therefore, a StepOnePlus™ Real-Time PCR instrument was used to monitor fluorescence as a function of solution temperature. Inverse transition temperature was defined as the temperature at the maximum of the turbidity or fluorescence gradient.

Turbidity profiles, consisting of heating and cooling curves between about 0° C. and about 100° C., for all constructs at 25 µM in PBS show that non-repetitive versions of A[0.2] (SEQ ID NOs: 7 and 9) and A[0.5] (SEQ ID NOs: 8 and 10), retain LCST phase behavior with transition temperatures similar to their repetitive counterparts (SEQ ID NOs: 3 and 5 and SEQ ID NOs: 4 and 6). In addition, the unstructured polypeptides exhibited lower critical solution temperature (LCST) behaviors between 0° C. and 100° C. (see FIGS. 3(A)-(B) and FIGS. 4(A)-(B)).

SEQUENCES

Repeated subsequences

SEQ ID NO: 1
A[0.5]:
GAGVPGVGVP

SEQ ID NO: 2
A[0.2]:
GVGVPGVGVPGAGVPGVGVPGVGVP

Repetitive polypeptides of A[0.5] and A[0.2]

SEQ ID NO: 3
A[0.2] rep, 200 amino acids:
(GVGVPGVGVPGAGVPGVGVPGVGVP)$_8$

SEQ ID NO: 4
A[0.5] rep, 200 amino acids:
(GAGVPGVGVP)$_{20}$

SEQ ID NO: 5
A[0.2] rep, 400 amino acids:
(GVGVPGVGVPGAGVPGVGVPGVGVP)$_{16}$

SEQ ID NO: 6
A[0.5] rep, 400 amino acids:
(GAGVPGVGVP)$_{40}$

Non-repetitive polypeptides with permutations of A[0.5] and A[0.2]

SEQ ID NO: 7
A[0.2] nonrep, 200 amino acids:
PGGGVPGGVPGAVPGVPGAVVPVVGGVPGVVGVPGGVVPVGVVVPGVPVGV
PGVPVVGGGVPAGGVVPGGGVPVGGGVVPGVGVVPGGVPVVVGGGVGVPGV

| SEQUENCES |
|---|
| VPGVPGVGVPVGGVPGGGVVVPGGVGVPVVGVVPGAPGVPGVPGGVGGVPV<br>GVGVPGGGAPGVVPGGAVPGGAPVGGVGGGVPGVGGVPGAPGGVPGG<br><br>SEQ ID NO: 8<br>A[0.5] nonrep, 200 amino acids:<br>PGGVPGVPAGGGAGVPGVPGAPAGGGAPGVAPGGVVPGVPGVAPVVGGGAP<br>GGVPGAVPGVPGGVPGGVVVPGGGVGAPGGVAPVGGGVPVVGGVPVGGVAP<br>GVPVGVPGVGVGVPVGGGVGGVPGVVPAGVPGGGVAGVVPVGGVPVVVG<br>APGGGVGVPGAPGAGGVPGGAPGAPGVVAPGGVPVGVVVPGVVPGGG<br><br>SEQ ID NO: 9<br>A[0.2] nonrep, 400 amino acids:<br>PGGVPGVGGGVPGVPGAPGVVPGVVVPGGVVPVGGVPGVPVVGGGVPVGGG<br>VGGVPGAPGGGVPGAPVGGVPVGGVVPGVGVPGAGGGVPGGVGVVPVGGGA<br>PGGVPGVVPGVPVGGVPAGVVPGGVGVGGGVVPGVVGPGGGVGGGVGVPG<br>GAPGGGVVGGGVPGGGVVPVVGGVPGAVPGVPGVVVPVGGGVVPVGVPGGV<br>VVPGVPGGVVGVPVVGVPGVGVVPGVPGVPVGVVVPGVVPGVGVPGVP<br>GGGVPGVGVPVGGAPGVPGVPGVAVPGVVPGGAPGVPVGVVPVGVVPGGGV<br>GVVPGGVPGGVPGVPAGVPVGVPVGGVGGVVPGGGAPGVGVGVPAGVPGGV<br>PVGVGGVPGGVVPGVPAGGGVPGVPGVGGVPVGAPGVPGGVP<br><br>SEQ ID NO: 10<br>A[0.5] nonrep, 400 amino acids:<br>PAGAVPGGVPVAGGVPVGAGVVAPGAPVGGAPGVVGVPGGGVPGVPVVGVG<br>VGVPVGGGVGVVPAGGGAPGGVGVVVPGVVPGAPAGGVPGVAPGGVGGVPG<br>VVPGGGVVPGVAPGVPGVPGGVPGVPVGAAPGGVPAVGVPGVGGGVPVV<br>GAGAPGGVPGVAVPGAPGGVPVGGVPGGGVGGVVPGGVPGAPVGVVPGVGV<br>VPGVPAGVGVPGAPGAPGGGVPGGGAPVGGAGGVPGGVPGVPGAPGVGVPG<br>VGVPVGVPGVPGVPVGGGAGVPGGVAPGVAVPGGVGVPVVGGVPGAVPGVP<br>GVGGAPGVPGGGVVGVGVPGGVVPGVPGAGAPGGGAPGAPVGVPGGAPGVV<br>PGVGGVPGAGGGVVGGGVVPVGGGVVPGAPGGAPVGGVVGGVP<br><br>Non-repetitive polypeptides:<br>Each amino acid sequence comprises 1/6 proline (P)<br>residues, 1/3 glycine (G) residues, and 1/2 X<br>residues, where X is one or more amino acids<br>selected from the group consisting of valine (V),<br>alanine (A), leucine (L), lysine (K), threonine<br>(T), isoleucine (I), tyrosine (Y), serine (S), and<br>phenylalanine (F). Each of the selected amino<br>acids for X occurs at equal frequencies to each<br>other.<br><br>SEQ ID NO: 11<br>PVGVPGVGGAPVVVGGAPVGVGGAGGVVPGAPVGAVAGVGAPGGAVPAGGA<br>PGVGAPGVVPGAVPGVGVGGGVVVPVVVGVGGVPAGAVPGVGGVAPVGV<br>PVGAGGGAPAGGVPVAVGVPVVGGGVPGVGVVGVAPGAPGAGVGVVAGAGA<br>AAVAPVGVAPGVPGVPGAVVGVPGGVAPAVVVGAVPGVVGVVVPVGAPVVAG<br>GVAVAPVGGAVPGVPGGVPGGGAPGAPVVGVPVGVP<br><br>SEQ ID NO: 12<br>PVGSPGSVPGVVPVSGVVGGGSVPGSSPVVGVPSGVPVGSPVVGGGVSPG<br>VGVPGVVVPGVPVGGGVGVPGGGVVGGVPVVVGVSVPSGVSPGGGVVVPVG<br>SVSSGVPVVSVVGVSVVPGSVPVGSPSSGVPGVVPGSPGGVVGSSVPSGSG<br>GVSVPVGVGGSGVPGVPGSGSVVPVGVSPVGGGSGSGVGSGSPGGSVPGGS<br>PGVVPVGSPGVGGVPGVVGGSGSPGVPGGVGVGVPG | SEQ ID NO: 13<br>PVGTPGTVPGGVVPVGVTPVGGGTGTPTTVTVVGGVVVPGVPGGGTPGVPV<br>GTPVVGGVGVGTGTPGGTVPGGTPGVVPGTPGGVVPGTTVPTGTGTTPVVG<br>VPTVGGVTPGVGGVPVVVGTGVPGVPVGGGVGVVGVVVPGTVPVGVPGVVG<br>GTVPVGTPTTGVPGVVPTGVTPGGVGVPGGGVVGGVVPGVTVPGTVTTGV<br>PVVTVGVVVPVGTVGGVVVGGGTTPGGVPGTPGVGG<br><br>SEQ ID NO: 14<br>GAVVVPGGAVGVPAGAVGGVGGVLVPAVGAVPGGGVPAVGVPVAGVVPGGL<br>PGGAGVGALGAAAPGGVPVGAALPGVAGVAPGGGLPGLGAGAGLGLAGALV<br>LPGLGGGVPGVPGGGLLPGGVPLLGLPGVPAGLPGVLPVGLLLPGAPGVPAL<br>GVPLGVPGVAPGLPGAGGLPGVGAPGLLPVGGAPAALGGLGLPGGGALGLL<br>APGGALVPGVGGVAPVAAGALLPGGAPLGVPALLAL<br><br>SEQ ID NO: 15<br>SSGSSGSGFFSGGVPSGGGVVFVPSFFGFFPSGSGGVVPGVPGGGVGVPGF<br>VGVPVGGFPVGVPGVFVPSVVGVPGFFVFPGVPGGSSSPGSPFGVFGGGSS<br>GGGFPFGSSPGVVVSPGFGFGVPFGVPVGGSVFFFPFGGGFPGGFPSGSFG<br>VPGGGFVVPFGVSPGSPGFVPSFGSPGGFGGFSPFSSGVGSPGGVPGVGVV<br>SPGFPGGSPFGFPGSPGGSFGGSPSVFGSGSPGSFP<br><br>SEQ ID NO: 16<br>AAGGTGFFTGGAPGGTPTAFGGFTPFTFAGGGAPGFFAFPGAPGTFPTFGA<br>PGAAPFGTTPGTFFGFPGGTPGTPGAATPGFFGAFGFPGAFATFGFPGGGA<br>GAAPAGTPGAPTAAGATTPGAGGTTGGAPTGGGFAPTFFGFFPTGTGGAAP<br>GAPGGGTTTFPGATPFGFPGTGTPGTFGAPGGGFFPGAGFGGGAPGAPAAA<br>GGGTPGTATPGTFPTGAGTFPGTFPFGGGFPGGFPT<br><br>SEQ ID NO: 17<br>TILPGIGLPGGLPLTIGGILPILLGTTIGGIPGGGIIPGIGGGIPILTLLI<br>LPTGLPGTPLTTGTPGITGLGTPLGIGLIGTGIPGGGTGIPTGIPGTTLPG<br>IPTLGGGIPLIGTPGGIGTIGIPGTGTIIGIPGGGLLLIPGITLPIGLPGG<br>TPGTPGGGTGTTPTGLPGILLPGGLPGIPTGTPGTGTPIGGLLILLTLPGL<br>PGLGLPGLIPLGTGLTGGTPTGGIPGGIGIPGILTT<br><br>SEQ ID NO: 18<br>PGTYPGYGYVVPPTTGGIPGGVVPGGGTKLVPGKGKGGAKAPGTVPVGAGGG<br>KIVPIYGIAPGKYGYPGGGIVPGITTPGLPTGKKPYGGVPVLYGKLPGAPG<br>IPTAGAPGYIAPGVPGGLVKGGTGIAPLGVILVYIGVGGIKGGALPTGGLY<br>PGAGTPGYPVGGGAPAGGIALKPGITPGTAAPGLPGKGGKYTYPGGAPGGT<br>GGVPGYPGLALKLGIPTKGGGIGLPYIGLLPGKPGG<br><br>SEQ ID NO: 19<br>Met-Ser-Lys-Gly-Pro-Gly<br><br>SEQ ID NO: 20<br>Gly-Trp-Pro<br><br>SEQ ID NO: 21<br>(Gly$_4$Ser)$_3$<br><br>SEQ ID NO: 22<br>PQPQPKPQPKPEPEPQPQG<br><br>SEQ ID NO: 23<br>(VPGXG)$_n$, wherein X is any amino acid except proline and n is an integer greater than or equal to 1 |

What is claimed is:

1. An unstructured polypeptide, wherein the polypeptide is soluble below the lower critical solution temperature (LCST), soluble above the upper critical solution temperature (LCST), or a combination thereof, wherein the LCST and UCST are each independently from about 0° C. to about 100° C., wherein any 5-10 amino acid subsequence does not occur more than once in the unstructured polypeptide, and wherein the unstructured polypeptide comprises a sequence of at least 50 amino acids, wherein at least 10% of the amino acids are proline (P) and at least 20% of the amino acids are glycine (G).

2. The unstructured polypeptide of claim 1, wherein the LCST and UCST are each independently from about 25° C. to about 37° C.

3. The unstructured polypeptide of claim 1, wherein the unstructured polypeptide comprises a sequence wherein at least 40% of the amino acids are selected from the group consisting of valine (V), alanine (A), leucine (L), lysine (K), threonine (T), isoleucine (I), tyrosine (Y), serine (S), and phenylalanine (F).

4. The unstructured polypeptide of claim 1, wherein the unstructured polypeptide has a linguistic complexity score, and wherein the product of the linguistic complexity score and the amino acid sequence length of the unstructured polypeptide is greater than 15.

5. The unstructured polypeptide of claim 1, wherein the unstructured polypeptide comprises a 50 amino acid subsequence of any of SEQ ID NO: 7-18.

6. The unstructured polypeptide of claim 1, wherein the unstructured polypeptide comprises a sequence that does not contain three contiguous identical amino acids, and
wherein when the unstructured polypeptide comprises a subsequence starting and ending with proline (P), the subsequence further comprises at least one glycine (G).

7. The unstructured polypeptide of claim 1,
wherein at least 10% of the amino acids are proline (P), wherein at least 20% of the amino acids are glycine (G), wherein at least 40% of the amino acids are selected from the group consisting of valine (V), alanine (A), leucine (L), lysine (K), threonine (T), isoleucine (I), tyrosine (Y), serine (S), and phenylalanine (F),
wherein the unstructured polypeptide does not contain three contiguous identical amino acids, and
wherein when the unstructured polypeptide comprises a subsequence starting and ending with proline (P), wherein the subsequence further comprises at least one glycine (G).

8. A fusion protein comprising at least one binding polypeptide and the unstructured polypeptide of claim 1.

9. The fusion protein of claim 8, wherein the fusion protein comprises a plurality of unstructured polypeptides.

10. The fusion protein of claim 8, wherein the fusion protein comprises a plurality of binding polypeptides.

11. The fusion protein of claim 10, further comprising a linker positioned between at least two adjacent binding polypeptides, wherein the linker comprises at least one glycine and at least one serine, or the linker comprises an amino acid sequence consisting of SEQ ID NO: 22 (PQPQPKPQPKPEPEPQPQG).

12. The fusion protein of claim 9, further comprising a linker positioned between at least two adjacent unstructured polypeptides, wherein the linker comprises at least one glycine and at least one serine, or the linker comprises an amino acid sequence consisting of SEQ ID NO: 22 (PQPQPKPQPKPEPEPQPQG).

13. The fusion protein of claim 11, wherein the linker comprises an amino acid sequence consisting of SEQ ID NO: 21 ((Gly$_4$Ser)$_3$).

14. The fusion protein of claim 12, wherein the linker comprises an amino acid sequence consisting of SEQ ID NO: 21 ((Gly$_4$Ser)$_3$).

15. The fusion protein of claim 10, wherein the plurality of binding polypeptides form an oligomer.

16. The fusion protein of claim 8, wherein the binding polypeptide binds a target, and wherein the fusion protein binds more than one target, and/or wherein the binding polypeptide comprises Protein A.

17. The fusion protein of claim 8, wherein the at least one unstructured polypeptide comprises a thermally responsive polypeptide.

18. The fusion protein of claim 8, further comprising at least one linker positioned between the at least one binding polypeptide and the at least one unstructured polypeptide.

19. The fusion protein of claim 8, wherein the at least one binding polypeptide is positioned N-terminal to the at least one unstructured polypeptide or C-terminal to the at least one unstructured polypeptide.

20. The unstructured polypeptide of claim 1, wherein the unstructured polypeptide does not comprise three contiguous identical amino acids.

21. The unstructured polypeptide of claim 1, wherein the polypeptide comprises a subsequence starting with a first proline and ending with a second proline, wherein the first proline and second proline are separated by at least one glycine.

22. The fusion protein of claim 8, wherein the fusion protein has a structure selected from the group consisting of:
 (a) [binding polypeptide]$_m$-[linker]$_k$-[unstructured polypeptide];
 (b) [unstructured polypeptide]-[linker]$_k$-[binding polypeptide]$_m$;
 (c) [binding polypeptide]$_m$-[linker]$_k$-[unstructured polypeptide]-[binding polypeptide]$_m$-[linker]$_k$-[unstructured polypeptide]; and
 (d) [unstructured polypeptide]-[linker]$_k$-[binding polypeptide]$_m$-[unstructured polypeptide]-[binding polypeptide]$_m$;
 wherein m is an integer less than or equal to 20, and k is an integer less than or equal to 10.

23. A protein comprising a first unstructured polypeptide and a second unstructured polypeptide, wherein the first unstructured polypeptide is soluble below the lower critical solution temperature (LCST), soluble above the upper critical solution temperature (UCST), or a combination thereof, wherein the LCST and UCST are each independently from about 0° C. to about 100° C., wherein any 5-10 amino acid subsequence does not occur more than once in the first unstructured polypeptide, wherein the first unstructured polypeptide comprises a sequence of at least 50 amino acids, and wherein in the first unstructured polypeptide at least 10% of the amino acids are proline and at least 20% of the amino acids are glycine.

24. The protein of claim 23, wherein the LCST and UCST of the first unstructured polypeptide are each independently from about 25° C. to about 37° C.

25. The protein of claim 23 wherein the first unstructured polypeptide comprises a sequence wherein at least 40% of the amino acids are selected from the group consisting of valine (V), alanine (A), leucine (L), lysine (K), threonine (T), isoleucine (I), tyrosine (Y), serine (S), and phenylalanine (F).

26. The protein of claim 23, wherein the first unstructured polypeptide has a linguistic complexity score, and wherein the product of the linguistic complexity score and the amino acid sequence length of the first unstructured polypeptide is greater than 15.

27. The protein of claim 23, wherein the first unstructured polypeptide comprises a 50 amino acid subsequence of any of SEQ ID NO: 7-18.

28. The protein of claim 23, wherein the first unstructured polypeptide comprises a sequence that does not contain three contiguous identical amino acids; and
 wherein when the first unstructured polypeptide comprises a subsequence starting and ending with proline (P), the subsequence further comprises at least one glycine (G).

29. The protein of claim 23,
 wherein at least 10% of the amino acids of the first unstructured polypeptide are proline (P),
 wherein at least 20% of the amino acids of the first unstructured polypeptide are glycine (G),
 wherein at least 40% of the amino acids of the first unstructured polypeptide are selected from the group consisting of valine (V), alanine (A), leucine (L), lysine (K), threonine (T), isoleucine (I), tyrosine (Y), serine (S), and phenylalanine (F),
 wherein the sequence of the first unstructured polypeptide does not contain three contiguous identical amino acids, and
 wherein when the first unstructured polypeptide comprises a subsequence starting and ending with proline (P), the subsequence further comprises at least one glycine (G).

* * * * *

SEQUENCE LISTING

<160> NUMBER OF SEQ ID NOS: 23

<210> SEQ ID NO 1
<211> LENGTH: 10
<212> TYPE: PRT
<213> ORGANISM: Homo sapien

<400> SEQUENCE: 1

Gly Ala Gly Val Pro Gly Val Gly Val Pro
1               5                   10

<210> SEQ ID NO 2
<211> LENGTH: 25
<212> TYPE: PRT
<213> ORGANISM: Homo sapien

<400> SEQUENCE: 2

Gly Val Gly Val Pro Gly Val Gly Val Pro Gly Ala Gly Val Pro Gly
1               5                   10                  15

Val Gly Val Pro Gly Val Gly Val Pro
            20                  25

<210> SEQ ID NO 3
<211> LENGTH: 200
<212> TYPE: PRT
<213> ORGANISM: Homo sapien

<400> SEQUENCE: 3

Gly Val Gly Val Pro Gly Val Gly Val Pro Gly Ala Gly Val Pro Gly
1               5                   10                  15

Val Gly Val Pro Gly Val Gly Val Pro Gly Val Gly Val Pro Gly Val
            20                  25                  30

Gly Val Pro Gly Ala Gly Val Pro Gly Val Gly Val Pro Gly Val Gly
        35                  40                  45

Val Pro Gly Val Gly Val Pro Gly Val Gly Val Pro Gly Ala Gly Val
    50                  55                  60

Pro Gly Val Gly Val Pro Gly Val Gly Val Pro Gly Val Gly Val Pro
65                  70                  75                  80

Gly Val Gly Val Pro Gly Ala Gly Val Pro Gly Val Gly Val Pro Gly
                85                  90                  95

Val Gly Val Pro Gly Val Gly Val Pro Gly Val Gly Val Pro Gly Ala
            100                 105                 110

Gly Val Pro Gly Val Gly Val Pro Gly Val Gly Val Pro Gly Val Gly
        115                 120                 125

Val Pro Gly Val Gly Val Pro Gly Ala Gly Val Pro Gly Val Gly Val
    130                 135                 140

Pro Gly Val Gly Val Pro Gly Val Gly Val Pro Gly Val Gly Val Pro
145                 150                 155                 160

Gly Ala Gly Val Pro Gly Val Gly Val Pro Gly Val Gly Val Pro Gly
                165                 170                 175

Val Gly Val Pro Gly Val Gly Val Pro Gly Ala Gly Val Pro Gly Val
            180                 185                 190

Gly Val Pro Gly Val Gly Val Pro
        195                 200

<210> SEQ ID NO 4
<211> LENGTH: 200
<212> TYPE: PRT
<213> ORGANISM: Homo sapien

<400> SEQUENCE: 4

Gly Ala Gly Val Pro Gly Val Gly Val Pro Gly Ala Gly Val Pro Gly
1               5                   10                  15

Val Gly Val Pro Gly Ala Gly Val Pro Gly Val Gly Val Pro Gly Ala
            20                  25                  30

Gly Val Pro Gly Val Gly Val Pro Gly Ala Gly Val Pro Gly Val Gly
        35                  40                  45

```
Val Pro Gly Ala Gly Val Pro Gly Val Gly Val Pro Gly Ala Gly Val
        50                  55                  60

Pro Gly Val Gly Val Pro Gly Ala Gly Val Pro Gly Val Gly Val Pro
 65                  70                  75                  80

Gly Ala Gly Val Pro Gly Val Gly Val Pro Gly Ala Gly Val Pro Gly
                 85                  90                  95

Val Gly Val Pro Gly Ala Gly Val Pro Gly Val Gly Val Pro Gly Ala
            100                 105                 110

Gly Val Pro Gly Val Gly Val Pro Gly Ala Gly Val Pro Gly Val Gly
            115                 120                 125

Val Pro Gly Ala Gly Val Pro Gly Val Gly Val Pro Gly Ala Gly Val
130                 135                 140

Pro Gly Val Gly Val Pro Gly Ala Gly Val Pro Gly Val Gly Val Pro
145                 150                 155                 160

Gly Ala Gly Val Pro Gly Val Gly Val Pro Gly Ala Gly Val Pro Gly
                165                 170                 175

Val Gly Val Pro Gly Ala Gly Val Pro Gly Val Gly Val Pro Gly Ala
            180                 185                 190

Gly Val Pro Gly Val Gly Val Pro
            195                 200

<210> SEQ ID NO 5
<211> LENGTH: 400
<212> TYPE: PRT
<213> ORGANISM: Homo sapien

<400> SEQUENCE: 5

Gly Val Gly Val Pro Gly Val Gly Val Pro Gly Ala Gly Val Pro Gly
 1               5                  10                  15

Val Gly Val Pro Gly Val Gly Val Pro Gly Val Gly Val Pro Gly Val
             20                  25                  30

Gly Val Pro Gly Ala Gly Val Pro Gly Val Gly Val Pro Gly Val Gly
             35                  40                  45

Val Pro Gly Val Gly Val Pro Gly Val Gly Val Pro Gly Ala Gly Val
 50                  55                  60

Pro Gly Val Gly Val Pro Gly Val Gly Val Pro Gly Val Gly Val Pro
 65                  70                  75                  80

Gly Val Gly Val Pro Gly Ala Gly Val Pro Gly Val Gly Val Pro Gly
                 85                  90                  95

Val Gly Val Pro Gly Val Gly Val Pro Gly Val Gly Val Pro Gly Ala
            100                 105                 110

Gly Val Pro Gly Val Gly Val Pro Gly Val Gly Val Pro Gly Val Gly
            115                 120                 125

Val Pro Gly Val Gly Val Pro Gly Ala Gly Val Pro Gly Val Gly Val
130                 135                 140

Pro Gly Val Gly Val Pro Gly Val Gly Val Pro Gly Val Gly Val Pro
145                 150                 155                 160

Gly Ala Gly Val Pro Gly Val Gly Val Pro Gly Val Gly Val Pro Gly
                165                 170                 175

Val Gly Val Pro Gly Val Gly Val Pro Gly Ala Gly Val Pro Gly Val
            180                 185                 190

Gly Val Pro Gly Val Gly Val Pro Gly Val Gly Val Pro Gly Val Gly
            195                 200                 205

Val Pro Gly Ala Gly Val Pro Gly Val Gly Val Pro Gly Val Gly Val
210                 215                 220
```

Pro Gly Val Gly Val Pro Gly Val Gly Val Pro Ala Gly Val Pro
225                 230                 235                 240

Gly Val Gly Val Pro Gly Val Gly Val Pro Gly Val Gly Val Pro Gly
            245                 250                 255

Val Gly Val Pro Gly Ala Gly Val Pro Gly Val Gly Val Pro Gly Val
        260                 265                 270

Gly Val Pro Gly Val Gly Val Pro Gly Val Gly Val Pro Gly Ala Gly
    275                 280                 285

Val Pro Gly Val Gly Val Pro Gly Val Gly Val Pro Gly Val Gly Val
290                 295                 300

Pro Gly Val Gly Val Pro Gly Ala Gly Val Pro Gly Val Gly Val Pro
305                 310                 315                 320

Gly Val Gly Val Pro Gly Val Gly Val Pro Gly Val Gly Val Pro Gly
            325                 330                 335

Ala Gly Val Pro Gly Val Gly Val Pro Gly Val Gly Val Pro Gly Val
        340                 345                 350

Gly Val Pro Gly Val Gly Val Pro Gly Ala Gly Val Pro Gly Val Gly
    355                 360                 365

Val Pro Gly Val Gly Val Pro Gly Val Gly Val Pro Gly Val Gly Val
370                 375                 380

Pro Gly Ala Gly Val Pro Gly Val Gly Val Pro Gly Val Gly Val Pro
385                 390                 395                 400

<210> SEQ ID NO 6
<211> LENGTH: 400
<212> TYPE: PRT
<213> ORGANISM: Homo sapien

<400> SEQUENCE: 6

Gly Ala Gly Val Pro Gly Val Gly Val Pro Gly Ala Gly Val Pro Gly
1               5                   10                  15

Val Gly Val Pro Gly Ala Gly Val Pro Gly Val Gly Val Pro Gly Ala
            20                  25                  30

Gly Val Pro Gly Val Gly Val Pro Gly Ala Gly Val Pro Gly Val Gly
        35                  40                  45

Val Pro Gly Ala Gly Val Pro Gly Val Gly Val Pro Gly Ala Gly Val
    50                  55                  60

Pro Gly Val Gly Val Pro Gly Ala Gly Val Pro Gly Val Gly Val Pro
65                  70                  75                  80

Gly Ala Gly Val Pro Gly Val Gly Val Pro Gly Ala Gly Val Pro Gly
            85                  90                  95

Val Gly Val Pro Gly Ala Gly Val Pro Gly Val Gly Val Pro Gly Ala
        100                 105                 110

Gly Val Pro Gly Val Gly Val Pro Gly Ala Gly Val Pro Gly Val Gly
    115                 120                 125

Val Pro Gly Ala Gly Val Pro Gly Val Gly Val Pro Gly Ala Gly Val
130                 135                 140

Pro Gly Val Gly Val Pro Gly Ala Gly Val Pro Gly Val Gly Val Pro
145                 150                 155                 160

Gly Ala Gly Val Pro Gly Val Gly Val Pro Gly Ala Gly Val Pro Gly
            165                 170                 175

Val Gly Val Pro Gly Ala Gly Val Pro Gly Val Gly Val Pro Gly Ala
        180                 185                 190

Gly Val Pro Gly Val Gly Val Pro Gly Ala Gly Val Pro Gly Val Gly

```
            195                 200                 205
Val Pro Gly Ala Gly Val Pro Gly Val Gly Val Pro Gly Ala Gly Val
210                 215                 220

Pro Gly Val Gly Val Pro Gly Ala Gly Val Pro Gly Val Gly Val Pro
225                 230                 235                 240

Gly Ala Gly Val Pro Gly Val Gly Val Pro Gly Ala Gly Val Pro Gly
                245                 250                 255

Val Gly Val Pro Gly Ala Gly Val Pro Gly Val Gly Val Pro Gly Ala
                260                 265                 270

Gly Val Pro Gly Val Gly Val Pro Gly Ala Gly Val Pro Gly Val Gly
                275                 280                 285

Val Pro Gly Ala Gly Val Pro Gly Val Gly Val Pro Gly Ala Gly Val
            290                 295                 300

Pro Gly Val Gly Val Pro Gly Ala Gly Val Pro Gly Val Gly Val Pro
305                 310                 315                 320

Gly Ala Gly Val Pro Gly Val Gly Val Pro Gly Ala Gly Val Pro Gly
                325                 330                 335

Val Gly Val Pro Gly Ala Gly Val Pro Gly Val Gly Val Pro Gly Ala
                340                 345                 350

Gly Val Pro Gly Val Gly Val Pro Gly Ala Gly Val Pro Gly Val Gly
                355                 360                 365

Val Pro Gly Ala Gly Val Pro Gly Val Gly Val Pro Gly Ala Gly Val
            370                 375                 380

Pro Gly Val Gly Val Pro Gly Ala Gly Val Pro Gly Val Gly Val Pro
385                 390                 395                 400

<210> SEQ ID NO 7
<211> LENGTH: 200
<212> TYPE: PRT
<213> ORGANISM: Artificial sequence
<220> FEATURE:
<223> OTHER INFORMATION: Synthetic

<400> SEQUENCE: 7

Pro Gly Gly Gly Val Pro Gly Gly Val Pro Gly Ala Val Pro Gly Val
1               5                   10                  15

Pro Gly Ala Val Val Pro Val Val Gly Gly Val Pro Gly Val Val Gly
                20                  25                  30

Val Pro Gly Gly Val Pro Val Gly Val Val Pro Gly Val Pro
            35                  40                  45

Val Gly Val Pro Gly Val Pro Val Val Gly Gly Val Pro Ala Gly
            50                  55                  60

Gly Val Val Pro Gly Gly Gly Val Pro Val Gly Gly Val Val Pro
65                  70                  75                  80

Gly Val Gly Val Val Pro Gly Val Pro Val Val Gly Gly Gly
                85                  90                  95

Val Gly Val Pro Gly Val Val Pro Gly Val Pro Gly Val Gly Val Pro
                100                 105                 110

Val Gly Gly Val Pro Gly Gly Val Val Pro Gly Gly Val Gly
            115                 120                 125

Val Pro Val Val Gly Val Val Pro Gly Ala Pro Gly Val Pro Gly Val
                130                 135                 140

Pro Gly Gly Val Gly Gly Val Pro Val Gly Val Gly Val Pro Gly Gly
145                 150                 155                 160

Gly Ala Pro Gly Val Val Pro Gly Gly Ala Val Pro Gly Gly Ala Pro
```

```
                    165                 170                 175

Val Gly Gly Val Gly Gly Val Pro Gly Val Gly Val Pro Gly
                180                 185                 190

Ala Pro Gly Gly Val Pro Gly Gly
        195                 200

<210> SEQ ID NO 8
<211> LENGTH: 200
<212> TYPE: PRT
<213> ORGANISM: Artificial sequence
<220> FEATURE:
<223> OTHER INFORMATION: Synthetic

<400> SEQUENCE: 8

Pro Gly Gly Val Pro Gly Val Pro Ala Gly Gly Ala Gly Val Pro
1               5                   10                  15

Gly Val Pro Gly Ala Pro Ala Gly Gly Ala Pro Gly Val Ala Pro
                20                  25                  30

Gly Gly Val Val Pro Gly Val Pro Gly Val Ala Pro Val Val Gly Gly
            35                  40                  45

Gly Ala Pro Gly Gly Val Pro Gly Ala Val Pro Gly Val Pro Gly Gly
        50                  55                  60

Val Pro Gly Gly Val Val Val Pro Gly Gly Val Gly Ala Pro Gly
65                  70                  75                  80

Gly Val Ala Pro Val Gly Gly Val Pro Val Val Gly Gly Val Pro
                85                  90                  95

Val Gly Gly Val Ala Pro Gly Val Pro Val Gly Val Pro Gly Val Gly
                100                 105                 110

Val Gly Val Gly Val Pro Val Gly Gly Val Gly Gly Val Pro Gly
            115                 120                 125

Val Val Pro Ala Gly Val Pro Gly Gly Val Ala Gly Val Val Pro
        130                 135                 140

Val Gly Gly Val Pro Val Val Gly Ala Pro Gly Gly Gly Val Gly
145                 150                 155                 160

Val Pro Gly Ala Pro Gly Ala Gly Gly Val Pro Gly Gly Ala Pro Gly
                165                 170                 175

Ala Pro Gly Val Val Ala Pro Gly Gly Val Pro Val Gly Val Val
                180                 185                 190

Pro Gly Val Val Pro Gly Gly Gly
        195                 200

<210> SEQ ID NO 9
<211> LENGTH: 400
<212> TYPE: PRT
<213> ORGANISM: Artificial sequence
<220> FEATURE:
<223> OTHER INFORMATION: Synthetic

<400> SEQUENCE: 9

Pro Gly Gly Val Pro Gly Val Gly Gly Val Pro Gly Val Pro Gly
1               5                   10                  15

Ala Pro Gly Val Val Pro Gly Val Val Val Pro Gly Gly Val Pro
                20                  25                  30

Val Gly Gly Val Pro Gly Val Pro Val Val Gly Gly Val Pro Val
            35                  40                  45

Gly Gly Gly Val Gly Gly Val Pro Gly Ala Pro Gly Gly Gly Val Pro
        50                  55                  60
```

-continued

```
Gly Ala Pro Val Gly Gly Val Pro Val Gly Val Pro Gly Val
 65                  70                  75                  80

Gly Val Pro Gly Ala Gly Gly Val Pro Gly Val Gly Val Val
                 85                  90                  95

Pro Val Gly Gly Ala Pro Gly Val Pro Gly Val Val Pro Gly
            100                 105                 110

Val Pro Val Gly Gly Val Pro Ala Gly Val Pro Gly Val Gly
        115                 120                 125

Val Gly Gly Gly Val Val Pro Gly Val Val Gly Pro Gly Gly
    130                 135                 140

Val Gly Gly Gly Val Gly Val Pro Gly Gly Ala Pro Gly Gly Val
145                 150                 155                 160

Val Gly Gly Gly Val Pro Gly Gly Val Val Pro Val Val Gly Gly
                165                 170                 175

Val Pro Gly Ala Val Pro Gly Val Pro Gly Val Val Pro Val Gly
            180                 185                 190

Gly Gly Val Val Pro Val Gly Val Pro Gly Gly Val Val Pro Gly
        195                 200                 205

Val Pro Gly Gly Val Val Gly Val Pro Val Val Gly Val Pro Gly Val
    210                 215                 220

Gly Val Val Pro Gly Val Pro Gly Val Pro Val Gly Val Gly Val Val
225                 230                 235                 240

Val Pro Gly Val Val Pro Gly Gly Val Gly Val Pro Gly Val Pro Gly
                245                 250                 255

Gly Gly Val Pro Gly Val Gly Val Pro Val Gly Gly Ala Pro Gly Val
            260                 265                 270

Pro Gly Val Pro Gly Val Ala Val Pro Gly Val Val Pro Gly Gly Ala
        275                 280                 285

Pro Gly Val Pro Val Gly Val Val Pro Val Gly Val Val Pro Gly Gly
    290                 295                 300

Gly Val Gly Val Val Pro Gly Gly Val Pro Gly Gly Val Pro Gly Val
305                 310                 315                 320

Pro Ala Gly Val Pro Val Gly Val Pro Val Gly Gly Val Gly Gly Val
                325                 330                 335

Val Pro Gly Gly Gly Ala Pro Gly Val Gly Val Gly Val Pro Ala Gly
            340                 345                 350

Val Pro Gly Gly Val Pro Val Gly Val Gly Gly Val Pro Gly Gly Val
        355                 360                 365

Val Pro Gly Val Pro Ala Gly Gly Gly Val Pro Val Gly Val Pro Gly
    370                 375                 380

Val Gly Gly Val Pro Val Gly Ala Pro Gly Val Pro Gly Gly Val Pro
385                 390                 395                 400
```

<210> SEQ ID NO 10
<211> LENGTH: 400
<212> TYPE: PRT
<213> ORGANISM: Artificial sequence
<220> FEATURE:
<223> OTHER INFORMATION: Synthetic

<400> SEQUENCE: 10

```
Pro Ala Gly Ala Val Pro Gly Gly Val Pro Val Ala Gly Gly Val Pro
 1               5                  10                  15

Val Gly Ala Gly Val Val Ala Pro Gly Ala Pro Val Gly Gly Ala Pro
                 20                  25                  30
```

Gly Val Val Gly Val Pro Gly Gly Val Pro Gly Val Val
         35                  40                  45

Gly Val Gly Val Gly Val Pro Val Gly Gly Val Gly Val Val Pro
 50                  55                  60

Ala Gly Gly Gly Ala Pro Gly Val Gly Val Val Pro Gly Val
 65                  70                  75                  80

Val Pro Gly Ala Pro Ala Gly Val Pro Gly Val Ala Pro Gly Gly
                 85                  90                  95

Val Gly Gly Val Pro Gly Val Val Pro Gly Gly Val Val Pro Gly
                100                 105                 110

Val Ala Pro Gly Val Pro Gly Val Pro Gly Gly Val Pro Val Gly Val
            115                 120                 125

Pro Val Gly Ala Ala Pro Gly Gly Val Pro Ala Val Gly Val Pro
 130                 135                 140

Gly Val Gly Gly Gly Val Pro Val Val Gly Ala Gly Ala Pro Gly Gly
145                 150                 155                 160

Val Pro Gly Val Ala Val Pro Gly Ala Pro Gly Gly Val Pro Val Gly
                165                 170                 175

Gly Val Pro Gly Gly Val Gly Gly Val Val Pro Gly Gly Val Pro
                180                 185                 190

Gly Ala Pro Val Gly Val Val Pro Gly Val Gly Val Val Pro Gly Val
                195                 200                 205

Pro Ala Gly Val Gly Val Pro Gly Ala Pro Gly Ala Pro Gly Gly
 210                 215                 220

Val Pro Gly Gly Ala Pro Val Gly Ala Gly Gly Val Pro Gly
225                 230                 235                 240

Gly Val Pro Gly Val Pro Gly Ala Pro Gly Val Gly Val Pro Gly Val
                245                 250                 255

Gly Val Pro Val Gly Val Pro Gly Val Pro Gly Val Pro Val Gly Gly
                260                 265                 270

Gly Ala Gly Val Pro Gly Gly Val Ala Pro Gly Val Ala Val Pro Gly
            275                 280                 285

Gly Val Gly Val Pro Val Val Gly Gly Val Pro Gly Ala Val Pro Gly
 290                 295                 300

Val Pro Gly Val Gly Gly Ala Pro Gly Val Pro Gly Gly Gly Val Val
305                 310                 315                 320

Gly Val Gly Val Pro Gly Gly Val Val Pro Gly Val Pro Gly Ala Gly
                325                 330                 335

Ala Pro Gly Gly Gly Ala Pro Gly Ala Pro Val Gly Val Pro Gly Gly
                340                 345                 350

Ala Pro Gly Val Val Pro Gly Val Gly Gly Val Pro Gly Ala Gly Gly
                355                 360                 365

Gly Val Val Gly Gly Val Val Pro Val Gly Gly Val Val Pro
 370                 375                 380

Gly Ala Pro Gly Gly Ala Pro Val Gly Gly Val Val Gly Gly Val Pro
385                 390                 395                 400

<210> SEQ ID NO 11
<211> LENGTH: 240
<212> TYPE: PRT
<213> ORGANISM: Artificial sequence
<220> FEATURE:
<223> OTHER INFORMATION: Synthetic

<400> SEQUENCE: 11

```
Pro Val Gly Val Pro Gly Val Gly Gly Ala Pro Val Val Gly Gly
1               5                   10                  15
Ala Pro Val Gly Val Gly Gly Ala Gly Val Val Pro Gly Ala Pro
            20                  25                  30
Val Gly Ala Val Ala Gly Val Gly Ala Pro Gly Gly Ala Val Pro Ala
            35                  40                  45
Gly Gly Ala Pro Gly Val Gly Ala Pro Gly Val Val Pro Gly Ala Val
    50                  55                  60
Pro Gly Val Gly Val Gly Gly Val Gly Gly Val Val Val Pro Val
65                  70                  75                  80
Val Val Gly Val Gly Gly Val Pro Ala Gly Ala Val Pro Val Gly Gly
            85                  90                  95
Val Ala Pro Val Gly Val Pro Val Gly Ala Gly Gly Ala Pro Ala
            100                 105                 110
Gly Gly Val Pro Val Ala Val Gly Val Pro Val Val Gly Gly Val
            115                 120                 125
Pro Gly Val Gly Val Val Gly Val Ala Pro Gly Ala Pro Gly Ala Gly
    130                 135                 140
Val Gly Val Val Ala Gly Ala Gly Ala Ala Val Ala Pro Val Gly
145                 150                 155                 160
Val Ala Pro Gly Val Pro Gly Val Pro Gly Ala Val Val Gly Val Pro
            165                 170                 175
Gly Gly Val Ala Pro Ala Val Val Val Gly Ala Val Pro Gly Val Val
            180                 185                 190
Gly Val Val Pro Val Gly Ala Pro Val Val Ala Gly Gly Val Ala Val
            195                 200                 205
Ala Pro Val Gly Gly Ala Val Pro Gly Val Pro Gly Gly Val Pro Gly
            210                 215                 220
Gly Gly Ala Pro Gly Ala Pro Val Val Gly Val Pro Val Gly Val Pro
225                 230                 235                 240

<210> SEQ ID NO 12
<211> LENGTH: 240
<212> TYPE: PRT
<213> ORGANISM: Artificial sequence
<220> FEATURE:
<223> OTHER INFORMATION: Synthetic

<400> SEQUENCE: 12

Pro Val Gly Ser Pro Gly Ser Val Pro Gly Val Val Pro Val Ser Gly
1               5                   10                  15
Val Val Val Gly Gly Gly Ser Val Pro Gly Ser Ser Pro Val Val Gly
            20                  25                  30
Val Pro Ser Gly Val Pro Val Gly Ser Pro Val Val Gly Gly Gly Val
            35                  40                  45
Ser Pro Gly Val Gly Val Pro Gly Val Val Pro Gly Val Pro Val
    50                  55                  60
Gly Gly Gly Val Gly Val Pro Gly Gly Gly Val Val Gly Gly Val Pro
65                  70                  75                  80
Val Val Val Gly Val Ser Val Pro Ser Gly Val Ser Pro Gly Gly
            85                  90                  95
Val Val Val Pro Val Gly Ser Val Ser Ser Gly Val Pro Val Val Ser
            100                 105                 110
Val Val Gly Val Ser Val Val Pro Gly Ser Val Pro Val Gly Ser Pro
            115                 120                 125
```

```
Ser Ser Gly Val Pro Gly Val Val Pro Gly Ser Pro Gly Gly Val Val
    130                 135                 140

Gly Ser Ser Val Pro Ser Gly Ser Gly Val Ser Val Pro Val Gly
145                 150                 155                 160

Val Gly Gly Ser Gly Val Pro Gly Val Pro Gly Ser Gly Ser Val Val
                165                 170                 175

Pro Val Gly Val Ser Pro Val Gly Gly Ser Gly Ser Gly Val Gly
                180                 185                 190

Ser Gly Ser Pro Gly Gly Ser Val Pro Gly Gly Ser Pro Gly Val Val
            195                 200                 205

Pro Val Gly Ser Pro Gly Val Gly Gly Val Pro Gly Val Val Gly Gly
            210                 215                 220

Ser Gly Ser Pro Gly Val Pro Gly Gly Val Gly Val Gly Val Pro Gly
225                 230                 235                 240

<210> SEQ ID NO 13
<211> LENGTH: 240
<212> TYPE: PRT
<213> ORGANISM: Artificial sequence
<220> FEATURE:
<223> OTHER INFORMATION: Synthetic

<400> SEQUENCE: 13

Pro Val Gly Thr Pro Gly Thr Val Pro Gly Gly Val Val Pro Val Gly
1               5                   10                  15

Val Thr Pro Val Gly Gly Gly Thr Gly Thr Pro Thr Thr Val Thr Val
                20                  25                  30

Val Gly Gly Val Val Val Pro Gly Val Pro Gly Gly Thr Pro Gly
            35                  40                  45

Val Pro Val Gly Thr Pro Val Val Gly Gly Val Gly Val Gly Thr Gly
        50                  55                  60

Thr Pro Gly Gly Thr Val Pro Gly Gly Thr Pro Gly Val Val Pro Gly
65                  70                  75                  80

Thr Pro Gly Gly Val Val Pro Gly Thr Thr Val Pro Thr Gly Thr Gly
                85                  90                  95

Thr Thr Pro Val Val Gly Val Pro Thr Val Gly Gly Val Thr Pro Gly
            100                 105                 110

Val Gly Gly Val Pro Val Val Gly Thr Gly Val Pro Gly Val Pro
        115                 120                 125

Val Gly Gly Gly Val Gly Val Val Gly Val Val Pro Gly Thr Val
    130                 135                 140

Pro Val Gly Val Pro Gly Val Val Gly Gly Thr Val Pro Val Gly Thr
145                 150                 155                 160

Pro Thr Thr Gly Val Pro Gly Val Pro Thr Gly Val Thr Pro Gly
                165                 170                 175

Gly Val Gly Val Pro Gly Gly Val Val Gly Gly Val Val Pro Gly
                180                 185                 190

Val Thr Val Pro Val Gly Thr Val Thr Thr Gly Val Pro Val Val Thr
            195                 200                 205

Val Gly Val Val Pro Val Gly Thr Val Gly Gly Val Val Val Gly
        210                 215                 220

Gly Gly Thr Thr Pro Gly Gly Val Pro Gly Thr Pro Gly Val Gly Gly
225                 230                 235                 240

<210> SEQ ID NO 14
<211> LENGTH: 240
```

```
<212> TYPE: PRT
<213> ORGANISM: Artificial sequence
<220> FEATURE:
<223> OTHER INFORMATION: Synthetic

<400> SEQUENCE: 14

Gly Ala Val Val Pro Gly Gly Ala Val Gly Val Pro Ala Gly Ala
1               5                   10                  15

Val Gly Gly Val Gly Gly Val Leu Val Pro Ala Val Gly Ala Val Pro
            20                  25                  30

Gly Gly Gly Val Pro Ala Val Gly Val Pro Val Ala Gly Val Val Pro
        35                  40                  45

Gly Gly Leu Pro Gly Gly Ala Gly Val Gly Ala Leu Gly Ala Ala Ala
    50                  55                  60

Pro Gly Gly Val Pro Val Gly Ala Ala Leu Pro Gly Val Ala Gly Val
65                  70                  75                  80

Ala Pro Gly Gly Gly Leu Pro Gly Leu Gly Ala Gly Ala Gly Leu Gly
                85                  90                  95

Leu Ala Gly Ala Leu Val Leu Pro Gly Leu Gly Val Pro Gly Val
                100                 105                 110

Pro Gly Gly Gly Leu Leu Pro Gly Gly Val Pro Leu Leu Gly Leu Pro
            115                 120                 125

Gly Val Pro Ala Gly Leu Pro Gly Val Leu Pro Val Gly Leu Leu Leu
        130                 135                 140

Pro Gly Ala Pro Gly Val Pro Ala Leu Gly Val Pro Leu Gly Val Pro
145                 150                 155                 160

Gly Val Ala Pro Gly Leu Pro Gly Ala Gly Leu Pro Gly Val Gly
                165                 170                 175

Ala Pro Gly Leu Leu Pro Val Gly Gly Ala Pro Ala Leu Gly Gly
            180                 185                 190

Leu Gly Leu Pro Gly Gly Gly Ala Leu Gly Leu Leu Ala Pro Gly Gly
                195                 200                 205

Ala Leu Val Pro Gly Val Gly Gly Val Ala Pro Val Ala Ala Gly Ala
        210                 215                 220

Leu Leu Pro Gly Gly Ala Pro Leu Gly Val Pro Ala Leu Leu Ala Leu
225                 230                 235                 240

<210> SEQ ID NO 15
<211> LENGTH: 240
<212> TYPE: PRT
<213> ORGANISM: Artificial sequence
<220> FEATURE:
<223> OTHER INFORMATION: Synthetic

<400> SEQUENCE: 15

Ser Ser Gly Ser Ser Gly Ser Gly Phe Phe Ser Gly Gly Val Pro Ser
1               5                   10                  15

Gly Gly Gly Val Val Phe Val Pro Ser Phe Phe Gly Phe Phe Pro Ser
            20                  25                  30

Gly Ser Gly Gly Val Val Pro Gly Val Pro Gly Gly Val Gly Val
        35                  40                  45

Pro Gly Phe Val Gly Val Pro Val Gly Gly Phe Val Pro Val Gly Val Pro
    50                  55                  60

Gly Val Phe Val Pro Ser Val Val Gly Val Gly Phe Phe Val Phe
65                  70                  75                  80

Pro Gly Val Pro Gly Gly Ser Ser Ser Pro Gly Ser Pro Phe Gly Val
                85                  90                  95
```

```
Phe Gly Gly Ser Gly Gly Phe Phe Gly Ser Ser Pro
            100                 105             110

Gly Val Val Ser Pro Gly Phe Gly Val Pro Phe Gly Val
            115                 120             125

Pro Val Gly Gly Ser Val Phe Phe Pro Phe Gly Gly Phe Pro
130                 135                 140

Gly Gly Phe Pro Ser Gly Ser Phe Gly Val Pro Gly Gly Phe Val
145                 150                 155                 160

Val Pro Phe Gly Val Ser Pro Gly Ser Pro Gly Phe Val Pro Ser Phe
                165                 170                 175

Gly Ser Pro Gly Gly Phe Gly Gly Phe Ser Pro Phe Ser Ser Gly Val
            180                 185                 190

Gly Ser Pro Gly Gly Val Pro Gly Val Gly Val Val Ser Pro Gly Phe
            195                 200                 205

Pro Gly Gly Ser Pro Phe Gly Phe Pro Gly Ser Pro Gly Gly Ser Phe
            210                 215                 220

Gly Gly Ser Pro Ser Val Phe Gly Ser Gly Ser Pro Gly Ser Phe Pro
225                 230                 235                 240
```

<210> SEQ ID NO 16
<211> LENGTH: 240
<212> TYPE: PRT
<213> ORGANISM: Artificial sequence
<220> FEATURE:
<223> OTHER INFORMATION: Synthetic

<400> SEQUENCE: 16

```
Ala Ala Gly Gly Thr Gly Phe Phe Thr Gly Gly Ala Pro Gly Gly Thr
1               5                   10                  15

Pro Thr Ala Phe Gly Gly Phe Thr Pro Phe Thr Phe Ala Gly Gly Gly
            20                  25                  30

Ala Pro Gly Phe Phe Ala Phe Pro Gly Ala Pro Gly Thr Phe Pro Thr
            35                  40                  45

Phe Gly Ala Pro Gly Ala Ala Pro Gly Thr Thr Pro Gly Thr Phe
50                  55                  60

Phe Gly Phe Pro Gly Gly Thr Pro Gly Thr Pro Gly Ala Ala Thr Pro
65                  70                  75                  80

Gly Phe Phe Gly Ala Phe Gly Phe Pro Gly Ala Phe Ala Thr Phe Gly
                85                  90                  95

Phe Pro Gly Gly Gly Ala Gly Ala Ala Pro Ala Gly Thr Pro Gly Ala
            100                 105                 110

Pro Thr Ala Ala Gly Ala Thr Thr Pro Gly Ala Gly Gly Thr Thr Gly
            115                 120                 125

Gly Ala Pro Thr Gly Gly Gly Phe Ala Pro Thr Phe Gly Phe Phe
            130                 135                 140

Pro Thr Gly Thr Gly Gly Ala Ala Pro Gly Ala Pro Gly Gly Gly Thr
145                 150                 155                 160

Thr Thr Phe Pro Gly Ala Thr Pro Phe Gly Phe Pro Gly Thr Gly Thr
                165                 170                 175

Pro Gly Thr Phe Gly Ala Pro Gly Gly Phe Pro Gly Ala Gly
            180                 185                 190

Phe Gly Gly Gly Ala Pro Gly Ala Pro Ala Ala Ala Gly Gly Gly Thr
            195                 200                 205

Pro Gly Thr Ala Thr Pro Gly Thr Phe Pro Thr Gly Ala Gly Thr Phe
210                 215                 220
```

-continued

```
Pro Gly Thr Phe Pro Phe Gly Gly Phe Pro Gly Gly Phe Pro Thr
225                 230                 235                 240

<210> SEQ ID NO 17
<211> LENGTH: 240
<212> TYPE: PRT
<213> ORGANISM: Artificial sequence
<220> FEATURE:
<223> OTHER INFORMATION: Synthetic

<400> SEQUENCE: 17

Thr Ile Leu Pro Gly Ile Gly Leu Pro Gly Gly Leu Pro Leu Thr Ile
1               5                   10                  15

Gly Gly Ile Leu Pro Ile Leu Leu Gly Thr Thr Ile Gly Gly Ile Pro
                20                  25                  30

Gly Gly Gly Ile Ile Pro Gly Ile Gly Gly Ile Pro Ile Leu Thr
            35                  40                  45

Leu Leu Ile Leu Pro Thr Gly Leu Pro Gly Thr Pro Leu Thr Thr Gly
    50                  55                  60

Thr Pro Gly Ile Thr Gly Leu Gly Thr Pro Leu Gly Ile Gly Leu Ile
65                  70                  75                  80

Gly Thr Gly Ile Pro Gly Gly Gly Thr Gly Ile Pro Thr Gly Ile Pro
                85                  90                  95

Gly Thr Thr Leu Pro Gly Ile Pro Thr Leu Gly Gly Gly Ile Pro Leu
                100                 105                 110

Ile Gly Thr Pro Gly Gly Ile Gly Thr Ile Gly Ile Pro Gly Thr Gly
            115                 120                 125

Thr Ile Ile Gly Ile Pro Gly Gly Leu Leu Leu Ile Pro Gly Ile
    130                 135                 140

Thr Pro Leu Ile Gly Leu Pro Gly Gly Thr Pro Gly Thr Pro Gly Gly
145                 150                 155                 160

Gly Thr Gly Thr Thr Pro Thr Gly Leu Pro Gly Ile Leu Leu Pro Gly
                165                 170                 175

Gly Leu Pro Gly Ile Pro Thr Gly Thr Pro Gly Thr Gly Thr Pro Ile
                180                 185                 190

Gly Gly Leu Leu Ile Leu Leu Thr Leu Pro Gly Leu Pro Gly Leu Gly
            195                 200                 205

Leu Pro Gly Leu Ile Pro Leu Gly Thr Gly Leu Thr Gly Gly Thr Pro
    210                 215                 220

Thr Gly Gly Ile Pro Gly Gly Ile Gly Ile Pro Gly Ile Leu Thr Thr
225                 230                 235                 240

<210> SEQ ID NO 18
<211> LENGTH: 240
<212> TYPE: PRT
<213> ORGANISM: Artificial sequence
<220> FEATURE:
<223> OTHER INFORMATION: Synthetic

<400> SEQUENCE: 18

Pro Gly Thr Tyr Pro Gly Tyr Gly Tyr Val Tyr Pro Thr Thr Gly Gly
1               5                   10                  15

Ile Pro Gly Gly Val Val Pro Gly Gly Gly Thr Lys Leu Val Pro Gly
                20                  25                  30

Lys Gly Lys Gly Gly Ala Lys Ala Pro Gly Thr Val Pro Val Gly Ala
            35                  40                  45

Gly Gly Gly Lys Ile Val Pro Ile Tyr Gly Ile Ala Pro Gly Lys Tyr
```

```
            50                  55                  60
Gly Tyr Pro Gly Gly Ile Val Pro Gly Ile Thr Thr Pro Gly Leu
 65                  70                  75                  80

Pro Thr Gly Lys Lys Pro Tyr Gly Val Pro Val Leu Tyr Gly Lys
                 85                  90                  95

Leu Pro Gly Ala Pro Gly Ile Pro Thr Ala Gly Ala Pro Gly Tyr Ile
            100                 105                 110

Ala Pro Gly Val Pro Gly Leu Val Lys Gly Thr Gly Ile Ala
            115                 120                 125

Pro Leu Gly Val Ile Leu Val Tyr Ile Gly Val Gly Gly Ile Lys Gly
            130                 135                 140

Gly Ala Leu Pro Thr Gly Gly Leu Tyr Pro Gly Ala Gly Thr Pro Gly
145                 150                 155                 160

Tyr Pro Val Gly Gly Ala Pro Ala Gly Ile Ala Leu Lys Pro
                165                 170                 175

Gly Ile Thr Pro Gly Thr Ala Ala Pro Gly Leu Pro Gly Lys Gly Gly
                180                 185                 190

Lys Tyr Thr Tyr Pro Gly Gly Ala Pro Gly Gly Thr Gly Val Pro
                195                 200                 205

Gly Tyr Pro Gly Leu Ala Leu Lys Leu Gly Ile Pro Thr Lys Gly Gly
            210                 215                 220

Gly Ile Gly Leu Pro Tyr Ile Gly Leu Leu Pro Gly Lys Pro Gly Gly
225                 230                 235                 240

<210> SEQ ID NO 19
<211> LENGTH: 6
<212> TYPE: PRT
<213> ORGANISM: Artificial sequence
<220> FEATURE:
<223> OTHER INFORMATION: Synthetic

<400> SEQUENCE: 19

Met Ser Lys Gly Pro Gly
 1               5

<210> SEQ ID NO 20
<211> LENGTH: 3
<212> TYPE: PRT
<213> ORGANISM: Artificial sequence
<220> FEATURE:
<223> OTHER INFORMATION: Synthetic

<400> SEQUENCE: 20

Gly Trp Pro
 1

<210> SEQ ID NO 21
<211> LENGTH: 15
<212> TYPE: PRT
<213> ORGANISM: Artificial sequence
<220> FEATURE:
<223> OTHER INFORMATION: Synthetic

<400> SEQUENCE: 21

Gly Gly Gly Gly Ser Gly Gly Gly Gly Ser Gly Gly Gly Gly Ser
 1               5                  10                  15

<210> SEQ ID NO 22
<211> LENGTH: 19
<212> TYPE: PRT
<213> ORGANISM: Artificial sequence
```

```
<220> FEATURE:
<223> OTHER INFORMATION: Synthetic

<400> SEQUENCE: 22

Pro Gln Pro Gln Pro Lys Pro Gln Pro Lys Pro Glu Pro Glu Pro Gln
1               5                   10                  15

Pro Gln Gly

<210> SEQ ID NO 23
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (4)..(4)
<223> OTHER INFORMATION: any amino acid except proline

<400> SEQUENCE: 23

Val Pro Gly Xaa Gly
1               5
```